(12) United States Patent
Sit et al.

(10) Patent No.: US 6,949,574 B2
(45) Date of Patent: Sep. 27, 2005

(54) (OXIME)CARBAMOYL FATTY ACID AMIDE HYDROLASE INHIBITORS

(75) Inventors: Sing-Yuen Sit, Meriden, CT (US); Kai Xie, Wallingford, CT (US); Hongfeng Deng, Acton, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 71 days.

(21) Appl. No.: 10/357,807

(22) Filed: Feb. 4, 2003

(65) Prior Publication Data

US 2003/0195226 A1 Oct. 16, 2003

Related U.S. Application Data

(60) Provisional application No. 60/355,302, filed on Feb. 8, 2002.

(51) Int. Cl.$^7$ .................. C07D 213/02; A61K 31/47
(52) U.S. Cl. .................. 514/357; 514/311; 514/415; 514/468; 514/476; 514/477; 514/478; 546/134; 546/291; 548/452; 549/433; 558/233
(58) Field of Search .................. 514/311, 357, 514/415, 468, 476, 477, 478; 546/134, 291; 548/452; 549/433; 558/233

(56) References Cited

FOREIGN PATENT DOCUMENTS

| DE | 1174757 | * | 7/1964 |
|----|---------|---|--------|
| DE | 1232947 | * | 1/1967 |
| GB | 841141  | * | 7/1960 |
| WO | WO 90/01874 | * | 3/1990 |

OTHER PUBLICATIONS

Levine, J. D., New Directions in Pain Research: Meeting Report Molecules to Maladies, Neuron 20: 649–654, 1998.
Pasternak, G. W., The Central Questions in Pain Perception May Be Peripheral, Proc. Natl. Acad. Sci. USA, 95:10354–10355, 1998.
Devane, W. A. et al., Isolation and Structure of a Brain Constituent That Binds to the Cannabinoid Receptors, Science 258: 1946–1949, 1992.
Hanus, L. et. al., Two New Unsaturated Fatty Acid Ethanolamides in Brain that Bind to the Cannabinoid Receptor, J. Med. Chem. 36: 3032–3034, 1993.
Machoulam, R. et. al., Identification of an Endogenous 2–Monoglyceride, Present in Canine Gut, That Binds To Cannabinoid Receptors, Biochem. Pharmacol. 50: 83–90, 1995.
Barg, J. et. al., Cannabinomimetic Behavioral Effects of and Adenylate Cyclase Inhibition By Two New Endogenous Anandamides, Eur. J. Pharmacol. 287: 145–152, 1995.
Richardson, J. D. et al., Cannabinoids Reduce Hyperalgesia and Inflammation Via Interaction With Peripheral CB1 Receptors, Pain 75: 111–119, 1998.
Jaggar, S.I., et al., The Anti–Hyperalgesic Actions of the Cannabinoid Anandamide and the Putative CB2 Receptor Agonist Palmitoylethanolamide in Visceral and Somatic Inflammatory Pain, Pain 76: 189–199, 1998.
Huang, S.M., et al., Identification of a New Class of Molecules, the Arachidonyl Amino Acids, and Characterization of One Member That Inhibits Pain, J. Biological Chemistry, 276: 46, 42639–42644, 2001
Richardson, J.D. et al., Hypoactivity of the Spinal Cannabinoid System Results in NMDA–Dependent Hyperalgesia ,J. Neurosci. 18: 451–457, 1998.
Calignano, A. et. al., Control of Pain Initiation By Endogenous Cannabinoids, Nature 394: 277–281, 1998.
Meng, I.D. et. al., An Analgesia Circuit Activated By Cannabinoids, Nature 395: 381–383, 1998.

* cited by examiner

*Primary Examiner*—Zinna Northington Davis
(74) *Attorney, Agent, or Firm*—James Epperson; Shah R. Makujina

(57) ABSTRACT

The present invention relates to novel oxime carbamyl derivatives and pharmaceutical compositions comprising said derivatives which inhibit fatty acid amide hydrolase. These pharmaceutical compositions are useful for the treatment of conditions which can be effected by inhibiting fatty acid amide hydrolase including, but not limited to, neuropathic pain, emesis, anxiety, altering feeding behaviors, movement disorders, glaucoma, brain injury, and cardiovascular disease.

21 Claims, 3 Drawing Sheets

(OXIME)CARBAMOYL FATTY ACID AMIDE HYDROLASE INHIBITORS

CROSS REFERENCE TO RELATED APPLICATION

This non-provisional application claims priority from provisional application U.S. Ser. No. 60/355,302 filed Feb. 8, 2002.

FIELD OF THE INVENTION

The present invention relates to novel (oxime)carbamoyl derivatives and pharmaceutical compositions comprising said derivatives which inhibit fatty acid amide hydrolase and are useful for the treatment of conditions which can be effected by inhibiting fatty acid amide hydrolase.

BACKGROUND OF THE INVENTION

Effective treatment of pain with current therapies is limited by adverse effects and a lack of efficacy against all components of pain.

Current research is aimed at understanding the molecular and physiological components of pain processing to develop more effective analgesics (Levine, J. D., New Directions in Pain Research: Meeting Report Molecules to Maladies, Neuron 20: 649–654, 1998; Pasternak, G. W., The Central Questions in Pain Perception May Be Peripheral, PNAS 95:10354–10355, 1998).

The analgesic properties of cannabinoids have been known for many years and to many cultures. Cannabinoids are active in many pre-clinical models of pain, including neuropathic pain. Within the last few years, several endogenous cannabinoids, including the fatty acid amides arachidonylethanolamide (anandamide), and arachidonyl amino acids such as N-arachidonylglycine, homo-γ-linolenyl-ethanolamide and docosatetraenyl-ethanolamide, as well as 2-arachidonyl-glycerol, have been shown to induce analgesia in laboratory animals (DeVane, W. A. et. al., Isolation and Structure of a Brain Constituent That Binds to the Cannabinoid Receptors, Science 258: 1946–1949, 1992; Hanus, L. et. al., Two New Unsaturated Fatty Acid Ethanolamides in Brain that Bind to the Cannabinoid Receptor, J. Med. Chem. 36: 3032–3034, 1993; Machoulam, R. et. al., Identification of an Endogenous 2-Monoglyceride, Present in Canine Gut, That Binds To Cannabinoid Receptors, Biochem. Pharmacol. 50: 83–90, 1995; Vogel, Z. et. al., Cannabinomimetic Behavioral Effects of and Adenylate Cyclase Inhibition By Two New Endogenous Anandamides, Eur. J. Pharmacol. 287: 145–152, 1995; Hargreaves, K. M. et al., Cannabinoids Reduce Hyperalgesia and Inflammation Via Interaction With Peripheral CB1 Receptors, Pain 75: 111–119, 1998; Rice, A. S. C., et. al., The Anti-Hyperalgesic Actions of the Cannabinoid Anandamide and the Putative CB2 Receptor Agonist Palmitoylethanolamide in Visceral and Somatic Inflammatory Pain, Pain 76: 189–199, 1998; Huang, S. M., et al., Identification of a New Class of Molecules, the Arachidonyl Amino Acids, and Characterization of One Member That Inhibits Pain, J. Biological Chemistry, 276: 46, 42639–42644, 2001). The ability of cannabinoid receptor antagonists and cannabinoid receptor antisense to induce hyperalgesia in animals suggests that endogenous cannabinoids regulate the nociceptive threshold (Hargreaves, K. M. et al., Hypoactivity of the Spinal Cannabinoid System Results in NMDA-Dependent Hyperalgesia, J. Neurosci. 18: 451–457, 1998; Piomelli, D. et. al., Control of Pain Initiation By Endogenous Cannabinoids, Nature 394: 277–281, 1998; Fields, H. L. et. al., An Analgesia Circuit Activated By Cannabinoids, Nature 395: 381–383, 1998). Elevation of levels of neuroactive fatty acid amides such as anandamide may provide a unique mechanism to achieve analgesia. The mechanisms by which endogenous cannabinoids are synthesized are not well understood; therefore, targets for drugs aimed at increasing the synthesis of these compounds are slow to be identified.

Anandamide and the other identified endogenous cannabinoids are inactivated through a cleavage mechanism by a membrane-bound enzyme, fatty acid amide hydrolase (FAAH). FAAH, therefore, provides an important target for regulating the activity of endogenous cannabinoids. The inhibition of FAAH may elevate levels of anandamide or other endogenous cannabinoids to increase the nociceptive threshold. Furthermore, the inhibition of FAAH would also extend the therapeutic benefits of other cannabinoid agonists in the treatment of emesis, anxiety, feeding behaviors, movement disorders, glaucoma, neuroprotection and cardiovascular disease.

SUMMARY OF THE INVENTION

The above and other objects and advantages, which will be apparent to one of skill in the art, are achieved in the present invention which is directed to, in a first aspect, a compound of Formula I:

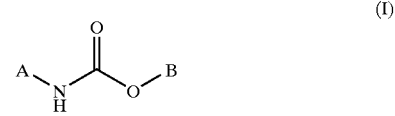
(I)

or a pharmaceutically acceptable salt or solvate thereof, wherein

A is dibenzofuranyl, dibenzothienyl, naphthyl, indolyl, fluorenyl, carbazolyl, or represented by Formula II:

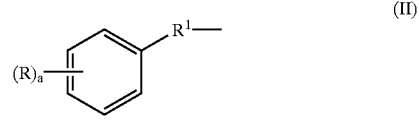
(II)

wherein a is 1 or 2,

R is $C_{1-16}$ alkoxy optionally substituted with phenyl, pyridyl or morpholinyl; phenyl optionally substituted with $C_{1-4}$ alkyl; phenoxy; phenyl-$C_{1-4}$ alkyloxy-; pyridyloxy; pyridyl-$C_{1-4}$ alkyloxy-; —N(H)—C(O)—$C_{1-16}$ alkyl; or —C(O)—N(H)—$C_{1-16}$ alkyl;

$R^1$ is a bond or a $C_{1-3}$ branched or linear aliphatic hydrocarbon; and

B is $C_{1-4}$ alkyl, indolyl, benzofuranyl, benzothienyl, dibenzofuranyl, dibenzohienyl, fluorenyl, carbazolyl, naphthyl, quinolinyl or isoquinolinyl, wherein each is optionally substituted with one or more of the same or different substituent selected from the group consisting of $C_{1-4}$ branched or linear aliphatic hydrocarbon, $C_{1-4}$ alkoxy, halo, haloalkyl, nitro and (C$_{1-3}$ alkyl)$_{0-2}$ amino-; or represented by Formula III, or Formula IV:

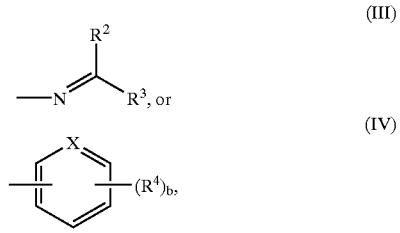

wherein
R$^2$ is hydrogen, halo or C$_{1-4}$ alkyl;
R$^3$ is C$_{1-4}$ alkyl, pyridyl, or phenyl optionally substituted with one or more of the same or different substituents selected from the group consisting of halo, C$_{1-4}$haloalkyl and nitro;
X is CH or nitrogen;
R$^4$ is C$_{1-4}$ branched or linear aliphatic hydrocarbon, C$_{1-4}$ alkoxy, halo, haloalkyl, nitro or amino; and
b is 0 to 3,
provided that if R$^2$ is halo, then R$^3$ is not halo; and if R$^3$ is halo, the R$^2$ is not halo.

According to another embodiment of the first aspect of the present invention are provided compounds of Formula I according to the first embodiment of the first aspect wherein A is dibenzofuranyl.

According to another embodiment of the first aspect of the present invention are provided compounds of Formula I according to the first embodiment of the first aspect wherein A is indolyl.

According to another embodiment of the first aspect of the present invention are provided compounds of Formula I according to the first embodiment of the first aspect wherein A is represented by Formula II:

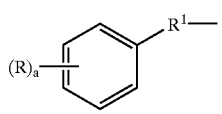

wherein
a is 1,
R is C$_{1-4}$ alkoxy optionally substituted with phenyl, phenoxy, pyridyloxy, or amido optionally substituted with C$_{1-16}$ alkyl,
R$^1$ is a bond; and
B is represented by Formula III:

wherein
R$^2$ is hydrogen, and
R$^3$ is methyl, pyridyl, phenyl optionally substituted with one or more halo, haloalkyl or nitro.

According to another embodiment of the first aspect of the present invention are provided compounds of Formula I according to the first embodiment of the first aspect wherein B is represented by Formula III:

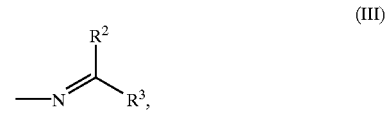

wherein
R$^2$ is hydrogen or methyl; and
R$^3$ is methyl or phenyl optionally substituted with one or more halo, haloalkyl or nitro.

According to another embodiment of the first aspect of the present invention are provided compounds of Formula I according to the first embodiment of the first aspect wherein B is represented by Formula III:

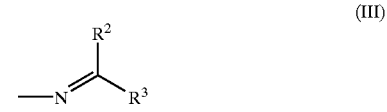

wherein R$^2$ is hydrogen or methyl; and R$^3$ is methyl, or phenyl optionally substituted with one or more halo, haloalkyl or nitro.

According to another embodiment of the first aspect of the present invention are provided compounds of Formula I according to the first embodiment of the first aspect wherein B is represented by Formula IV:

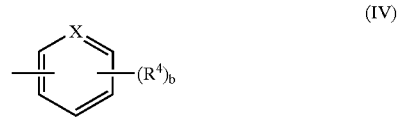

wherein X is CH; R$^4$ is halo; and b is 1.

According to another embodiment of the first aspect of the present invention are provided compounds of Formula I according to the first embodiment of the first aspect wherein B is represented by Formula IV:

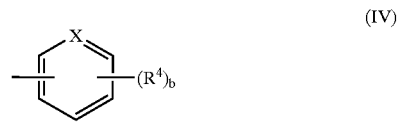

wherein X is nitrogen; and b is 0.

According to another embodiment of the first aspect of the present invention are provided compounds of Formula I according to the first embodiment of the first aspect wherein B is represented by Formula V:

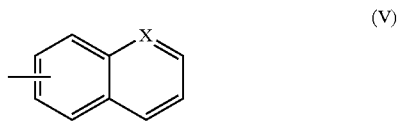

wherein X is nitrogen.

According to various embodiments of a second aspect of the present invention are provided compounds of Formula III, Formula IV or Formula V:

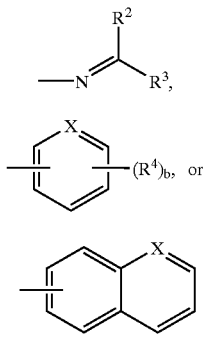

wherein
$R^2$ is hydrogen, or methyl,
$R^3$ is $C_{1-4}$ alkyl, pyridyl, or phenyl optionally substituted with one or more halo, haloalkyl or nitro,
X is CH or nitrogen,
$R^4$ is $C_{1-4}$ branched or linear aliphatic hydrocarbon, $C_{1-4}$ alkoxy, halo, haloalkyl or amino, and
b is 0 to 3.

According to various embodiments of a second aspect of the present invention are provided compounds of Formula VI:

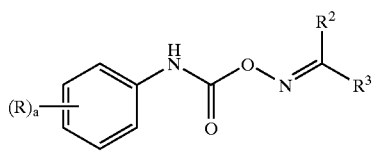

or a pharmaceutically acceptable salt or solvate thereof, wherein
a is 1;
R is $C_{1-12}$ alkoxy;
$R^2$ is hydrogen or methyl; and
$R^3$ is methyl, pyridyl, phenyl optionally substituted with one or more halo, haloalkyl or nitro.

According to another embodiment of the second aspect of the present invention are provided compounds of Formula VI according to the first embodiment of the second aspect wherein $R^2$ is hydrogen and $R^3$ is phenyl optionally substituted with one or more halo, haloalkyl or nitro.

According to another embodiment of the second aspect of the present invention are provided compounds of Formula VI according to the first embodiment of the second aspect wherein $R^2$ is methyl and $R^3$ is methyl.

According to another embodiment of the second aspect of the present invention are provided compounds of Formula VI according to the first embodiment of the second aspect, a member selected from the group consisting of
pyridine-3-carbaldehyde, O-[[(4-undecyloxy-phenyl)amino]carbonyl]oxime;
pyridine-3-carbaldehyde, O-[[(4-nonyloxy-phenyl)amino]carbonyl]oxime;
4-fluorobenzaldehyde, O-[[(4-decyloxy-phenyl)amino]carbonyl]oxime;
4-fluorobenzaldehyde, O-[[(4-octyloxy-phenyl)amino]carbonyl]oxime;
benzaldehyde, O-[[(4-nonyloxy-phenyl)amino]carbonyl]oxime;
4-fluorobenzaldehyde, O-[[(4-nonyloxy-phenyl)amino]carbonyl]oxime;
3,4-difluorobenzaldehyde, O-[[(4-nonyloxy-phenyl)amino]carbonyl]oxime;
2,6-difluorobenzaldehyde, O-[[(4-nonyloxy-phenyl)amino]carbonyl]oxime;
2,4-difluorobenzaldehyde, O-[[(4-nonyloxy-phenyl)amino]carbonyl]oxime;
3-fluorobenzaldehyde, O-[[(4-nonyloxy-phenyl)amino]carbonyl]oxime;
pyridine-3-carbaldehyde, O-[[(4-nonyloxy-phenyl)amino]carbonyl]oxime;
benzaldehyde, O-[[(4-decyloxy-phenyl)amino]carbonyl]oxime;
pyridine-3-carbaldehyde, O-[[(4-decyloxy-phenyl)amino]carbonyl]oxime;
pyridine-3-carbaldehyde, O-[[(4-dodecyloxy-phenyl)amino]carbonyl]oxime;
benzaldehyde, O-[[(4-octyloxy-phenyl)amino]carbonyl]oxime;
2,3-difluorobenzaldehyde, O-[[(4-nonyloxy-phenyl)amino]carbonyl]oxime;
benzaldehyde, O-[[(4-undecyloxy-phenyl)amino]carbonyl]oxime;
2,4,5-trifluorobenzaldehyde, O-[[(4-nonyloxy phenyl)amino]carbonyl]oxime;
4-fluorobenzaldehyde, O-[[(4-phenoxyphenyl)amino]carbonyl]oxime;
benzaldehyde, O-[[(4-undecyloxy-phenyl)amino]carbonyl]oxime;
4-trifluoromethyl-benzaldehyde, O-[[(4-nonyloxy-phenyl)amino]carbonyl]oxime;
benzaldehyde, O-[[(4-phenoxyphenyl)amino]carbonyl]oxime;
pyridine-3-carbaldehyde, O-[[(4-heptyloxy-phenyl)amino]carbonyl]oxime;
benzaldehyde, O-[[[4-(2-phenylethoxy)phenyl]amino]carbonyl]oxime;
2-fluoro-3-trifluoromethyl-benzaldehyde, O-[[(4-nonyloxy-phenyl)amino]carbonyl]oxime;
(4-undecyloxy-phenyl)-carbamic acid phenyl ester;
propan-2-one, O-[[(4-heptyloxy-phenyl)amino]carbonyl]oxime;
propan-2-one, O-[[(4-nonyloxy-phenyl)amino]carbonyl]oxime;
benzaldehyde, O-[[[4-(phenylmethoxy)phenyl]amino]carbonyl]oxime;
4-fluorobenzaldehyde, O-[[[4-(2-phenylethoxy)phenyl]amino]carbonyl]oxime;
2-fluoro-5-trifluoromethyl-benzaldehyde, O-[[(4-nonyloxy-phenyl)amino]carbonyl]oxime;
4-fluorobenzaldehyde, O-[[[4-(phenylmethoxy)phenyl]amino]carbonyl]oxime;
3-pyridinecarboxaldehyde, O-[[(3-phenoxyphenyl)amino]carbonyl]oxime;
4-fluorobenzaldehyde, O-[[[4-(3-phenylpropoxy)phenyl]amino]carbonyl]oxime;
benzaldehyde, O-[[(3-phenoxyphenyl)amino]carbonyl]oxime;
4-fluorobenzaldehyde, O-[[(4-pentyloxy-phenyl)amino]carbonyl]oxime;
4-fluorobenzaldehyde, O-[[(4-butoxy-phenyl)amino]carbonyl]oxime;
pyridine-3-carbaldehyde, O-[[(4-heptyloxyphenyl)amino]carbonyl]oxime;
3-pyridinecarboxaldehyde, O-[[(4-phenoxyphenyl)amino]carbonyl]oxime;

benzaldehyde, O-[[[4-(3-phenylpropoxy)phenyl]amino]carbonyl]oxime;
4-fluorobenzaldehyde, O-[[(4-pentyloxy-phenyl)amino]carbonyl]oxime;
4-fluorobenzaldehyde, O-[[(4-dodecyloxy-phenyl)amino]carbonyl]oxime;
propan-2-one, O-[[[(4-decyloxy-phenyl)amino]carbonyl]oxime;
benzaldehyde, O-[[(4-dodecyloxy-phenyl)amino]carbonyl]oxime;
benzaldehyde, O-[[(4-pentyloxy-phenyl)amino]carbonyl]oxime;
2,4-difluorobenzaldehyde, benzaldehyde, O-[[(4-nonanoylamino-phenyl)amino]carbonyl]oxime;
4-fluorobenzaldehyde, O-[[[(4-heptyloxy-phenyl)amino]carbonyl]oxime;
benzaldehyde, O-[[(4-pentyloxy-phenyl)amino]carbonyl]oxime;
propan-2-one, O-[[[(4-undecyloxy-phenyl)amino]carbonyl]oxime;
propan-2-one, O-[[[(4-dodecyloxy-phenyl)amino]carbonyl]oxime;
pyridine-3-carbaldehyde, O-[[(4-pentyloxy-phenyl)amino]carbonyl]oxime;
benzaldehyde, O-[[(4-propoxy-phenyl)amino]carbonyl]oxime;
benzaldehyde, O-[[(4-heptyloxy-phenyl)amino]carbonyl]oxime;
benzaldehyde, O-[[(4-butoxy-phenyl)amino]carbonyl]oxime;
benzaldehyde, O-[[(4-hexyloxy-phenyl)amino]carbonyl]oxime;
propan-2-one, O-[[(4-heptyloxy-phenyl)amino]carbonyl]oxime;
pyridine-3-carbaldehyde, O-[[(4-hexyloxy-phenyl)amino]carbonyl]oxime; and
pyridine-3-carbaldehyde, O-[[(4-butoxy-phenyl)amino]carbonyl]oxime.

According to various embodiments of a third aspect of the present invention are provided compounds of Formula VII:

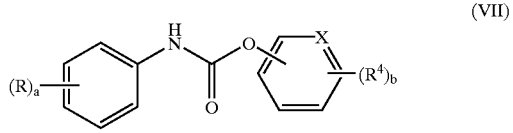

(VII)

or a pharmaceutically acceptable salt or solvate thereof, wherein
a is 1;
R is $C_{1-12}$ alkoxy;
$R^4$ is halo;
X is CH or nitrogen; and
b is 0 to 2,
with the proviso that when X is nitrogen then b is 0.

According to another embodiment of the third aspect of the present invention are provided compounds of Formula VI according to the first embodiment of the third aspect wherein X is CH and is a member selected from the group consisting of:
(4-undecyloxy-phenyl)-carbamic acid phenyl ester;
(4-decyloxy-phenyl)-carbamic acid phenyl ester;
(4-dodecyloxy-phenyl)-carbamic acid phenyl ester;
(4-octyloxy-phenyl)-carbamic acid 2-fluoro-phenyl ester;
(4-octyloxy-phenyl)-carbamic acid phenyl ester;
(4-heptyloxy-phenyl)-carbamic acid phenyl ester; and
(4-decyloxy-phenyl)-carbamic acid 2-fluoro-phenyl ester.

According to various embodiments of a fourth aspect of the present invention are provided compounds of Formula VIII

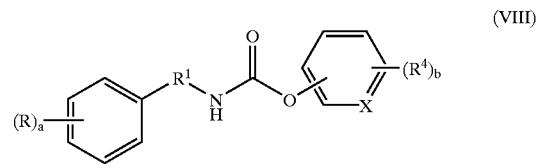

(VIII)

or a pharmaceutically acceptable salt or solvate thereof, wherein
a is 1;
R is $C_{1-12}$ alkoxy;
$R^1$ is a $C_{1-3}$ branched or linear aliphatic hydrocarbon;
$R^4$ is phenyl, $C_{1-3}$ alkoxy or halo;
X is CH or nitrogen; and
b is 2.

According to another embodiment of the fourth aspect of the present invention are provided compounds of Formula VIII according to the first embodiment of the fourth aspect wherein X is CH and is a member selected from the group consisting of:
(4-butoxy-benzyl)-carbamic acid 4-fluoro-phenyl ester;
pyridine-3-carbaldehyde, O-[[(4-butoxy-benzyl)amino]carbonyl]oxime;
(4-butoxy-benzyl)-carbamic acid phenyl ester;
[1-(4-butoxy-phenyl)-propyl]-carbamic acid 2-fluoro-phenyl ester;
(4-butoxy-benzyl)-carbamic acid 2,4-difluoro-phenyl ester;
(4-butoxy-benzyl)-carbamic acid 4-methoxy-phenyl ester;
[1-(4-butoxy-phenyl)-propyl]-carbamic acid 4-fluoro-phenyl ester;
(4-butoxy-benzyl)-carbamic acid 2-fluoro-phenyl ester; and
(4-butoxy-benzyl)-carbamic acid 3-chloro-phenyl ester.

According to various embodiments of a fifth aspect of the present invention are provided compounds of Formula IX:

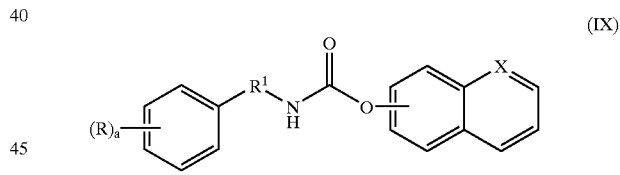

(IX)

or a pharmaceutically acceptable salt or solvate thereof, wherein
a is 1;
R is $C_{1-12}$ alkoxy;
$R^1$ is a $C_{1-3}$ branched or linear aliphatic hydrocarbon; and
X is CH or nitrogen.

According to another embodiment of the fifth aspect of the present invention are provided compounds of Formula IX according to the first embodiment of the fifth aspect wherein X is CH and is a member selected from the group consisting of:
(4-butoxy-benzyl)-carbamic acid quinolin-6-yl ester;
(4-butoxy-benzyl)-carbamic acid naphthalen-2-yl ester;
[1-(4-butoxy-phenyl)-propyl]-carbamic acid quinolin-6-yl ester; and
(4-butoxy-benzyl)-carbamic acid naphthalen-1-yl ester.

According to various embodiments of a sixth aspect of the present invention is provided a method of treating a condition or disorder by inhibiting fatty acid amidohydrolase in a mammal comprising administering to the mammal a therapeutically effective amount of a compound of Formula I or a compound having the structure

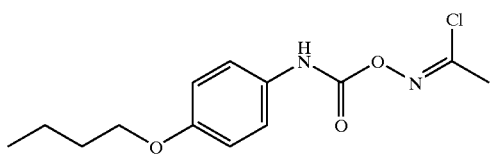

According to various embodiment of a seventh aspect of the present invention is provided a method of treating a condition or disorder by inhibiting fatty acid amidohydrolase in a mammal comprising administering to the mammal a therapeutically effective amount of a compound of Formula I.

According to various embodiments of a eighth aspect of the present invention is provided a method of treating neuropathic pain in a mammal comprising administering to the mammal a therapeutically effective amount of a compound of Formula I.

According to various embodiments of a ninth aspect of the present invention is provided a method of treating acute pain in a mammal comprising administering to the mammal a therapeutically effective amount of a compound of Formula I.

According to various embodiments of a tenth aspect of the present invention is provided a method of treating chronic pain in a mammal comprising administering to the mammal a therapeutically effective amount of a compound of Formula I.

According to various embodiments of an eleventh aspect of the present invention is provided a method of treating emesis in a mammal comprising administering to the mammal a therapeutically effective amount of a compound of Formula I.

According to various embodiments of a twelfth aspect of the present invention is provided a method of treating anxiety in a mammal comprising administering to the mammal a therapeutically effective amount of a compound of Formula I.

According to various embodiments of a thirteenth aspect of the present invention is provided a method of altering feeding behaviors in a mammal comprising administering to the mammal a therapeutically effective amount of a compound of Formula I.

According to various embodiments of a fourteenth aspect of the present invention is provided a method of treating movement disorders in a mammal comprising administering to the mammal a therapeutically effective amount of a compound of Formula I.

According to various embodiments of a fifteenth aspect of the present invention is provided a method treating glaucoma in a mammal comprising administering to the mammal a therapeutically effective amount of a compound of Formula I.

According to various embodiments of a sixteenth aspect of the present invention is provided a method of treating brain injury in a mammal comprising administering to the mammal a therapeutically effective amount of a compound of Formula I.

According to various embodiments of a seventeenth aspect of the present invention is provided a method of treating cardiovascular disease in a mammal comprising administering to the mammal a therapeutically effective amount of a compound of Formula I.

According to various embodiments of an eighteenth aspect of the present invention is provided a pharmaceutical composition for treating a condition or disorder requiring inhibition of a fatty acid amidohydrolase comprising a therapeutically effective amount of a compound of Formula I and a pharmaceutically acceptable carrier, adjuvant or diluent.

DETAILED DESCRIPTION OF THE INVENTION

Figure 1:
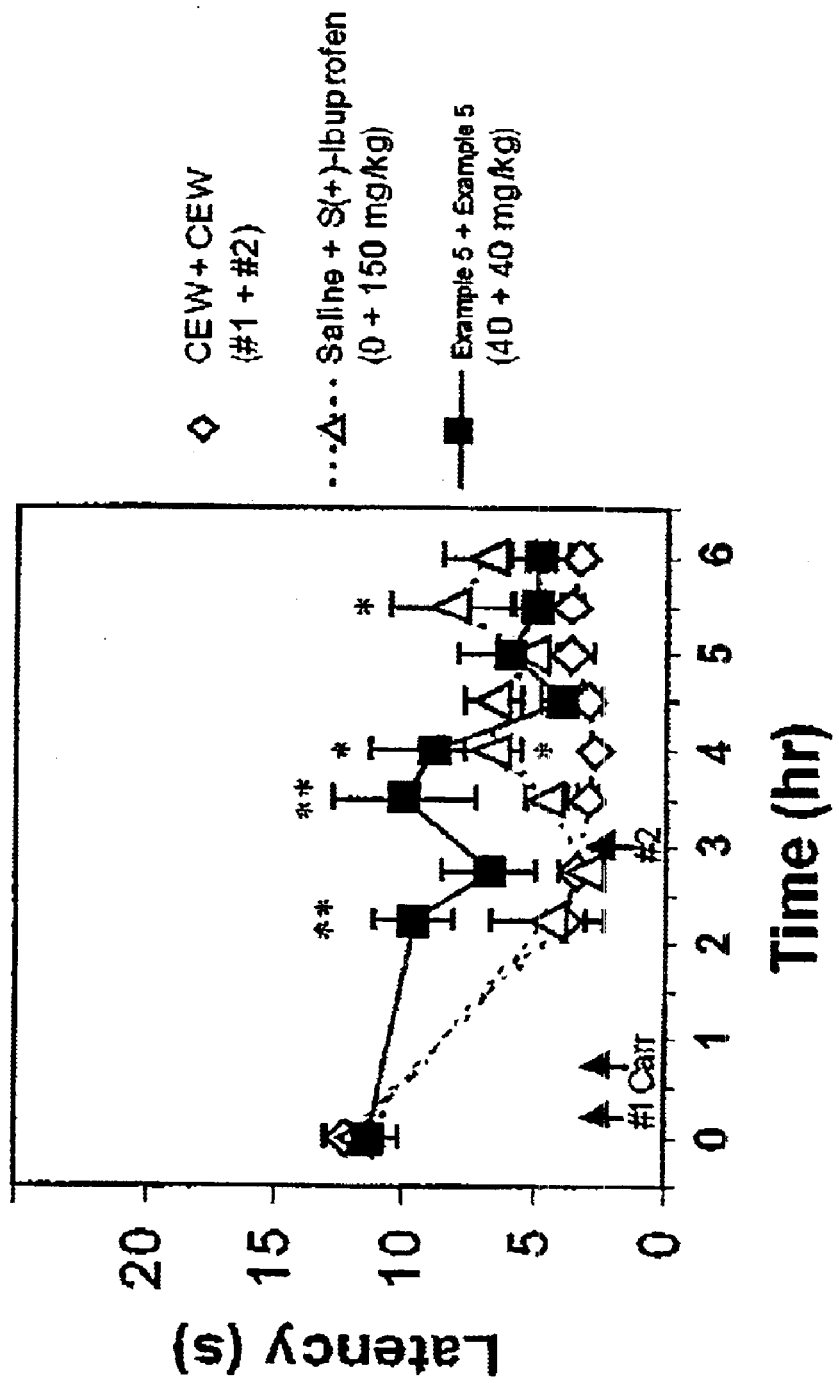
FIG. 1 illustrates results from a rat carrageen-induced thermal hypergesia model used for measuring chronic inflammatory pain.

The present invention provides a novel series of compounds of Formula I, its hydrates and solvates thereof:

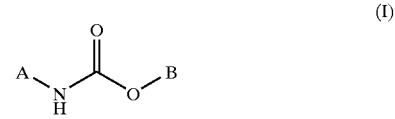

(I)

or a pharmaceutically acceptable salt or solvate thereof, wherein

A is dibenzofuranyl, dibenzothienyl, naphthyl, indolyl, fluorenyl, carbazolyl, or represented by Formula II:

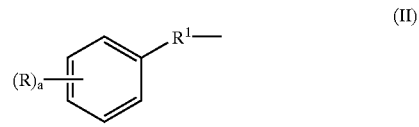

(II)

wherein a is 1 or 2,

R is $C_{1-16}$ alkoxy optionally substituted with phenyl, pyridyl or morpholinyl;

phenyl optionally substituted with $C_{1-4}$ alkyl; phenoxy; phenyl-$C_{1-4}$ alkyloxy-; pyridyloxy; pyridyl-$C_{1-4}$ alkyloxy-; —N(H)—C(O)—$C_{1-16}$ alkyl; or —C(O)—N(H)—$C_{1-16}$ alkyl;

$R^1$ is a bond or a $C_{1-3}$ branched or linear aliphatic hydrocarbon; and

B is $C_{1-4}$ alkyl, indolyl, benzofuranyl, benzothienyl, dibenzofuranyl, dibenzothienyl, fluorenyl, carbazolyl, napthyl, quinolinyl or isoquinolinyl, wherein each is optionally substituted with one or more of the same or different substituent selected from the group consisting of $C_{1-4}$ branched or linear aliphatic hydrocarbon, $C_{1-4}$ alkoxy, halo, haloalkyl, nitro and $(C_{1-3}$ alkyl$)_{0-2}$ amino- or represented by Formula III or Formula IV:

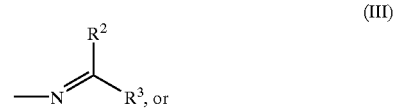

(III)

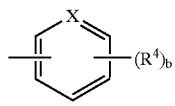

wherein
$R^2$ is hydrogen, methyl,
$R^3$ is $C_{1-4}$ alkyl, pyridyl, or phenyl optionally substituted with one or more of the same or different substituents selected from the group consisting of halo, $C_{1-4}$haloalkyl and nitro,
X is CH or nitrogen,
$R^4$ is $C_{1-4}$ branched or linear aliphatic hydrocarbon, $C_{1-4}$ alkoxy, halo, haloalkyl, nitro or amino, and
b is 0 to 3.

Preferably, A is represented by Formula II:

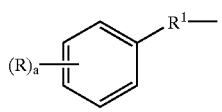

wherein a is 1, R is $C_{1-12}$ alkoxy; phenoxy; pyridyloxy; or amido optionally substituted with $C_{1-16}$ alkyl; and $R^1$ is a bond.

When B is represented by Formula III:

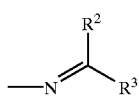

$R^2$ is preferably hydrogen or methyl, and $R^3$ is preferably methyl, or phenyl optionally substituted with one or more halo, haloalkyl or nitro.

When B is represented by Formula IV:

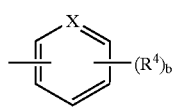

X is preferably CH, $R^4$ is preferably halo, and b is 1. When X is nitrogen, however, b is preferably 0.

When B is represented by Formula V:

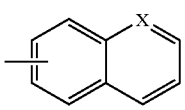

X is preferably nitrogen.

The description of the invention herein should be construed in congruity with the laws and principals of chemical bonding. For example, when a moiety is optionally substituted and said substitution requires the removal of a hydrogen atom from the moiety to be substituted, the description of the moiety should be read to include the moiety with or without said hydrogen atom. As another example, if a variable is defined as a particular moiety or atom and is further defined to have value of 0 or some integer, the bond(s) attaching said moiety should be suitably removed in the event the variable equals 0.

An embodiment or aspect which depends from another embodiment or aspect, will describe only the variables having values and provisos that differ from the embodiment or aspect from which it depends. For example, if a dependent embodiment describes a variable as being "phenyl or pyridyl", wherein said phenyl and pyridyl were described in the independent embodiment as being "optionally substituted", then the phenyl and pyridyl of the dependent embodiment will also be optionally substituted.

It is to be understood that the present invention may include any and all possible stereoisomers, geometric isomers, diastereoisomers, enantiomers, anomers and optical isomers, unless a particular description specifies otherwise. More particularly, the groups attached to the oxime portion of compounds of Formula (I), i.e., N=C, may assume transoid or cisoid configurations.

As used herein, "halo" or "halogen" includes fluoro, chloro, bromo and iodo.

As used herein, "alkyl" or "alkylene" includes straight or branched chain configurations.

The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level that will produce effective beneficial effects without causing any harmful or untoward side effects.

Compounds of the present invention may be synthesized according to the description provided below. Variables provided in the schema below are defined in accordance with the description of compounds of Formula (I) unless otherwise specified.

Experimentals

Scheme 1:

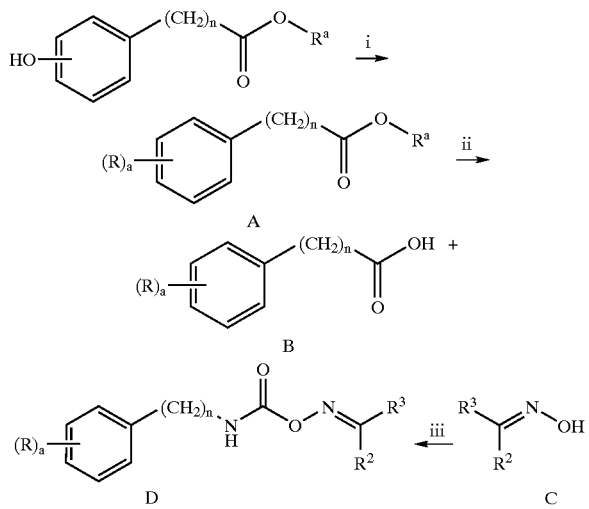

Scheme 1 Reaction conditions: (i) R-halide, NaH, DMF, room temp.; (ii) NaOH, EtOH, room temp., (iii) (a) N₃P(O)(OPh)₂, Et₃N, toluene at 105° C., (b) addition of oxime C at 80° C.; n is 0 to 3; R, R², R³, and B are as defined above.

Scheme 1A:

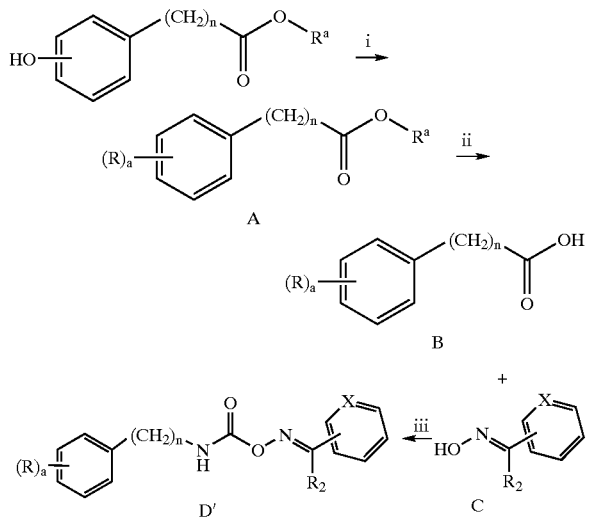

Scheme 1A Reaction conditions: (i) R-halide, NaH, DMF, room temp.; (ii) NaOH, EtOH, room temp., (iii) (a) N₃P(O)(OPh)₂, Et₃N, toluene at room temp., following by 90 min. at reflux, (b) addition of oxime C at room temp. with stirring for 1 hr., heating to 85° C., n is 0 to 3; R, and R² are as defined above.

Scheme 1B:

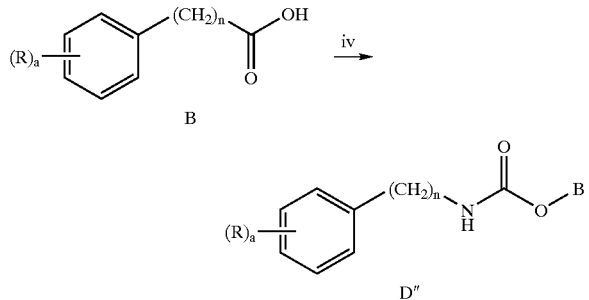

Scheme 1B Reaction conditions: (iv) (a) N₃P(O)(OPh)₂, Et₃N, toluene at 105° C., (b) B—OH at 80° C.; n is 0 to 3; R and B are as defined above.

The following Intermediates 1 to 39 may be used to synthesize Examples 1 to 124 in accordance with Schemes 1, 1A and 1B.

INTERMEDIATE 1

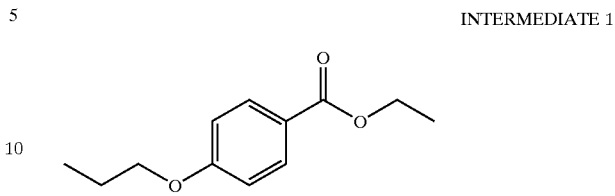

4-Propoxy-benzoic acid ethyl ester: (Scheme 1, Compound A) To a solution of ethyl 4-hydroxybenzoate (2.0 g, 12 mmol) and bromopropane (4.0 g, 32.8 mmol) in DMF (50 mL) was added NaH (60% in mineral oil, 0.80 g, 20.8 mmol). The resultant suspension was stirred at room temperature for 1.0 hour. The mixture was diluted with ethyl acetate (EtOAc) (300 mL), washed with $H_2O$, and then was dried over $Na_2SO_4$. After filtration and concentration in vacuo, the residue was purified by flash chromatography ($SiO_2$: EtOAc/Hexanes). This compound was obtained as a yellow oil (2.26 g, 10.9 mmol, 91% yield). $^1$H NMR (DMSO-$d_6$) δ 7.89 (d, 2H, J=8.7 Hz), 7.00 (d, 2H, J=9.0 Hz), 4.24 (q, 2H, J=6.9 Hz), 3.98 (t, 2H, J=6.6 Hz), 1.72 (m, 2H), 1.29 (t, 3H, J=6.6 Hz), 0.97 (t, 3H, J=7.2 Hz); Anal. Calcd for $C_{12}H_{16}O_3 \cdot 0.47C_6H_{14}$: C, 71.54; H, 9.14; N, 0.00. Found: C, 71.57; H, 8.78; N, 0.00; Mass Spec.: 209.04 (MH+).

INTERMEDIATE 2

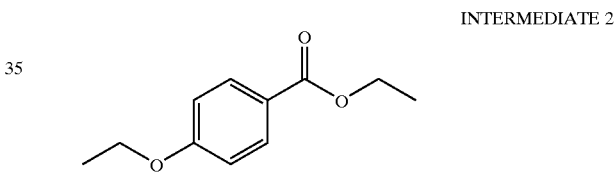

4-Ethoxy-benzoic acid ethyl ester: (Scheme 1, Compound A) Prepared as described for the example above. $^1$H NMR (DMSO-$d_6$) δ 7.89 (d, 2H, J=9.0 Hz), 7.00 (d, 2H, J=9.0 Hz), 4.24 (q, 2H, J=6.9 Hz), 4.08 (q, 2H, J=6.9 Hz), 1.31 (m, 6H); Anal. Calcd for $C_{11}H_{14}O_3 \cdot 0.47C_6H_{14}$: C, 70.71; H, 8.83; N, 0.00; Found: C, 71.10; H, 8.43; N, 0.00; Mass Spec.: 194.93 (MH+).

INTERMEDIATE 3

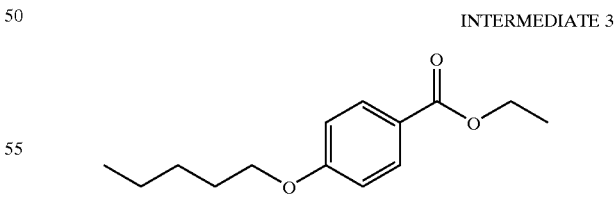

4-Pentyloxy-benzoic acid ethyl ester: (Scheme 1, Compound A) Prepared as described for the example above. $^1$H NMR (DMSO-$d_6$) δ 7.89 (d, 2H, J=8.7 Hz), 7.00 (d, 2H, J=9.0 Hz), 4.24 (q, 2H, J=6.9 Hz), 4.01 (t, 2H, J=6.6 Hz), 1.72 (m, 2H), 1.29 (m, 7H, J=6.6 Hz), 0.97 (t, 3H, J=7.2 Hz); Anal. Calcd for $C_{14}H_{20}O_3 \cdot 0.37C_6H_{14}$: C, 72.63; H, 9.46; N, 0.00; Found: C, 72.69; H, 9.12; N, 0.00; Mass Spec.: 237.11 (MH+).

INTERMEDIATE 4

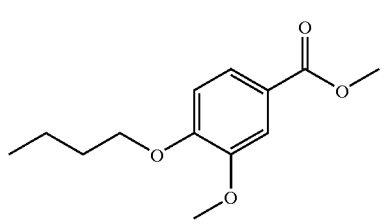

4-Butoxy-3-methoxy-benzoic acid methyl ester: (Scheme 1, Compound A) Prepared as described for the example above. $^1$H NMR (DMSO-d$_6$) δ 7.57 (dd, 1H, J=8.4, 1.8 Hz), 7.43 (d, 1H, J=1.8 Hz), 7.06 (d, 1H, J=8.4 Hz), 4.02 (q, 2H, J=6.6 Hz), 3.82 (s, 3H), 3.80 (s, 3H), 1.72 (m, 2H), 1.44 (m, 2H), 0.92 (t, 3H, J=7.5 Hz); Mass Spec.: 239.21 (MH+).

INTERMEDIATE 5

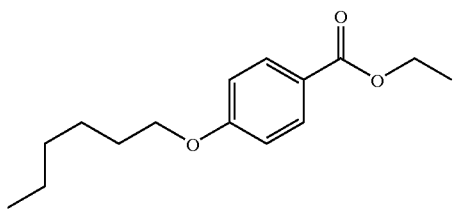

4-Hexyloxy-benzoic acid ethyl ester: (Scheme 1, Compound A) Prepared as described for the example above. $^1$H NMR (DMSO-$_{d6}$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 9H), 0.89 (t, 3H, J=7.2 Hz); Mass Spec.: 251 (MH+).

INTERMEDIATE 6

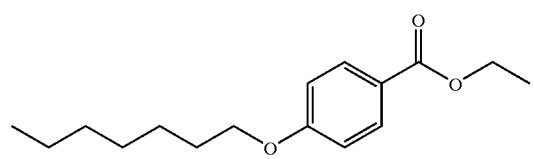

4-Heptyloxy-benzoic acid ethyl ester: (Scheme 1, Compound A) Prepared as described for the example above. $^1$H NMR (DMSO-d$_6$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 11H), 0.85 (t, 3H, J=7.2 Hz); Mass Spec.: 265 (MH+).

INTERMEDIATE 7

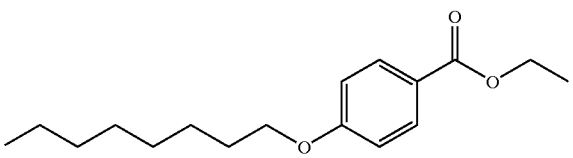

4-Octyloxy-benzoic acid ethyl ester: (Scheme 1, Compound A) Prepared as described for the example above. $^1$H NMR (DMSO-d$_6$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 13H), 0.84 (t, 3H, J=7.2 Hz); Mass Spec.: 279.36 (MH+).

INTERMEDIATE 8

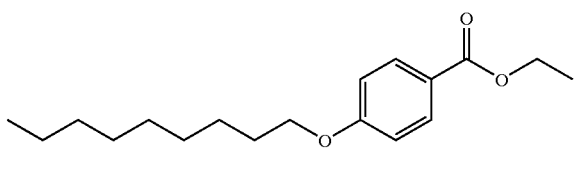

4-Nonyloxy-benzoic acid ethyl ester: (Scheme 1, Compound A) Prepared as described for the example above. $^1$H NMR (DMSO-d$_6$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 15H), 0.84 (t, 3H, J=7.2 Hz); Mass Spec.: 293.32 (MH+).

INTERMEDIATE 9

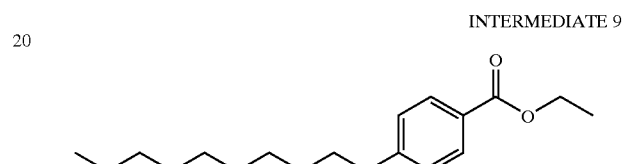

4-Decyloxy-benzoic acid ethyl ester: (Scheme 1, Compound A) Prepared as described for the example above. $^1$H NMR (DMSO-d$_6$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 17H), 0.83 (t, 3H, J=7.2 Hz); Mass Spec.: 307.27 (MH+).

INTERMEDIATE 10

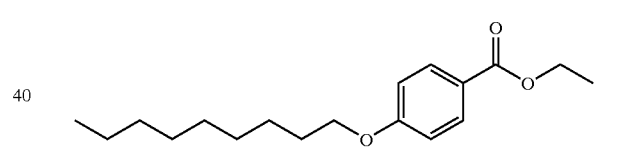

4-Undecyloxy-benzoic acid ethyl ester: (Scheme 1, Compound A) Prepared as described for the example above. $^1$H NMR (DMSO-d$_6$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 19H), 0.83 (t, 3H, J=7.2 Hz); Mass Spec.: 321.28 (MH+).

INTERMEDIATE 11

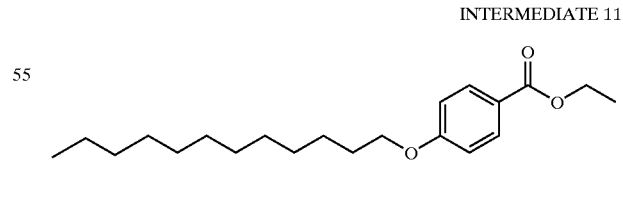

4-Dodecyloxy-benzoic acid ethyl ester: (Scheme 1, Compound A) Prepared as described for the example above. $^1$H NMR (DMSO-d$_6$) δ 7.89 (d, 2H, J=8.7 Hz), 7.00 (d, 2H, J=9.0 Hz), 4.26 (q, 2H, J=6.9 Hz), 4.01 (t, 2H, J=6.6 Hz), 1.72 (m, 2H), 1.29 (m, 21H), 0.83 (t, 3H, J=6.6 Hz); Mass Spec.: 335.29 (MH+).

INTERMEDIATE 12

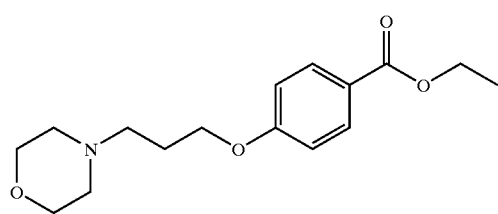

4-(3-Morpholin-4-yl-propoxy)-benzoic acid ethyl ester: (Scheme 1, Compound A) Prepared as described for the example above. $^1$H NMR (DMSO-$d_6$) δ 7.89 (d, 2H, J=8.7 Hz), 7.00 (d, 2H, J=9.0 Hz), 4.26 (q, 2H, J=6.9 Hz), 4.08 (t, 2H, J=6.6 Hz), 3.56 (t, 4H, J=4.5 Hz), 2.36 (m, 6H), 1.72 (m, 2H), 1.32 (m, 2H), 1.29 (t, 3H, J=6.9 Hz); Mass Spec.: 294.32 (MH+).

INTERMEDIATE 13

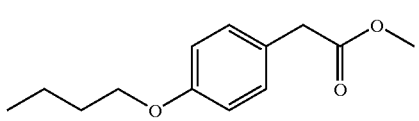

(4-Butoxy-phenyl)-acetic acid methyl ester: (Scheme 1, Compound A) Prepared as described for the example above. $^1$H NMR (DMSO-$d_6$) δ 7.16 (dd, 2H, J=6.6, 1.8 Hz), 6.85 (dd, 2H, J=6.6, 1.8 Hz), 3.93 (t, 2H, J=6.3 Hz), 3.59 and 3.58 (5H, CH$_2$, CH$_3$), 1.67 (m, 2H), 1.40 (m, 2H), 0.92 (t, 3H, J=7.2 Hz).

INTERMEDIATE 14

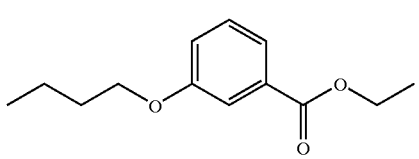

3-Butoxy-benzoic acid ethyl ester: (Scheme 1, Compound A) Prepared as described for the example above. $^1$H NMR (DMSO-$d_6$) δ 7.53 (dd, 1H, J=7.8, 1.5 Hz), 7.42 (m, 2H), 7.20 (dd, 1H, J=8.4, 1.5 Hz), 4.31 (q, 2H, J=6.9 Hz), 4.01 (t, 2H, J=6.6 Hz), 1.72 (m, 2H), 1.47 (m, 2H), 1.32 (t, 3H, J=6.9 Hz), 0.93 (t, 3H, J=7.5 Hz); Mass Spec.: 223.24 (MH+).

INTERMEDIATE 15

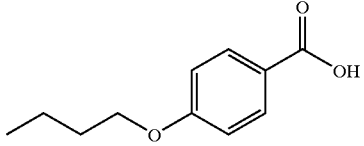

4-Butoxy-benzoic acid: (Scheme 1, Compound B) To a solution of ethyl 4-butoxybenzoate (2.0 g, 9.6 mmol) in EtOH (30 mL) was added NaOH (10 N, 6 mL, 60 mmol). The resulting mixture was stirred at room temperature for 3 hours, diluted with H$_2$O (30 mL), acidified to about pH 1.0 using HCl (6N). The precipitates were filtered off by filter paper, washed by H$_2$O and hexanes. This compound was obtained as a white solid. (1.63 g, 9.1 mmol, 94% yield). $^1$H NMR (DMSO-$d_6$) δ 12.59 (br. s, 1H), 7.88 (d, 2H, J=9.5 Hz), 6.97 (d, 2H, J=9.5 Hz), 4.01 (t, 2H, J=6.5 Hz), 1.68 (m, 2H), 1.42 (m, 2H), 0.91 (t, 3H, J=6.5 Hz); $^{13}$C NMR (DMSO): 166.9, 162.2, 131.2, 122.7, 114.0, 67.3, 30.5, 18.6 and 13.5; Mass Spec.: 195.17 (MH+).

INTERMEDIATE 16

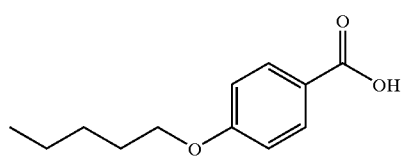

4-Pentyloxy-benzoic acid: (Scheme 1, Compound B) Prepared as described for the example above. $^1$H NMR (DMSO-$d_6$) δ 12.59 (br, s, 1H), 7.88 (d, 2H, J=9.6 Hz), 6.97 (d, 2H, J=9.6 Hz), 4.01 (t, 2H, J=6.9 Hz), 1.69 (m, 2H), 1.32 (m, 4H), 0.89 (t, 3H, J=6.9 Hz); Mass Spec.: 209.23 (MH+).

INTERMEDIATE 17

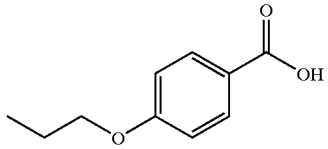

4-Propoxy-benzoic acid: (Scheme 1, Compound B) Prepared as described for the example above. $^1$H NMR (DMSO-$d_6$) δ 12.6 (br, s, 1H), 7.88 (d, 2H, J=9.6 Hz), 6.97 (d, 2H, J=9.6 Hz), 4.01 (t, 2H, J=6.9 Hz), 1.72 (m, 2H), 0.97 (t, 3H, J=7.5 Hz); Mass Spec.: 181.18 (MH+).

INTERMEDIATE 18

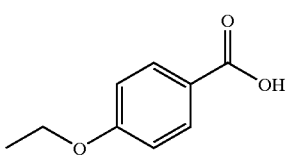

4-Ethoxy-benzoic acid: (Scheme 1, Compound B) Prepared as described for the example above. $^1$H NMR (DMSO-$d_6$) δ 12.59 (br. s, 1H), 7.88 (d, 2H, J=9.6 Hz), 6.97 (d, 2H, J=9.6 Hz), 4.08 (q, 2H, J=7.2 Hz), 1.33 (t, 3H, J=6.9 Hz); Mass Spec.: 167.13 (MH+).

INTERMEDIATE 19

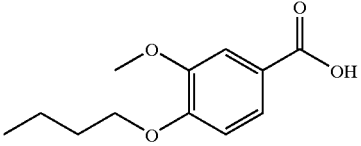

4-Butoxy-3-methoxy-benzoic acid: (Scheme 1, Compound B) Prepared as described for the example above. $^1$H NMR (DMSO-$d_6$) δ 12.6 (br, s, 1H), 7.54 (dd, 1H, J=8.4, 1.8 Hz), 7.43 (d, 1H, J=1.8 Hz), 7.06 (d, 1H, J=8.4 Hz), 4.02 (q, 2H, J=6.6 Hz), 3.80 (s, 3H), 1.72 (m, 2H), 1.44 (m, 2H), 0.92 (t, 3H, J=7.5 Hz).

INTERMEDIATE 20

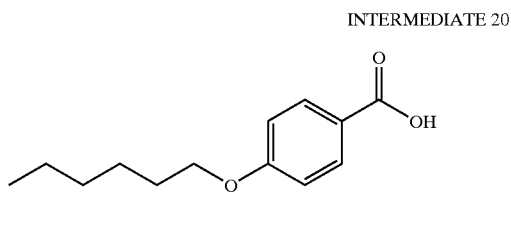

4-Hexyloxy-benzoic acid: (Scheme 1, Compound B) Prepared as described for the example above. $^1$H NMR (DMSO-d$_6$) δ 12.59 (s, 1H), 7.89 (d, 2H, J=8.7 Hz), 7.00 (d, 2H, J=9.0 Hz), 4.01 (t, 2H, J=6.6 Hz), 1.72 (m, 2H), 1.29 (m, 6H), 0.89 (t, 3H, J=7.2 Hz); Mass Spec.: 223 (MH+).

INTERMEDIATE 21

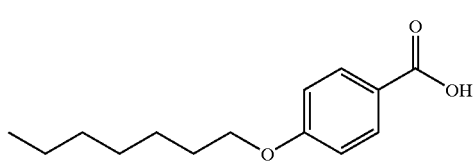

4-Heptyloxy-benzoic acid: (Scheme 1, Compound B) Prepared as described for the example above. $^1$H NMR (DMSO-d$_6$) δ 12.59 (s, 1H), 7.89 (d, 2H, J=8.7 Hz), 7.00 (d, 2H, J=9.0 Hz), 4.01 (t, 2H, J=6.6 Hz), 1.72 (m, 2H), 1.29 (m, 8H), 0.85 (t, 3H, J=7.2 Hz); Mass Spec.: 237.16 (MH+).

INTERMEDIATE 22

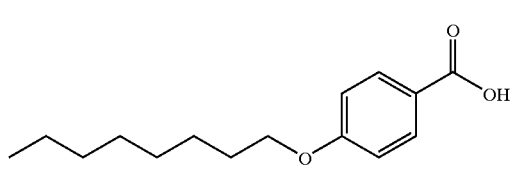

4-Octyloxy-benzoic acid: (Scheme 1, Compound B) Prepared as described for the example above. $^1$H NMR (DMSO-d$_6$) δ 7.89 (d, 2H, J=8.7 Hz), 7.00 (d, 2H, J=9.0 Hz), 4.01 (t, 2H, J=6.6 Hz), 1.72 (m, 2H), 1.29 (m, 10H), 0.84 (t, 3H, J=7.2 Hz); Mass Spec.: 251.11 (MH+).

INTERMEDIATE 23

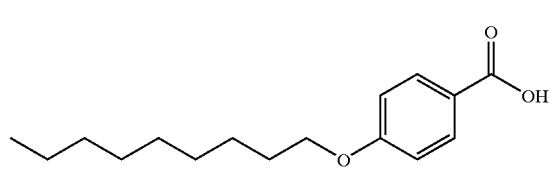

4-Nonyloxy-benzoic acid: (Scheme 1, Compound B) Prepared as described for the example above. $^1$H NMR (DMSO-d$_6$) δ 12.58 (s, 1H), 7.89 (d, 2H, J=8.7 Hz), 7.00 (d, 2H, J=9.0 Hz), 4.01 (t, 2H, J=6.6 Hz), 1.72 (m, 2H), 1.29 (m, 12H), 0.84 (t, 3H, J=7.2 Hz).

INTERMEDIATE 24

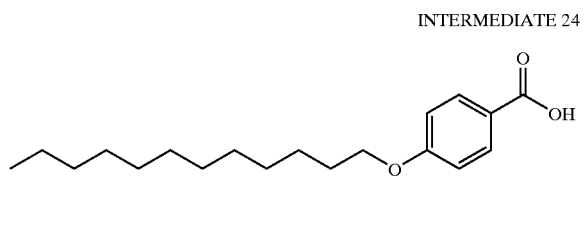

4-Dodecyloxy-benzoic acid: (Scheme 1, Compound B) Prepared as described for the example above. $^1$H NMR (DMSO-d$_6$) δ 12.6 (s, 1H), 7.86 (d, 2H, J=8.7 Hz), 7.00 (d, 2H, J=9.0 Hz), 4.01 (t, 2H, J=6.6 Hz), 1.72 (m, 2H), 1.29 (m, 18H), 0.84 (t, 3H, J=6.6 Hz).

INTERMEDIATE 25

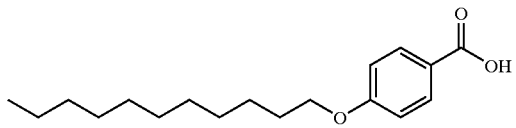

4-Undecyloxy-benzoic acid: (Scheme 1, Compound B) Prepared as described for the example above. $^1$H NMR (DMSO-d$_6$) δ 12.6 (s, 1H), 7.86 (d, 2H, J=8.7 Hz), 7.00 (d, 2H, J=9.0 Hz), 4.01 (t, 2H, J=6.6 Hz), 1.72 (m, 2H), 1.29 (m, 16H), 0.84 (t, 3H, J=6.6 Hz).

IINTERMEDIATE 26

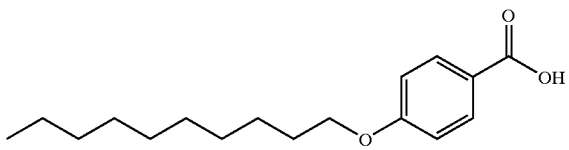

4-Decyloxy-benzoic acid: (Scheme 1, Compound B) Prepared as described for the example above. $^1$H NMR (DMSO-d$_6$) δ 12.6 (s, 1H), 7.86 (d, 2H, J=8.7 Hz), 7.00 (d, 2H, J=9.0 Hz), 4.01 (t, 2H, J=6.6 Hz), 1.72 (m, 2H), 1.29 (m, 14H), 0.84 (t, 3H, J=6.6 Hz).

INTERMEDIATE 27

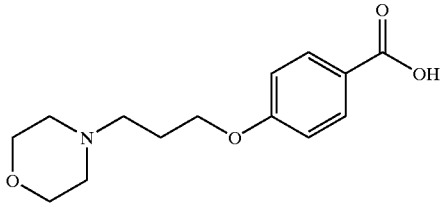

4-(3-Morpholin-4-yl-propoxy)-benzoic acid: (Scheme 1, Compound B) Prepared as described for the example above. $^1$H NMR (DMSO-d$_6$) δ 7.78 (d, 2H, J=8.4 Hz), 6.79 (d, 2H, J=8.4 Hz), 4.08 (t, 2H, J=6.6 Hz), 3.56 (t, 4H, J=4.5 Hz), 2.36 (m, 6H), 1.85 (m, 2H).

INTERMEDIATE 28

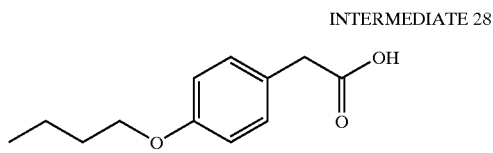

(4-Butoxy-phenyl)-acetic acid: (Scheme 1, Compound B) Prepared as described for the example above. $^1$H NMR (DMSO-$d_6$) δ 12.21 (br. s, 1H), 7.16 (dd, 2H, J=6.6, 1.8 Hz), 6.85 (dd, 2H, J=6.6, 1.8 Hz), 3.93 (t, 2H, J=6.3 Hz), 3.46 (s, 2H), 1.69 (m, 2H), 1.43 (m, 2H), 0.92 (t, 3H, J=7.2 Hz).

INTERMEDIATE 29

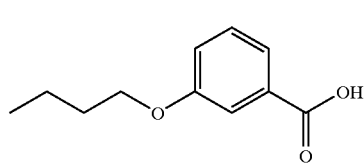

3-Butoxy-benzoic acid: (Scheme 1, Compound B) Prepared as described for the example above. $^1$H NMR (DMSO-$d_6$) δ 7.53 (dd, 1H, J=7.8, 1.5 Hz), 7.42 (m, 2H), 7.17 (dd, 1H, J=8.4, 1.5 Hz), 4.01 (t, 2H, J=6.6 Hz), 1.72 (m, 2H), 1.47 (m, 2H), 0.93 (t, 3H, J=7.2 Hz).

INTERMEDIATE 30

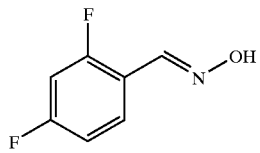

2,4-Difluoro-benzaldehyde oxime: (Scheme 1, Compound C) To a mixture of 2,4-difluorobenzaldehyde (0.80 g, 5.6 mmol) and hydroxyamine HCl salt (0.43 g, 6.2 mmol) in EtOH (5 mL) was added $K_2CO_3$ (0.85 g, 6.2 mmol). The resultant mixture was stirred at rt for 24 hours. The mixture was diluted with MeOH (20 mL). The precipitates were filter off and washed with MeOH. The product from filtrate was purified by recrystalization (EtOAc/Hexanes). This compound was obtained as a white solid (0.84 g, 5.3 mmol, 94% yield). $^1$H NMR (DMSO-$d_6$) δ 12.98 (br. s, 1H), 8.17 (s, 1H), 7.79 (m, 1H), 7.32 (m, 1H), 7.11 (m, 1H); Analytical HPLC 1.03 min. (95%); Mass Spec.: 158.06 (MH+).

INTERMEDIATE 31

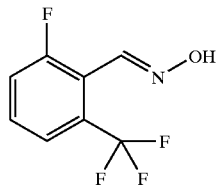

2-Fluoro-6-trifluoromethyl-benzaldehyde oxime: (Scheme 1, Compound C) Prepared as described for the example above. $^1$H NMR (DMSO-$d_6$) δ 11.96 (br. s, 1H), 8.21 (m, 1H), 7.65 (m, 3H); Analytical HPLC 1.20 min. (96%); Mass Spec.: 208.14 (MH+).

INTERMEDIATE 32

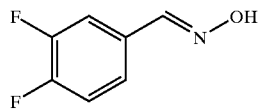

3,4-Difluoro-benzaldehyde oxime: (Scheme 1, Compound C) Prepared as described for the example above. Analytical HPLC 1.00 min. (92%); Mass Spec.: 158 (MH+).

INTERMEDIATE 33

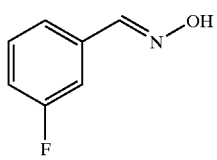

3-Fluoro-benzaldehyde oxime: (Scheme 1, Compound C) Prepared as described for the example above. Analytical HPLC 0.90 min. (95%); Mass Spec.: 138 (MH−).

INTERMEDIATE 34

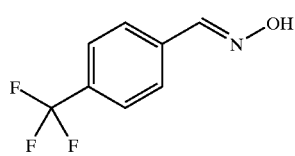

4-Trifluoromethyl-benzaldehyde oxime: (Scheme 1, Compound C) Prepared as described for the example above. Analytical HPLC 1.31 min. (95%); Mass Spec.: 188.01 (MH+).

INTERMEDIATE 35

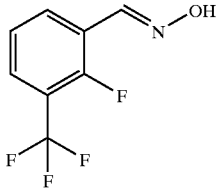

2-Fluoro-3-trifluoromethyl-benzaldehyde oxime: (Scheme 1, Compound C) Prepared as described for the example above. Analytical HPLC 1.41 min. (90%); Mass Spec.: 206.00 (MH−).

INTERMEDIATE 36

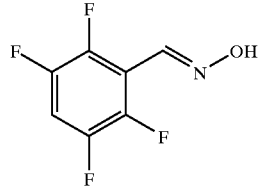

2,3,5,6-Tetrafluoro-benzaldehyde oxime: (Scheme 1, Compound C) Prepared as described for the example above. Analytical HPLC 0.83 min. (96%); Mass Spec.: 191.98 (MH−).

INTERMEDIATE 37

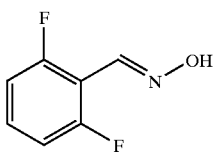

2,6-Difluoro-benzaldehyde oxime: (Scheme 1, Compound C) Prepared as described for the example above. Analytical HPLC 0.86 min. (95%); Mass Spec.: 158.05 (MH+).

INTERMEDIATE 38

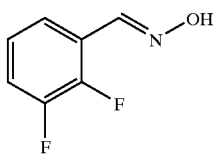

2,3-Difluoro-benzaldehyde oxime: (Scheme 1, Compound C) Prepared as described for the example above. Analytical HPLC 0.83 min. (90%); Mass Spec.: 156.04 (MH−).

INTERMEDIATE 39

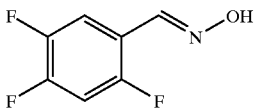

2,4,5-Trifluoro-benzaldehyde oxime: (Scheme 1, Compound C) Prepared as described for the example above. Analytical HPLC 0.89 min. (91%); Mass Spec.: 174.00 (MH−).

EXAMPLE 1

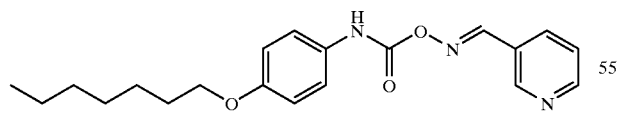

3-Pyridinecarboxaldehyde, O-[[[4-(Heptyloxy)phenyl]amino]carbonyl]oxime (Scheme 1, Compound D) To a solution of 4-heptyloxybenzoic acid (0.20 g, 0.85 mmol) and Et$_3$N (0.18 g, 1.8 mmol) in toluene (5 mL) was added diphenylphosphoryl azide (0.322 g, 1.2 mmol). The resultant mixture was stirred at r.t. for 10 min. and then at 105° C. under N$_2$ for 60 min. After the mixture was cooled to r.t., 3-pyridinealdoxime (0.20 g, 1.7 mmol) was added. The reaction mixture was stirred at r.t. for 10 min. and then at 80° C. for 1 h. The product (free base) was purified by flash chromatography (SiO$_2$: EtOAc/Hexanes) and then was dissolved in a solution of TFA in THF (5.0 mg/mL, 17.8 mL, 0.78 mmol). Removal of solvent provided this compound (TFA salt) as a pale yellow solid (0.244 g, 0.52 mmol, 61% yield). $^1$H NMR (DMSO-d$_6$) δ 9.72 (s, 1H), 8.99 (s, 1H), 8.72 (m, 2H), 8.32 (d, 1H, J=9.0 Hz), 7.56 (m, 1H), 7.40 (d, 2H, J=8.5 Hz), 6.91 (d, 2H, J=6.5 Hz), 3.92 (t, 2H, J=6.5 Hz), 1.72 (m, 2H), 1.32 (m, 8H), 0.87 (t, 3H, J=7.0 Hz); Anal. Calcd for C$_{20}$H$_{25}$N$_3$O$_3$·0.98C$_2$F$_3$O$_2$H$_1$: C, 56.44; H, 5.60; N, 8.99. Found: C, 56.41; H, 5.64; N, 8.94. Mass Spec: 356.28 (MH$^+$).

EXAMPLE 2

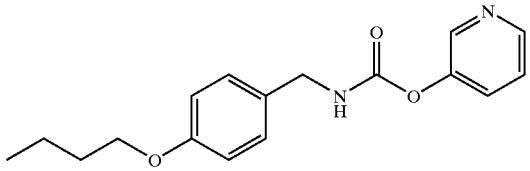

(4-Butoxyphenyl)methylcarbamic acid, 3-pyridinyl ester (Scheme 1, Compound D) Prepared as described for the example above. $^1$H NMR (DMSO-d$_6$) δ 8.51 (m, 3H), 7.75 (m, 1H), 7.55 (m, 1H), 7.24 (d, 2H, J=9.0 Hz), 6.91 (d, 2H, J=8.7 Hz), 4.22 (d, 2H, J=6.0), 3.92 (t, 2H, J=6.6 Hz), 1.70 (m, 2H), 1.36 (m, 2H), 0.92 (t, 3H, J=7.5 Hz); Anal. Calcd for C$_{17}$H$_{20}$N$_2$O$_3$·1.55C$_2$F$_3$O$_2$H$_1$: C, 50.64; H, 4.56; N, 5.88. Found: C, 50.49; H, 4.58; N, 5.73. Mass Spec: 301.17 (MH$^+$).

EXAMPLE 3

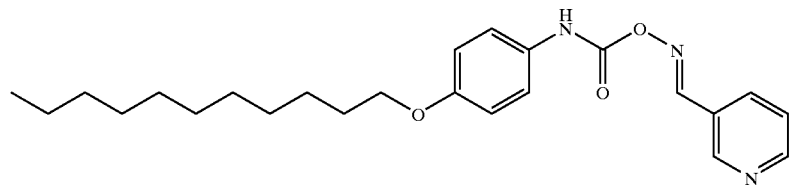

3-Pyridinecarboxaldehyde, O-[[[4-(undecyloxy)phenyl]amino]carbonyl]oxime (Scheme 1, Compound D) Prepared as described for the example above. $^1$H NMR (DMSO-d$_6$) δ 9.72 (s, 1H), 8.99 (s, 1H), 8.72 (m, 2H), 8.32 (d, 1H, J=9.0 Hz), 7.56 (m, 1H), 7.40 (d, 2H, J=8.5 Hz), 6.91 (d, 2H, J=6.5 Hz), 3.92 (t, 2H, J=6.5 Hz), 1.72 (m, 2H), 1.32 (m, 16H), 0.87 (t, 3H, J=7.0 Hz). Mass Spec: 412.33 (MH$^+$).

EXAMPLE 4

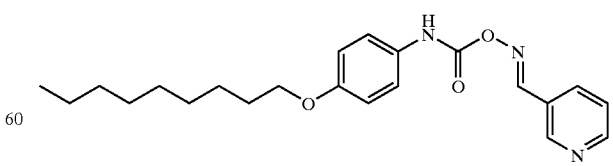

3-Pyridinecarboxaldehyde, O-[[[4-(nonyloxy)phenyl]amino]carbonyl]oxime (Scheme 1, Compound D) Prepared as described for the example above. $^1$H NMR (DMSO-d$_6$) δ 9.72 (s, 1H), 8.99 (s, 1H), 8.72 (m, 2H), 8.32 (d, 1H, J=9.0

Hz), 7.56 (m, 1H), 7.40 (d, 2H, J=8.5 Hz), 6.91 (d, 2H, J=6.5 Hz), 3.92 (t, 2H, J=6.5 Hz), 1.72 (m, 2H), 1.32 (m, 12H), 0.87 (t, 3H, J=7.0 Hz). Mass Spec: 384.89 (MH+).

EXAMPLE 5

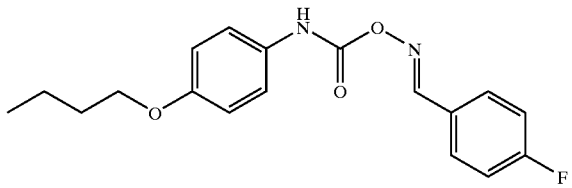

4-Fluorobenzaldehyde, O-[[(4-butoxyphenyl)amino]carbonyl]oxime (Scheme 1, Compound D) Prepared as described for the example above in a form of free base. No trifluoroacetic acid was used. $^1$H NMR (DMSO-d$_6$) δ 9.66 (s, 1H), 8.64 (s, 1H), 7.90 (m, 2H), 7.38 (m, 2H), 7.34 (t, 2H, J=6.0 Hz), 6.92 (d, 2H, J=4.5 Hz), 3.92 (t, 2H, J=6.5 Hz), 1.72 (m, 2H), 1.40 (m, 2H), 0.92 (t, 3H, J=7.5 Hz); Anal. Calcd for C$_{18}$H$_{19}$FN$_2$O$_3$: C, 65.44; H, 5.79; N, 8.48. Found: C, 65.48; H, 5.88; N, 8.46. Mass Spec: 331.14 (MH+).

EXAMPLE 6

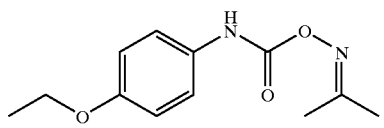

2-Propanone, O-[[(4-ethoxyphenyl)amino]carbonyl]oxime (Scheme 1, Compound D) Prepared as described for the example above. This compound was purified by preparative HPLC (YMC 30×100 mm (5 uM packing), 10% MeOH/90% water/01% TFA as mobile phase A, 90% MeOH/10%water/0.1% TFA as mobile phase B). Analytical HPLC 1.10 min. (95%). Mass Spec: 237 (MH+).

EXAMPLE 7

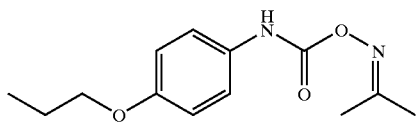

2-Propanone, O-[[(4-propoxyphenyl)amino]carbonyl]oxime (Scheme 1, Compound D) Prepared as described for the example above. $^1$H NMR (DMSO-d$_6$) δ 9.36 (s, 1H), 7.34 (d, 2H, J=9.0 Hz), 6.85 (dd, 2H, J=6.9, 2.1 Hz), 3.87 (t, 2H, J=6.9 Hz), 1.97 (s, 6H), 1.72 (m, 2H), 0.96 (t, 3H, J=7.5 Hz); Analytical HPLC 1.27 min. (95%). Mass Spec: 251.24 (MH+).

EXAMPLE 8

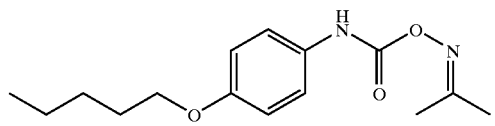

2-Propanone, O-[[(4-pentyloxyphenyl)amino]carbonyl]oxime (Scheme 1, Compound D) Prepared as described for the example above. Analytical HPLC 1.67 min. (95%). Mass Spec: 279.18 (MH+).

EXAMPLE 9

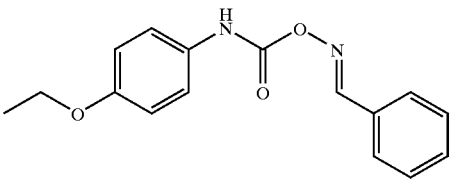

Benzaldehyde, O-[[(4-ethoxyphenyl)amino]carbonyl]oxime (Scheme 1, Compound D) Prepared as described for the example above. Analytical HPLC 1.41 min. (85%). Mass Spec: 285.21 (MH+).

EXAMPLE 10

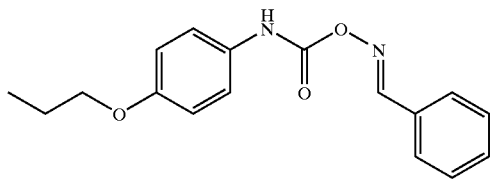

Benzaldehyde, O-[[(4-propoxyphenyl)amino]carbonyl]oxime (Scheme 1, Compound D) Prepared as described for the example above. Analytical HPLC 1.64 min. (85%). Mass Spec: 299.15 (MH+).

EXAMPLE 11

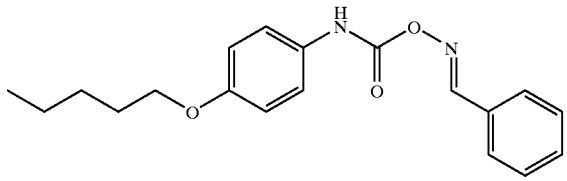

Benzaldehyde, O-[[(4-pentyloxyphenyl)amino]carbonyl]oxime (Scheme 1, Compound D) Prepared as described for the example above. Analytical HPLC 1.85 min. (95%). Mass Spec: 327.20 (MH+).

EXAMPLE 12

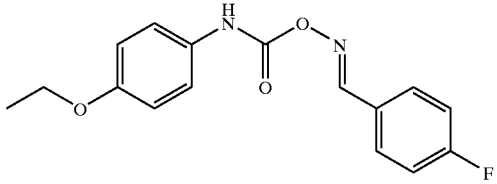

4-Fluorobenzaldehyde, O-[[(4-ethoxyphenyl)amino]carbonyl]oxime (Scheme 1, Compound D) Prepared as described for the example above. $^1$H NMR (DMSO-d$_6$) δ 9.66 (s, 1H), 8.64 (s, 1H), 7.90 (m, 2H), 7.38 (m, 4H), 6.90 (d, 2H, J=4.5 Hz), 3.92 (q, 2H, J=6.5 Hz), 1.31 (t, 3H, J=7.2 Hz). Analytical HPLC 1.46 min. (95%). Mass Spec: 303 (MH+).

EXAMPLE 13

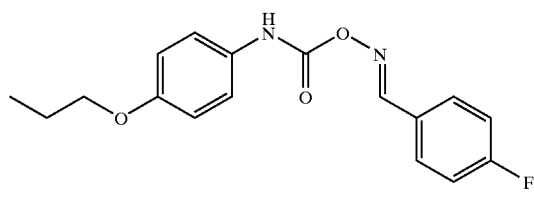

4-Fluorobenzaldehyde, O-[[(4-propoxyphenyl)amino]carbonyl]oxime (Scheme 1, Compound D) Prepared as described for the example above. Analytical HPLC 1.67 min. (94%). Mass Spec: 317 (MH+).

EXAMPLE 14

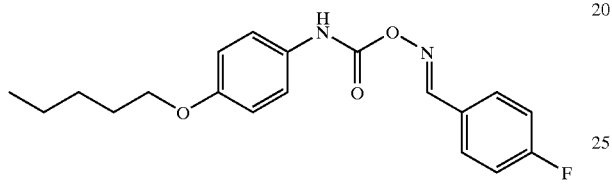

4-Fluorobenzaldehyde, O-[[(4-pentyloxyphenyl)amino]carbonyl]oxime (Scheme 1, Compound D) Prepared as described for the example above. Analytical HPLC 1.76 min. (97%). Mass Spec: 345.24 (MH+).

EXAMPLE 15

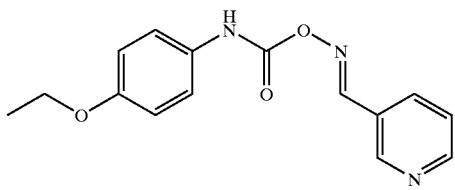

3-Pyridinecarboxaldehyde, O-[[(4-ethoxyphenyl)amino]carbonyl]oxime (Scheme 1, Compound D) Prepared as described for the example above. Analytical HPLC 0.99 min. (95%). Mass Spec: 286.24 (MH+).

EXAMPLE 16

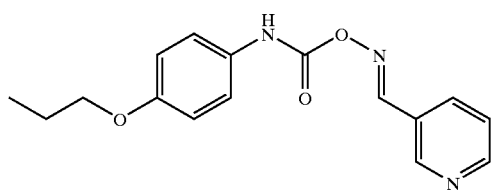

3-Pyridinecarboxaldehyde, O-[[(4-propoxyphenyl)amino]carbonyl]oxime (Scheme 1, Compound D) Prepared as described for the example above. Analytical HPLC 1.28 min. (95%). Mass Spec: 300.15 (MH+).

EXAMPLE 17

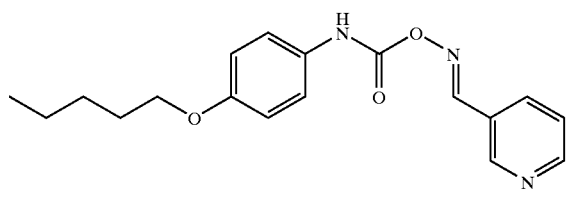

3-Pyridinecarboxaldehyde, O-[[(4-pentyloxyphenyl)amino]carbonyl]oxime (Scheme 1, Compound D) Prepared as described for the example above. Analytical HPLC 1.50 min. (95%). Mass Spec: 328.27 (MH+).

EXAMPLE 18

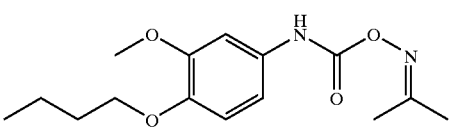

2-Propanone, O-[[(4-butoxy-3-methoxyphenyl)amino]carbonyl]oxime (Scheme 1, Compound D) Prepared as described for the example above. Analytical HPLC 1.35 min. (98%). Mass Spec: 295.27 (MH+).

EXAMPLE 19

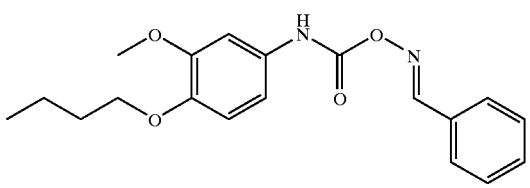

Benzaldehyde, O-[[(4-butoxy-3-methoxyphenyl)amino]carbonyl]oxime (Scheme 1, Compound D) Prepared as described for the example above. Analytical HPLC 1.59 min. (99%). Mass Spec: 343 (MH+).

EXAMPLE 20

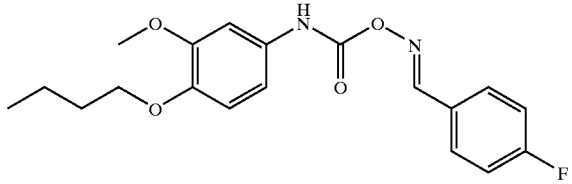

4-Fluorobenzaldehyde, O-[[(4-butoxy-3-methoxyphenyl)amino]carbonyl]oxime (Scheme 1, Compound D) Prepared as described for the example above. Analytical HPLC 1.61 min. (95%). Mass Spec: 361.24 (MH+).

EXAMPLE 21

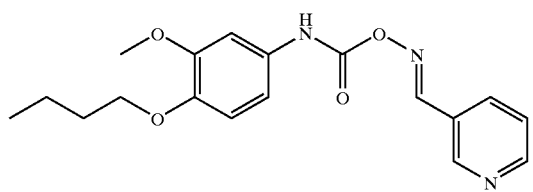

3-Pyridinecarboxaldehyde, O-[[(4-butoxy-3-methoxyphenyl)amino]carbonyl]oxime (Scheme 1, Compound D) Prepared as described for the example above. Analytical HPLC 1.27 min. (99%). Mass Spec: 344.30 (MH+).

EXAMPLE 22

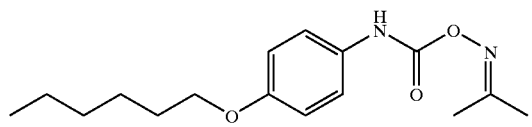

2-Propanone, O-[[(4-hexyloxyphenyl)amino]carbonyl]oxime (Scheme 1, Compound D) Prepared as described for the example above. Analytical HPLC 1.70 min. (94%). Mass Spec: 293 (MH+).

EXAMPLE 23

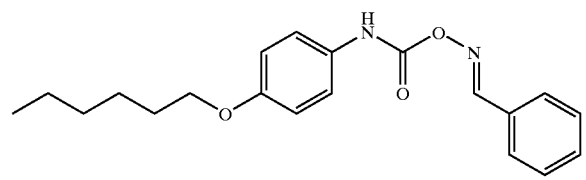

Benzaldehyde, O-[[(4-hexyloxyphenyl)amino]carbonyl]oxime (Scheme 1, Compound D) Prepared as described for the example above. Analytical HPLC 1.84 min. (99%). Mass Spec: 341.26 (MH+).

EXAMPLE 24

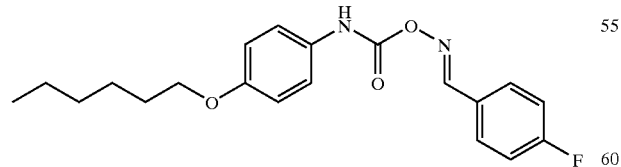

4-Fluorobenzaldehyde, O-[[(4-hexyloxyphenyl)amino]carbonyl]oxime (Scheme 1, Compound D) Prepared as described for the example above. Analytical HPLC 1.86 min. (99%). Mass Spec: 359.22 (MH+).

EXAMPLE 25

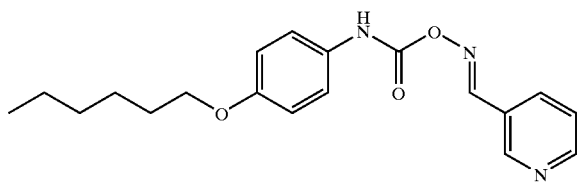

3-Pyridinecarboxaldehyde, O-[[(4-hexyloxyphenyl)amino]carbonyl]oxime (Scheme 1, Compound D) Prepared as described for the example above. Analytical HPLC 1.64 min. (90%). Mass Spec: 342.30 (MH+).

EXAMPLE 26

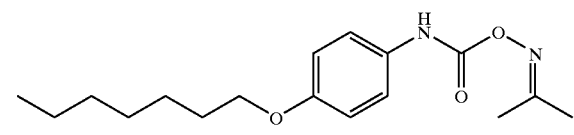

2-Propanone, O-[[(4-heptyloxyphenyl)amino]carbonyl]oxime (Scheme 1, Compound D) Prepared as described for the example above. Analytical HPLC 1.98 min. (91%). Mass Spec: 307.19 (MH+).

EXAMPLE 27

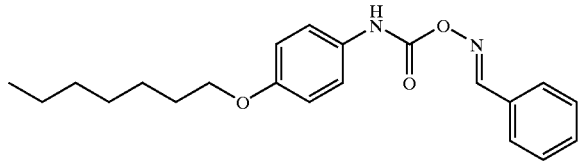

Benzaldehyde, O-[[(4-heptyloxyphenyl)amino]carbonyl]oxime (Scheme 1, Compound D) Prepared as described for the example above. Analytical HPLC 2.11 min. (93%). Mass Spec: 355.18 (MH+).

EXAMPLE 28

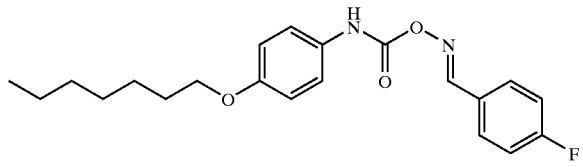

4-Fluorobenzaldehyde, O-[[(4-heptyloxyphenyl)amino]carbonyl]oxime (Scheme 1, Compound D) Prepared as described for the example above. Analytical HPLC 2.10 min. (90%). Mass Spec: 373.11 (MH+).

EXAMPLE 29

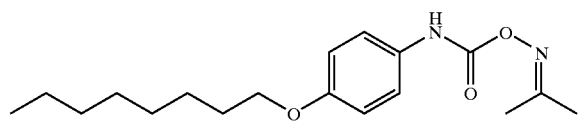

2-Propanone, O-[[(4-octyloxyphenyl)amino]carbonyl]oxime (Scheme 1, Compound D) Prepared as described for the example above. Analytical HPLC 1.89 min. (87%). Mass Spec: 321 (MH+).

EXAMPLE 30

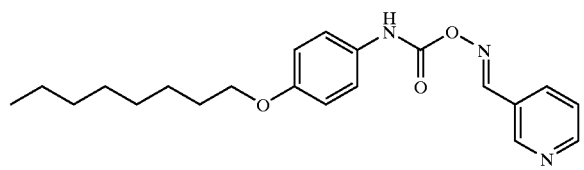

3-Pyridinecarboxaldehyde, O-[[(4-octyloxyphenyl)amino]carbonyl]oxime (Scheme 1, Compound D) Prepared as described for the example above. Analytical HPLC 2.0 min. (85%). Mass Spec: 370.13 (MH+).

EXAMPLE 31

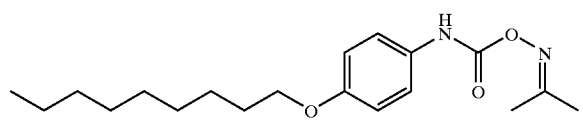

2-Propanone, O-[[(4-nonyloxyphenyl)amino]carbonyl]oxime (Scheme 1, Compound D) Prepared as described for the example above. Analytical HPLC 1.64 min. (97%). Mass Spec: 335.31 (MH+).

EXAMPLE 32

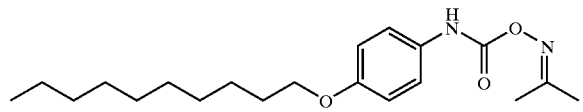

2-Propanone, O-[[(4-decyloxyphenyl)amino]carbonyl]oxime (Scheme 1, Compound D) Prepared as described for the example above. Analytical HPLC 2.03 min. (99%). Mass Spec: 349.35 (MH+).

EXAMPLE 33

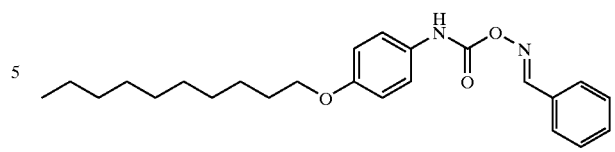

Benzaldehyde, O-[[(4-decyloxyphenyl)amino]carbonyl]oxime (Scheme 1, Compound D) Prepared as described for the example above. Analytical HPLC 2.10 min. (99%). Mass Spec: 397.38 (MH+).

EXAMPLE 34

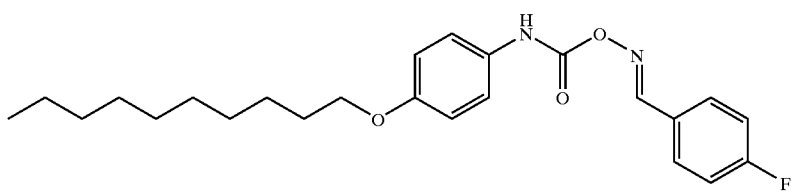

4-Fluorobenzaldehyde, O-[[(4-decyloxyphenyl)amino]carbonyl]oxime (Scheme 1, Compound D) Prepared as described for the example above. Analytical HPLC 2.11 min. (97%). Mass Spec: 415.34 (MH+).

EXAMPLE 35

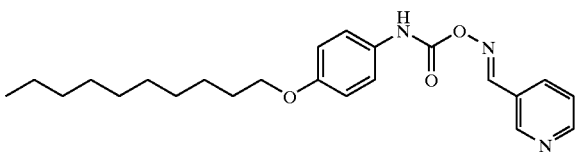

3-Pyridinecarboxaldehyde, O-[[(4-decyloxyphenyl)amino]carbonyl]oxime (Scheme 1, Compound D) Prepared as described for the example above. Analytical HPLC 2.01 min. (85%). Mass Spec: 398.34 (MH+).

EXAMPLE 36

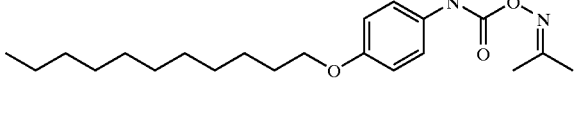

2-Propanone, O-[[(4-undecyloxyphenyl)amino]carbonyl]oxime (Scheme 1, Compound D) Prepared as described for the example above. Analytical HPLC 2.25 min. (90%). Mass Spec: 363.26 (MH+).

EXAMPLE 37

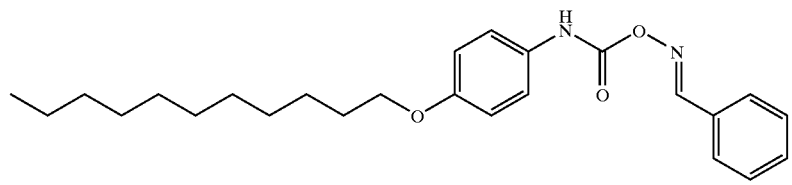

Benzaldehyde, O-[[(4-undecyloxyphenyl)amino]carbonyl]oxime (Scheme 1, Compound D) Prepared as described for the example above. Analytical HPLC 2.36 min. (96%). Mass Spec: 411.28 (MH+).

EXAMPLE 38

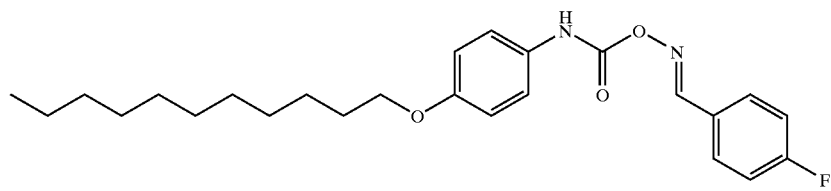

4-Fluorobenzaldehyde, O-[[(4-undecyloxyphenyl)amino]carbonyl]oxime (Scheme 1, Compound D) Prepared as described for the example above. Analytical HPLC 2.37 min. (97%). Mass Spec: 429.30 (MH+).

EXAMPLE 39

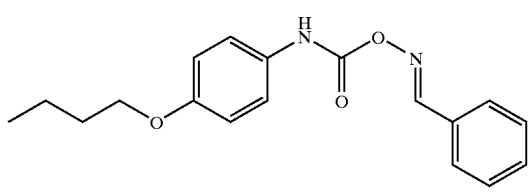

Benzaldehyde, O-[[(4-butoxyphenyl)amino]carbonyl]oxime (Scheme 1, Compound D) Prepared as described for the example above. $^1$H NMR (DMSO-$d_6$) δ 9.66 (s, 1H), 8.62 (s, 1H), 7.82 (m, 2H), 7.52 (m, 3H), 7.40 (d, 2H, J=8.5 Hz), 6.90 (d, 2H, J=9.0 Hz), 3.92 (t, 2H, J=6.5 Hz), 1.72 (m, 2H), 1.40 (m, 2H), 0.92 (t, 3H, J=7.5 Hz); Analytical HPLC 1.67 min. (90%). Mass Spec: 313.15 (MH+).

EXAMPLE 40

2-Propanone, O-[[(4-dodecyloxyphenyl)amino]carbonyl]oxime (Scheme 1, Compound D) Prepared as described for the example above. Analytical HPLC 2.15 min. (99%). Mass Spec: 377.43 (MH+).

EXAMPLE 41

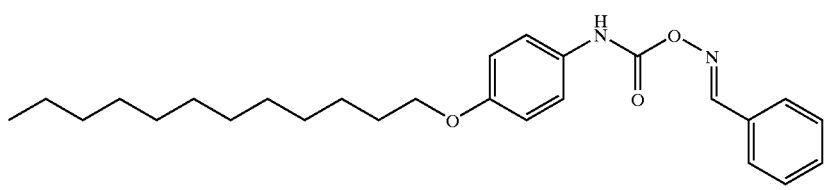

Benzaldehyde, O-[[(4-dodecyloxyphenyl)amino]carbonyl]oxime (Scheme 1, Compound D) Prepared as described for the example above. Analytical HPLC 2.20 min. (99%). Mass Spec: 425.41 (MH+).

EXAMPLE 42

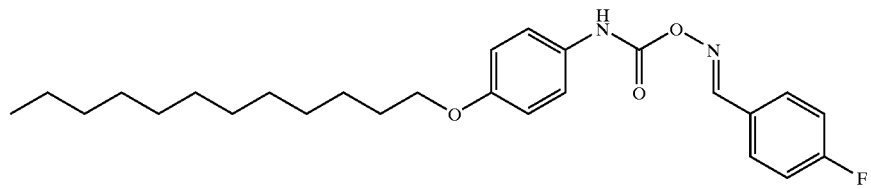

4-Fluorobenzaldehyde, O-[[(4-dodecyloxyphenyl)amino]carbonyl]oxime (Scheme 1, Compound D) Prepared as described for the example above. Analytical HPLC 2.21 min. (99%). Mass Spec: 443.37 (MH+).

EXAMPLE 43

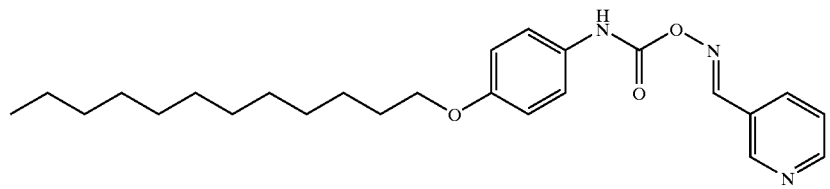

3-Pyridinecarboxaldehyde, O-[[(4-dodecyloxyphenyl)amino]carbonyl]oxime (Scheme 1, Compound D) Prepared as described for the example above. Analytical HPLC 2.27 min. (85%). Mass Spec: 426.32 (MH+).

EXAMPLE 44

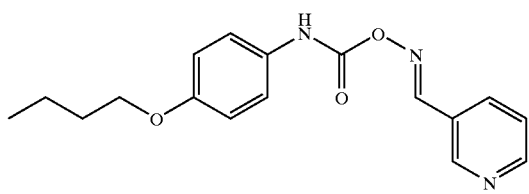

3-Pyridinecarboxaldehyde, O-[[(4-butoxyphenyl)amino]carbonyl]oxime (Scheme 1, Compound D) Prepared as described for the example above. Analytical HPLC 1.48 min. (95%). Mass Spec: 314.20 (MH+).

EXAMPLE 45

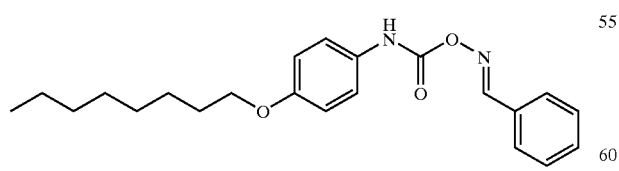

Benzaldehyde, O-[[(4-octyloxyphenyl)amino]carbonyl]oxime (Scheme 1, Compound D) Prepared as described for the example above. Analytical HPLC 1.99 min. (99%). Mass Spec: 369.27 (MH+).

EXAMPLE 46

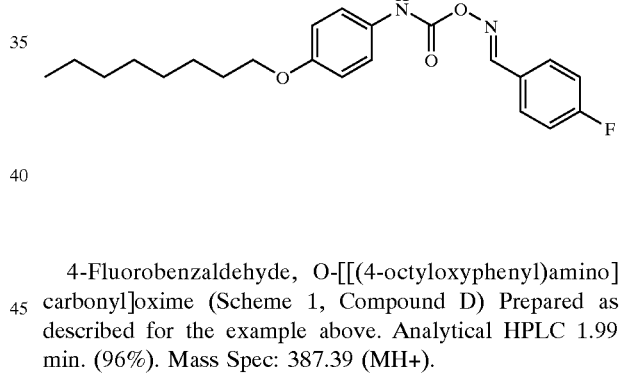

4-Fluorobenzaldehyde, O-[[(4-octyloxyphenyl)amino]carbonyl]oxime (Scheme 1, Compound D) Prepared as described for the example above. Analytical HPLC 1.99 min. (96%). Mass Spec: 387.39 (MH+).

EXAMPLE 47

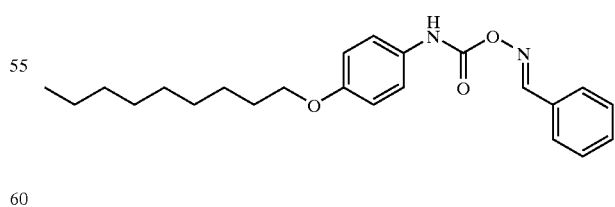

Benzaldehyde, O-[[(4-nonyloxyphenyl)amino]carbonyl]oxime (Scheme 1, Compound D) Prepared as described for the example above. Analytical HPLC 2.04 min. (95%). Mass Spec: 383.30 (MH+).

EXAMPLE 48

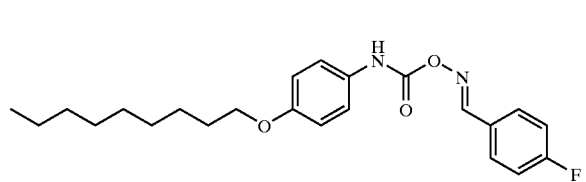

4-Fluorobenzaldehyde, O-[[(4-nonyloxyphenyl)amino]carbonyl]oxime (Scheme 1, Compound D) Prepared as described for the example above. Analytical HPLC 2.0 min. (95%). Mass Spec: 401.30 (MH+).

EXAMPLE 49

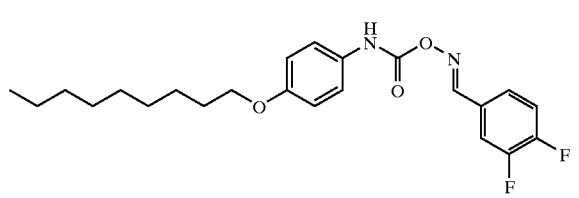

3,4-Difluorobenzaldehyde, O-[[(4-nonyloxyphenyl)amino]carbonyl]oxime (Scheme 1, Compound D) Prepared as described for the example above. $^1$H NMR (DMSO-d$_6$) δ 9.66 (s, 1H), 8.62 (s, 1H), 7.90 (m, 1H), 7.65 (m, 2H), 7.40 (d, 2H, J=8.7 Hz), 6.90 (d, 2H, J=9.0 Hz), 3.92 (t, 2H, J=6.5 Hz), 1.72 (m, 2H), 1.25 (m, 12H), 0.85 (t, 3H, J=7.5 Hz). Analytical HPLC 2.03 min. (95%). Mass Spec: 419.20 (MH+).

EXAMPLE 50

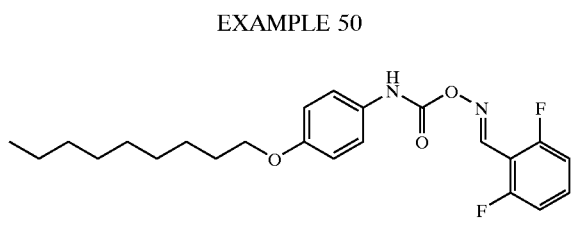

2,6-Difluorobenzaldehyde, O-[[(4-nonyloxyphenyl)amino]carbonyl]oxime (Scheme 1, Compound D) Prepared as described for the example above. Analytical HPLC 2.05 min. (85%). Mass Spec: 419 (MH+).

EXAMPLE 51

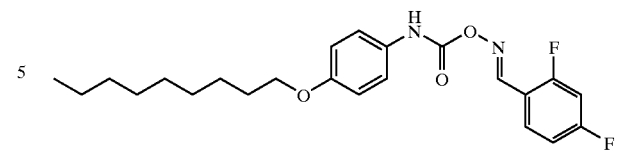

2,4-Difluorobenzaldehyde, O-[[(4-nonyloxyphenyl)amino]carbonyl]oxime (Scheme 1, Compound D) Prepared as described for the example above. Analytical HPLC 2.07 min. (99%). Mass Spec: 419.31 (MH+).

EXAMPLE 52

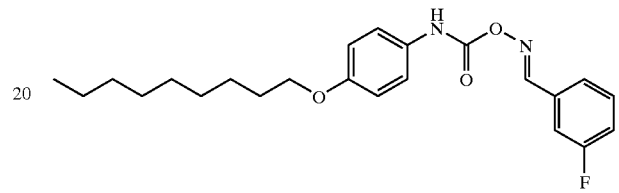

3-Fluorobenzaldehyde, O-[[(4-nonyloxyphenyl)amino]carbonyl]oxime (Scheme 1, Compound D) Prepared as described for the example above. Analytical HPLC 2.05 min. (95%). Mass Spec: 401.33 (MH+).

EXAMPLE 53

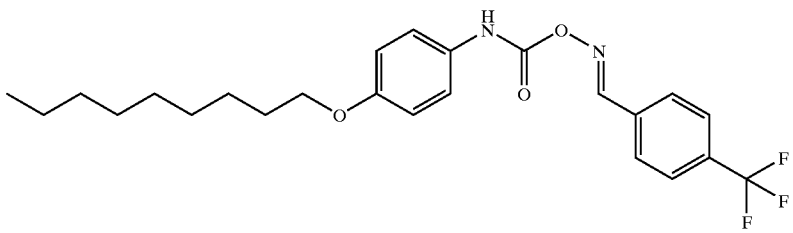

4-(Trifluoromethyl)benzaldehyde, O-[[(4-nonyloxyphenyl)amino]carbonyl]oxime (Scheme 1, Compound D) Prepared as described for the example above. Analytical HPLC 1.64 min. (99%). Mass Spec: 451.25 (MH+).

EXAMPLE 54

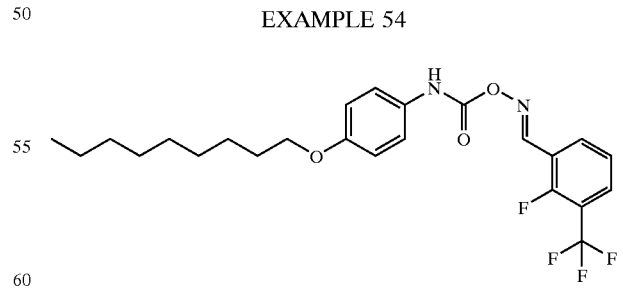

2-Fluoro-3-(trifluoromethyl)benzaldehyde, O-[[(4-nonyloxyphenyl)amino]carbonyl]oxime (Scheme 1, Compound D) Prepared as described for the example above. Analytical HPLC 2.11 min. (85%). Mass Spec: 469.07 (MH+).

EXAMPLE 55

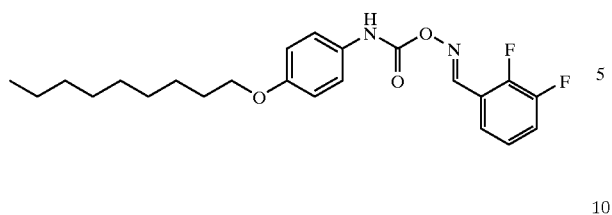

2,3-Difluorobenzaldehyde, O-[[(4-nonyloxyphenyl)amino]carbonyl]oxime (Scheme 1, Compound D) Prepared as described for the example above. Analytical HPLC 2.08 min. (90%). Mass Spec: 419.17 (MH+).

EXAMPLE 56

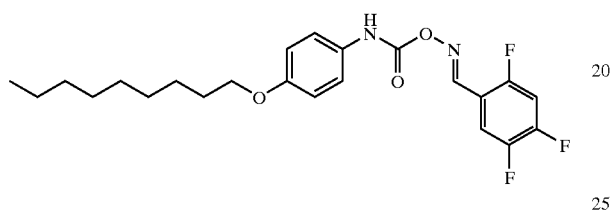

2,4,5-Trifluorobenzaldehyde, O-[[(4-nonyloxyphenyl)amino]carbonyl]oxime (Scheme 1, Compound D) Prepared as described for the example above. Analytical HPLC 2.01 min. (95%). Mass Spec: 437 (MH+).

EXAMPLE 57

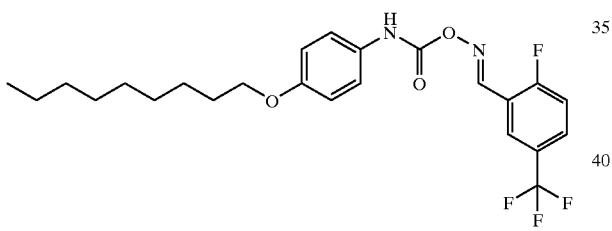

2-Fluoro-5-(trifluoromethyl)benzaldehyde, O-[[(4-nonyloxyphenyl)amino]carbonyl]oxime (Scheme 1, Compound D) Prepared as described for the example above. Analytical HPLC 2.11 min. (95%). Mass Spec: 469.13 (MH+).

EXAMPLE 58

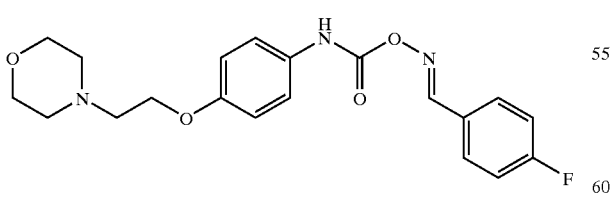

4-Fluorobenzaldehyde, O-[[4-[3-(4-morpholinyl)propoxyphenyl]amino]carbonyl]oxime (Scheme 1, Compound D) Prepared as described for the example above. Analytical HPLC 2.68 min. (85%). Mass Spec: 402.30 (MH+).

EXAMPLE 59

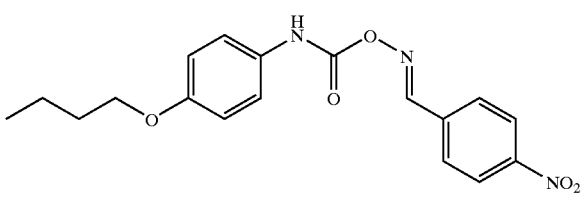

4-Nitrobenzaldehyde, O-[[(4-butoxyphenyl)amino]carbonyl]oxime (Scheme 1, Compound D) Prepared as described for the example above. Analytical HPLC 1.83 min. (85%). Mass Spec: 358.17 (MH+).

EXAMPLE 60

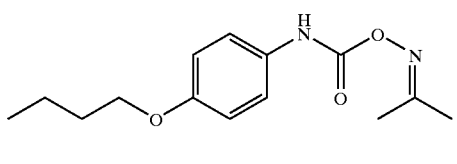

2-Propanone, O-[[(4-butoxyphenyl)amino]carbonyl]oxime (Scheme 1, Compound D) Prepared as described for the example above. $^1$H NMR (DMSO-$d_6$) δ 9.39 (br. s, 1H), 7.36 (d, 2H, J=8.1 Hz), 6.90 (dd, 2H, J=7.0, 2.5 Hz), 3.92 (t, 2H, J=6.5 Hz), 1.97 (s, 6H), 1.67 (m, 2H), 1.42 (m, 2H), 0.91 (t, 3H, J=7.0 Hz). Analytical HPLC 1.59 min. (95%). Mass Spec: 265.16 (MH+).

EXAMPLE 61

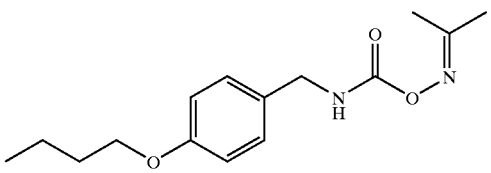

2-Propanone, O-[[(4-butoxyphenylmethyl)amino]carbonyl]oxime (Scheme 1, Compound D) Prepared as described for the example above. Analytical HPLC 1.44 min. (95%). Mass Spec: 279.32 (MH+).

EXAMPLE 62

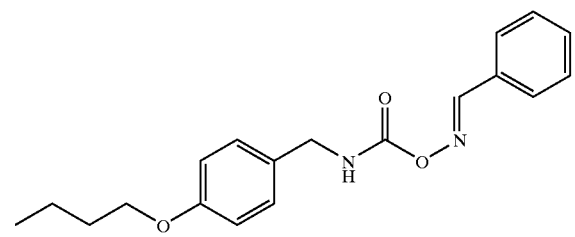

Benzaldehyde, O-[[(4-butoxyphenylmethyl)amino]carbonyl]oxime (Scheme 1, Compound D) Prepared as described for the example above. Analytical HPLC 1.66 min. (95%). Mass Spec: 327.31 (MH+).

EXAMPLE 63

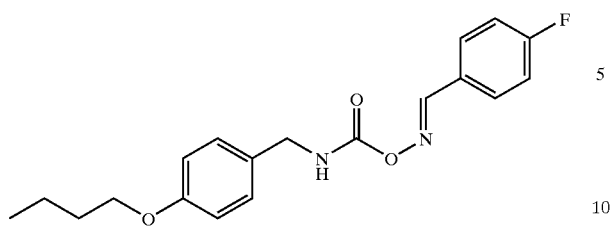

4-Fluorobenzaldehyde, O-[[(4-butoxyphenylmethyl)amino]carbonyl]oxime (Scheme 1, Compound D) Prepared as described for the example above. Analytical HPLC 1.66 min. (85%). Mass Spec: 345.28 (MH+).

EXAMPLE 64

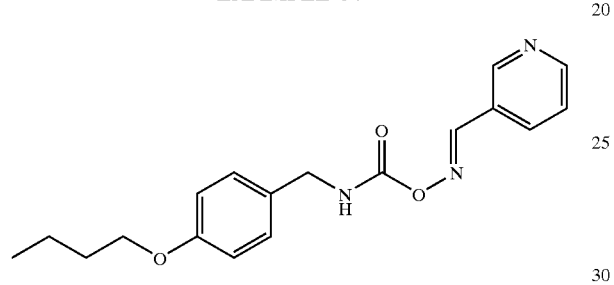

3-Pyridinecarboxaldehyde, O-[[(4-butoxyphenylmethyl)amino]carbonyl]oxime (Scheme 1, Compound D) Prepared as described for the example above. Analytical HPLC 1.55 min. (95%). Mass Spec: 328.29 (MH+).

EXAMPLE 65

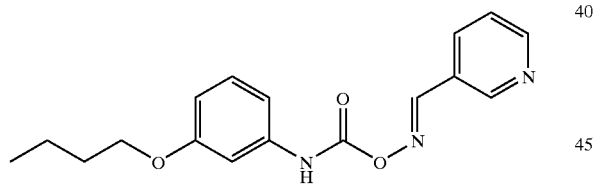

3-Pyridinecarboxaldehyde, O-[[(3-butoxyphenyl)amino]carbonyl]oxime (Scheme 1, Compound D) Prepared as described for the example above. Analytical HPLC 1.39 min. (95%). Mass Spec: 314.28 (MH+).

EXAMPLE 66

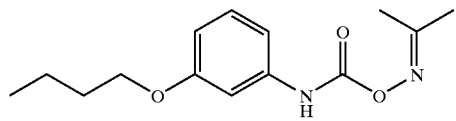

2-Propanone, O-[[(3-butoxyphenyl)amino]carbonyl]oxime (Scheme 1, Compound D) Prepared as described for the example above. Analytical HPLC 1.47 min. (97%). Mass Spec: 265.32 (MH+).

EXAMPLE 67

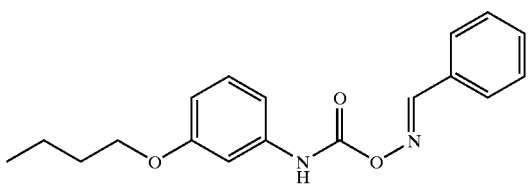

Benzaldehyde, O-[[(3-butoxyphenyl)amino]carbonyl]oxime (Scheme 1, Compound D) Prepared as described for the example above. Analytical HPLC 1.69 min. (92%). Mass Spec: 313.27 (MH+).

EXAMPLE 68

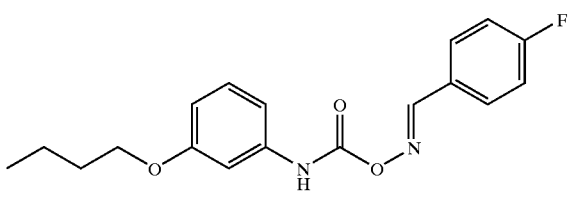

4-Fluorobenzaldehyde, O-[[(3-butoxyphenyl)amino]carbonyl]oxime (Scheme 1, Compound D) Prepared as described for the example above. Analytical HPLC 1.71 min. (92%). Mass Spec: 331.30 (MH+).

EXAMPLE 69

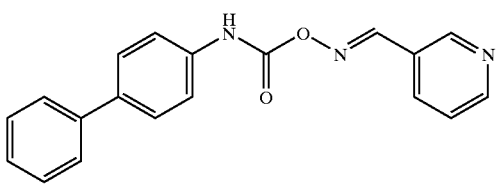

3-Pyridinecarboxaldehyde, O-[[([1,1'-biphenyl]-4-yl)amino]carbonyl]oxime (Scheme 1B, Compound D') Prepared as described for the example above. Using work-up method A: filtration of the reaction mixture, and the solid was recrystallized from EtOAc/hexanes, provided the title compound as light yellow solid in 38% yield. $^1$H NMR (DMSO, 400 MHz) δ 10.06 (s, 1H), 8.96 (d, J=2.0 Hz, 1H), 8.74 (s, 1H), 8.72 (dd, J=1.6 Hz, J=4.8 Hz, 1H), 8.25 (dt, J=1.8 Hz, J=6.2 Hz 1H), 7.68–7.63 (m, 6H), 7.67–7.64 (dd, J=4.8 Hz, J=8.4 Hz, 1H), 7.45 (t, J=7.2 Hz, 2H), 7.34 (t, J=7.2 Hz, 1H); 13C NMR (DMSO, 400 MHz) δ 152.7, 152.0, 151.5, 149.3, 139.5, 137.5, 135.0, 134.6, 128.8, 127.0, 126.5, 126.2, 124.0, 119.5; Mass spec.: 318.0 (MH+); Anal. Calcd. for $C_{19}H_{14}N_3O_2$: C=72.14%, H=4.46%, N=13.28%; found: C=72.09%, H=4.68%, N=13.14%.

EXAMPLE 70

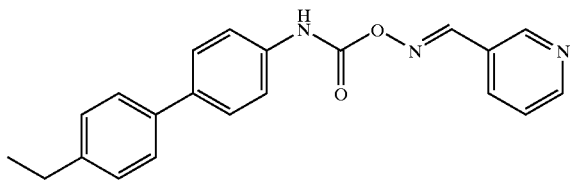

3-Pyridinecarboxaldehyde, O-[[(4'-ethyl-[1,1'-biphenyl]-4-yl)amino]carbonyl]oxime (Scheme 1B, Compound D') Prepared as described for the example above. $^1$H NMR (DMSO, 400 MHz) δ 10.03 (s, 1H), 8.97 (d, J=1.7 Hz, 1H), 8.74 (s, 1H), 8.72 (dd, J=1.7 Hz, J=4.8 Hz, 1H), 8.25 (dt, J=1.6 Hz, J=8.0 Hz 1H), 7.63 (m, 4H), 7.57–7.54 (m, 3H), 7.28 (d, J=8.3 Hz, 2H), 2.63 (q, J=7.2 Hz, 2H), 1.20 (t, J=7.6 Hz, 3H); $^{13}$C NMR (DMSO, 400 MHz) δ 152.6, 151.9, 151.5, 149.3, 142.6, 137.2, 136.9, 135.0, 134.6, 128.2, 126.7, 126.5, 126.1, 124.0, 119.5, 27.7, 15.5; Mass spec.: 346.1 (MH$^+$); Anal. Calcd. for $C_{21}H_{18}N_3O_2$: C=73.24%, H=5.26%, N=12.20; found: C=73.10%, H=5.46%, H=12.25%.

EXAMPLE 71

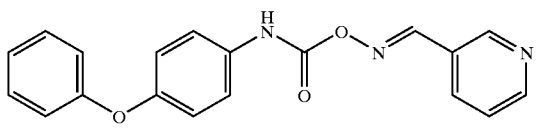

3-Pyridinecarboxaldehyde, O-[[(4-phenoxyphenyl)amino]carbonyl]oxime (Scheme 1B, Compound D') Prepared as described for the example above. Using work-up method A provided the title compound as white need like crystal in 24% yield. $^1$H NMR (DMSO, 400 MHz) δ 9.94, (s, 1H), 8.96 (d, J=1.7 Hz, 1H), 8.72 (s, 1H), 8.71 (dd, J=1.8 Hz, J=4.9 Hz, 1H), 8.25 (dt, J=1.9 Hz, J=8.0 Hz, 1H), 7.56–7.53 (m 3H), 7.37 (t, J=7.4 Hz, 2H), 7.11 (t, J=8.4 Hz, 1H), 7.03 (d, J=6.8 Hz, 2H), 6.98 (d, 8.2 Hz, 2H); $^{13}$C NMR (DMSO, 400 MHz) δ 157.2, 152.5, 151.9, 151.7, 149.3, 134.6, 133.8, 129.9, 126.5, 124.0, 122.9, 121.1, 119.5, 117.8; Mass spec.: 334.0 (MH$^+$); Anal. Calcd. for $C_{19}H_{14}N_3O_3$: C=68.66%, H=4.24%, N=12.64%; found: C=68.50%, H=4.49%, N=12.57%.

EXAMPLE 72

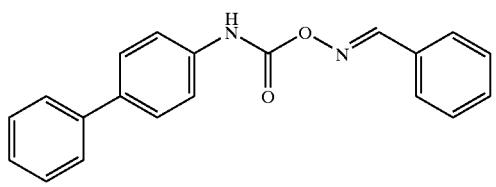

Benzaldehyde, O-[[([1,1'-biphenyl]-4-yl)amino]carbonyl]oxime (Scheme 1B, Compound D') Prepared as described for the example above. Using work-up method B: after removal of the solvent, the residue was chromatographed by silica gel column packed with EtOAc/hexanes or EtOAc/dichloromethane, to provide the title compound as white solid in 25% yield. $^1$H NMR (CDCl$_3$, 400 MHz) δ 8.44 (s, 1H), 8.18 (br, 1H), 7.75–7.73 (m 2H), 7.61–7.58 (m, 6H), 7.54–7.42 (m, 5H), 7.34 (tt, J=1.2 Hz, J=7.4 Hz, 1H). Anal. Calcd. for $C_{20}H_{15}N_2O_2 \cdot 0.198H_2O$: C=75.32%, H=4.87%, N=8.78%; found: C=75.33%, H=5.16%, N=8.66%.

EXAMPLE 73

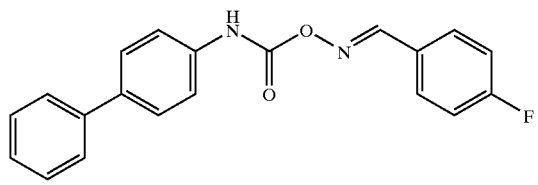

Benzaldehyde, O-[[([1,1'-biphenyl]-4-yl)amino]carbonyl]oxime (Scheme 1B, Compound D') Prepared as described for the example above. Using work-up method B provided the title compound as white solid in 14% yield. $^1$H NMR (CDCl$_3$, 400 MHz) δ 8.40 (s, 1H), 8.09 (br, 1H), 7.77–7.73 (m 2H), 7.60–7.58 (m, 6H), 7.44 (t, J=7.3 Hz, 2H), 7.34 (tt, J=1.2 Hz, J=7.4 Hz, 1H), 7.18 (t, J=8.56 Hz, 2H); 166.6, 164.0, 1.52.7, 151.7, 140.4, 137.4, 136.1, 130.4, 130.3, 128.8, 127.8, 127.2, 126.9, 126.0, 120.0, 116.6, 116.4.

EXAMPLE 74

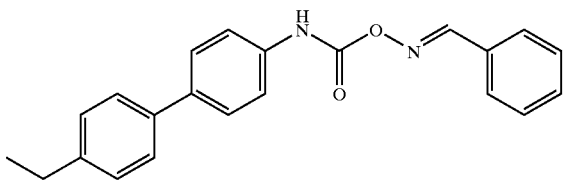

Benzaldehyde, O-[[(4'-ethyl-[1,1'-biphenyl]-4-yl)amino]carbonyl]oxime (Scheme 1B, Compound D') Prepared as described for the example above. Using work-up method C: after removal of solvent, the residue was dissolved in methanol and filtrated, the filtrate was purified by preparative HPLC with methanol:H$_2$O (30:70 to about 100:0 v/v, containing 1% TFA) as a mobile phase to provide the title compound as white solid in 11% yield. $^1$H NMR (DMSO, 500 MHz) δ 9.99 (s, 1H), 8.66 (s, 1H), 7.84 (d, J=8.1 Hz, 2H), 7.66–7.60 (m, 4H), 7.57–7.50 (m, 5H), 7.28 (d, J=88.11 Hz, 2H), 2.63 (q, J=7.5 Hz, 2H), 1.21 (m, 3H); $^{13}$C NMR (DMSO, 500 MHz) δ 154.8, 151.7, 142.5, 137.4, 136.9, 131.4, 130.3, 128.9, 128.2, 128.0, 126.7, 126.1, 119.4, 27.7, 15.5; Mass spec.: 345.1 (MH$^+$); Anal. Calcd. for $C_{22}H_{20}N_2O_2$: C=76.72%, H=5.85%, N=8.13%; found: C=76.67%, H=5.91%, N=8.02%.

EXAMPLE 75

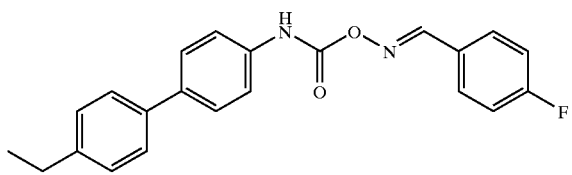

4-Fluorobenzaldehyde, O-[[(4'-ethyl-[1,1'-biphenyl]-4-yl)amino]carbonyl]oxime (Scheme 1B, Compound D') Prepared as described for the example above. Using work-up method C provided the title compound as white solid in 10% yield. $^1$H NMR (CDCl$_3$, 400 MHz) δ 8.40 (s, 1H), 8.06 (s, 1H), 7.76–7.73 (m, 2H), 7.59 (m, 4H), 7.52–7.50 (m, 2H), 7.27 (d, J=8.2 Hz, 2H), 7.18 (t, J=8.6 Hz, 2H), 2.70 (q, J=7.6 Hz, 2H), 1.28 (t, J=7.6 Hz, 3H); $^{13}$C NMR (CDCl$_3$, 400 MHz) δ 166.0, 164.0, 152.7, 151.7, 143.4, 137.8, 137.4, 135.8, 130.4, 130.3, 128.3, 127.6, 126.8, 120.0, 116.5, 116.4, 28.5, 15.6; Anal. Calcd. for C$_{22}$H$_{19}$FN$_2$O$_2$: C=72.91%, H=5.28%, N=7.73%; found: C=72.51%, H=5.40%, N=7.63%.

EXAMPLE 76

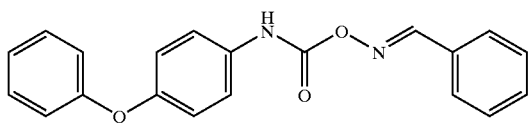

Benzaldehyde, O-[[(4-phenoxyphenyl)amino]carbonyl]oxime (Scheme 1B, Compound D') Prepared as described for the example above. Using work-up method B provided the title compound as white solid in 28% yield. $^1$H NMR (CDCl$_3$, 500 MHz) δ 8.35 (s, 1H), 8.03 (br, 1H), 7.66 (d, J=8.5 2H), 7.47–7.39 (m, 5H), 7.28–7.25 (m, 2H), 7.02 (t, J=7.4 Hz, 1H), 6.98–6.92 (m, 4H); Mass spec.: 333.1 (MH$^+$); Anal. Calcd. for C$_{20}$H$_{16}$N$_2$O$_3$: C=72.28%, H=4.85%, N=8.43%; found: C=72.12%, H=4.80%, N=8.39%.

EXAMPLE 77

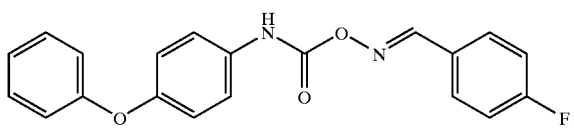

4-Fluorobenzaldehyde, O-[[(4-phenoxyphenyl)amino]carbonyl]oxime (Scheme 1B, Compound D') Prepared as described for the example above. Using work-up method B provided the title compound as white solid in 26% yield. $^1$H NMR (CDCl$_3$, 400 MHz) δ 8.39 (s, 1H), 7.99 (br, 1H), 7.75–7.71 (m, 2H), 7.48 (m, 2H), 7.33 (m, 2H), 7.19–7.15 (m, 2H), 7.09 (t, J=7.4 Hz, 1H), 7.05–6.98 (m, 4H); Anal. Calcd. for C$_{20}$H$_{15}$FN$_2$O$_3$.0.185H$_2$O: C=68.11%, H=4.11%, N=7.94%; found: C=68.11%, H=4.36%, N=7.88%.

EXAMPLE 78

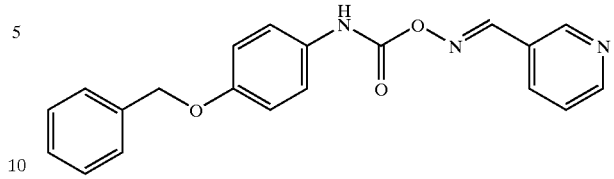

3-Pyridinecarboxaldehyde, O-[[[4-(phenylmethoxy)phenyl]amino]carbonyl]oxime (Scheme 1B, Compound D') Prepared as described for the example above. Using work-up method A provided the title compound as white solid in 50% yield. $^1$H NMR (CDCl$_3$, 500 MHz) δ 8.90 (br, 1H), 8.75 (br, 1H), 8.43 (s, 1H), 8.09 (d, J=7.9 Hz, 1H), 7.84 (br, 1H), 7.44–7.31 (m, 8H), 6.98 (d, J=8.9 Hz, 2H), 5.07 (s, 2H); $^{13}$C NMR (CDCl$_3$, 500 MHz) δ 155.9, 152.6, 151.8, 151.1, 149.7, 136.9, 134.5, 129.9, 128.6, 128.0, 127.5, 123.9, 121.8, 115.5, 70.3; Mass spec.: 348.1 (MH$^+$); Anal. Calcd. for C$_{20}$H$_{17}$N$_3$O$_3$: C=69.15%, H=4.93%, N=12.10%; found: C=68.90%, H=5.05%, N=12.10%.

EXAMPLE 79

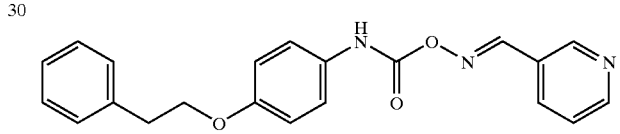

3-Pyridinecarboxaldehyde, O-[[[4-(2-phenylethoxy)phenyl]amino]carbonyl]oxime (Scheme 1B, Compound D') Prepared as described for the example above. Using work-up method A provided the title compound as white solid in 21% yield. $^1$H NMR (CDCl$_3$, 500 MHz) δ 8.92 (br, 1H), 8.77 (br, 1H), 8.44 (s, 1H), 8.11 (d, J=7.9 Hz, 1H), 7.81 (br, 1H), 7.44 (br, 1H), 7.39 (d, J=8.9 Hz, 2H), 7.34–7.28 (m, 4H), 7.26–7.22 (m, 1H), 6.90 (dt, J=3.4 Hz, J=8.9 Hz, 2H), 4.17 (q, J=7.15 Hz, 2H), 3.10 (t, J=7.1 Hz, 3H); $^{13}$C NMR (CDCl$_3$, 500 MHz) δ 152.4, 151.8, 151.0, 149.5, 180.0, 136.5, 134.6, 129.0, 128.5, 126.5, 122.0, 115, 69.0, 35.8; Mass spec.: 362.0 (MH$^+$); Anal. Calcd. for C$_{21}$H$_{19}$N$_3$O$_3$: C=69.79%, H=5.30%, N=11.63%; found: C=69.42%, H=5.26%, N=11.65%.

EXAMPLE 80

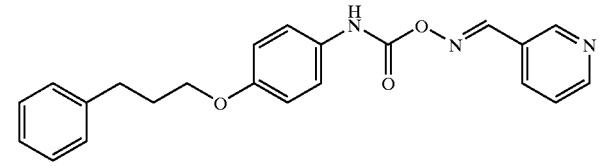

3-Pyridinecarboxaldehyde, O-[[[4-(3-phenylpropoxy)phenyl]amino]carbonyl]oxime (Scheme 1B, Compound D') Prepared as described for the example above. Using work-up method A provided the title compound as white solid in 26% yield. $^1$H NMR (CDCl$_3$, 500 MHz) δ 8.94 (br, 1H), 8.79 (br, 1H), 8.44 (s, 1H), 8.10 (d, J=7.9 Hz, 1H), 7.82 (br, 1H), 7.45 (br, 1H), 7.40 (d, J=8.9 Hz, 2H), 7.30–7.28 (m, 2H), 7.22–7.18 (m, 3H), 6.90 (dt, J=3.4 Hz, J=8.9 Hz, 2H), 3.96 (t, J=6.3 Hz, 2H), 2.82 (t, J=7.35 Hz, 2H), 2.11 (m, 2H); $^{13}$C NMR (CDCl$_3$, 500 MHz) δ 161.5, 152.0, 150.5, 141.5, 134.5, 129.5, 128.5, 128.4, 125.9, 121.8, 115.1, 67.2, 32.1, 30.8; Mass spec.: 376.1 (MH$^+$); Anal. Calcd. for C$_{22}$H$_{21}$N$_3$O$_3$: C=70.38%, H=5.64%, N=11.19%; found: C=69.96%, H=5.59%, N=11.03%.

EXAMPLE 81

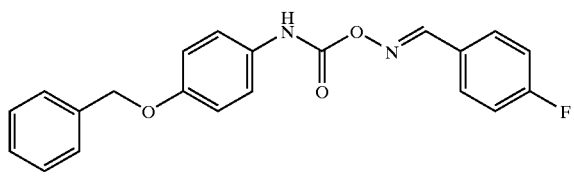

4-Fluorobenzaldehyde, O-[[[4-(phenylmethoxy)phenyl]amino]carbonyl]oxime (Scheme 1B, Compound D') Prepared as described for the example above. Using work-up method C provided the title compound as white solid in 10% yield. $^1$H NMR (CDCl$_3$, 500 MHz) δ 8.31 (s, 1H), 7.86 (br, 1H), 7.65 (dd, J=5.3 Hz, J=8.7 Hz, 2H), 7.37–7.30 (m, 6H), 7.27–7.24 (t, J=7.2 Hz, 1H), 7.09 (t, J=8.6 Hz, 2H), 6.91 (dt, J=3.4 Hz, J=8.9 Hz, 2H), 4.99 (s, 2H); Mass spec.: 365.1 (MH$^+$); Anal. Calcd. for C$_{21}$H$_{17}$FN$_2$O$_3$: C=69.22%, H=4.70%, N=7.69%; found: C=69.44%, H=4.84%, N=7.54%.

EXAMPLE 82

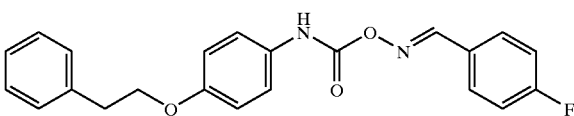

4-Fluorobenzaldehyde, O-[[[4-(2-phenylethoxy)phenyl]amino]carbonyl]oxime (Scheme 1B, Compound D') Prepared as described for the example above. Using work-up method C provided the title compound as white solid in 48% yield. $^1$H NMR (CDCl$_3$, 500 MHz) δ 8.31 (s, 1H), 7.85 (br, 1H), 7.67–7.63 (m, 2H), 7.32 (d, J=8.9 Hz, 2H), 7.27–7.21 (m, 4H), 7.18 (t, J=7.0 Hz, 1H), 6.83 (dt, J=3.4 Hz, J=8.9 Hz, 2H), 4.10 (t, J=7.2 Hz, 2H), 3.03 (t, J=7.1 Hz, 2H); Mass spec.: 379.1 (MH$^+$); Anal. Calcd. for C$_{22}$H$_{19}$FN$_2$O$_3$: C=69.83%, H=5.06%, N=7.40%; found: C=69.71%, H=5.05%, N=7.21%.

EXAMPLE 83

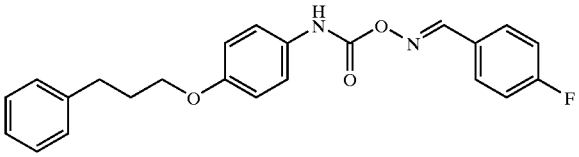

4-Fluorobenzaldehyde, O-[[[4-(3-phenylpropoxy)phenyl]amino]carbonyl]oxime (Scheme 1B, Compound D') Prepared as described for the example above. Using work-up method C provided the title compound as white solid in 32% yield. $^1$H NMR (CDCl$_3$, 500 MHz) δ 8.30 (s, 1H), 7.85 (br, 1H), 7.67–7.63 (m, 2H), 7.33 (d, J=8.9 Hz, 2H), 7.22 (t, J=6.0 Hz, 2H), 7.15–7.01 (m, 5H), 6.82 (dt, J=3.4 Hz, J=8.9 Hz, 2H), 3.88 (t, J=6.3 Hz, 2H), 2.74 (t, J=7.4 Hz, 2H), 2.03 (m, 2H); $^{13}$C NMR (CDCl$_3$, 500 MHz) δ 156.2, 152.5, 141.5, 130.3, 130.3, 129.7, 128.5, 128.4, 125.9, 121.8, 116.5, 116.3, 115.0, 67.2, 32.1, 30.8; Mass spec.: 393.0 (MH$^+$); Anal. Calcd. for C$_{23}$H$_{21}$FN$_2$O$_3$·0.1H$_2$O: C=70.07%, H=5.42%, N=7.10%; found: C=70.09%, H=5.46%, N=6.71%.

EXAMPLE 84

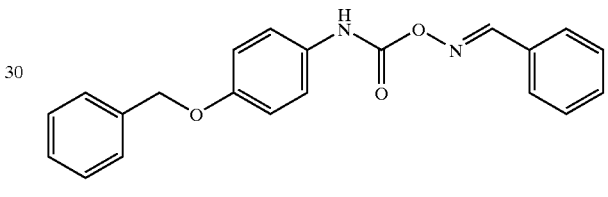

Benzaldehyde, O-[[[4-(phenylmethoxy)phenyl]amino]carbonyl]oxime (Scheme 1B, Compound D') Prepared as described for the example above. Using work-up method C provided the title compound as white solid in 33% yield. $^1$H NMR (CDCl$_3$, 500 MHz) δ 8.41 (s, 1H), 8.02 (br, 1H), 7.72–7.70 (m, 2H), 7.54–7.37 (m, 9H), 7.34–7.31 (m, 1H), 6.98 (dt, J=3.4 Hz, J=6.9 Hz, 2H), 5.07 (s, 2H); $^{13}$C NMR (CDCl$_3$, 500 MHz) δ 155.7, 153.6, 136.9, 131.9, 130.1, 129.8, 129.1, 128.6, 128.2, 128.0, 127.5, 121.8, 115.4; Mass spec.: 347.0 (MH$^+$); Anal. Calcd. for C$_{21}$H$_{18}$N$_2$O$_3$: C=72.82%, H=5.24%, N=8.09%; found: C=72.69%, H=5.28%, N=8.00%.

EXAMPLE 85

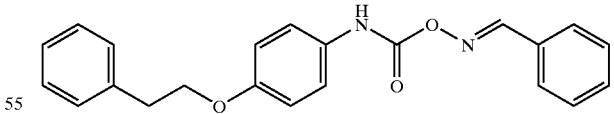

Benzaldehyde, O-[[[4-(2-phenylethoxy)phenyl]amino]carbonyl]oxime (Scheme 1B, Compound D') Prepared as described for the example above. Using work-up method C provided the title compound as white solid in 23% yield. $^1$H NMR (CDCl$_3$, 500 MHz) δ 8.41 (s, 1H), 8.01 (br, 1H), 7.72–7.70 (m, 2H), 7.54–7.45 (m, 3H), 7.41 (d, J=8.9 Hz, 2H), 7.34–7.28 (m, 4H), 7.26–7.23 (m, 2H), 6.90 (dt, J=3.3 Hz, J=9.0 Hz, 2H), 4.17 (t, J=7.2 Hz, 2H), 3.10 (t, J=7.1 Hz, 2H); $^{13}$C NMR (CDCl$_3$, 500 MHz) δ 153.6, 152.3, 138.2, 136.2, 131.9, 129.9, 129.8, 129.1, 129.0, 128.5, 128.2, 126.5, 121.8, 115.1, 69.0, 35.8; Mass spec.: 361.0 (MH⁺); Anal. Calcd. for $C_{22}H_{20}N_2O_3$: C=73.32%, H=5.59%, N=7.77%; found: C=73.34%, H=5.82%, N=7.73%.

EXAMPLE 86

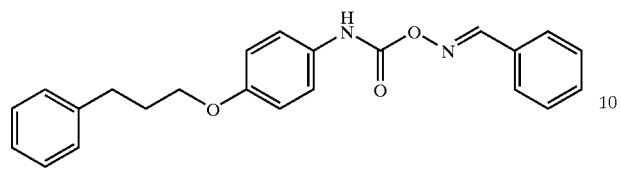

Benzaldehyde, O-[[[4-(3-phenylpropoxy)phenyl]amino] carbonyl]oxime (Scheme 1B, Compound D') Prepared as described for the example above. Using work-up method C provided the title compound as white solid in 25% yield. ¹H NMR (CDCl₃, 500 MHz) δ 8.41 (s, 1H), 8.02 (br, 1H), 7.72–7.71 (m, 2H), 7.54–7.46 (m, 3H), 7.41 (d, J=8.9 Hz, 2H), 7.30 (t, J=6.85 Hz, 2H), 7.23–7.19 (m, 3H), 6.90 (dt, J=3.4 Hz, J=9.0 Hz, 2H), 3.96 (t, J=6.3 Hz, 2H), 2.82 (t, J=7.4 Hz, 2H), 2.12 (m, 2H); ¹³C NMR (CDCl₃, 500 MHz) δ 156.1, 153,6, 152.4, 141.5, 136.2, 131.9, 129.85, 129.80, 128.5, 128.4, 128.2, 126.0, 121.8, 115.0, 67.2, 32.1, 30.8; Mass spec.: 375.0 (MH⁺); Anal. Calcd. for $C_{23}H_{22}N_2O_3$: C=73.78%, H=5.92%, N=7.48%; found: C=73.82%, H=6.02%, N=7.35%.

EXAMPLE 87

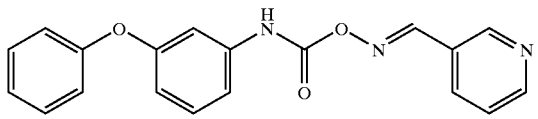

3-Pyridinecarboxaldehyde, O-[[(3-phenoxyphenyl) amino]carbonyl]oxime (Scheme 1B, Compound D') Prepared as described for the example above. Using work-up method C provided the title compound as white solid in 34% yield. ¹H NMR (DMSO, 400 MHz) δ 10.06 (s, 1H), 8.93 (d, J=1.6 Hz, 1H), 8.70 (d, J=1.6 Hz, 1H), 8.69 (s, 1H), 8.21 (dt, J=2.0 Hz, J=8.1 Hz, 1H), 7.54 (dd, J=4.9 Hz, J=7.8 Hz, 1H), 7.40 (t, J=7.4 Hz, 2H), 7.34 (t, J=8.1 Hz, 1H), 7.29–7.26 (m, 2H), 7/16 (t, J=7.4 Hz, 1H), 7.03 (dd, J=1.1 Hz, J=8.7 Hz, 2H), 6.71 (m, 1H); ¹³C NMR (DMSO, 400 MHz) δ 158.1, 152.6, 151.3, 149.7, 138.1, 134.6, 130.3, 129.8, 123.6, 119.2, 114.7, 114.3, 110.2; Mass spec.: 334.0 (MH⁺); Anal. Calcd. for $C_{19}H_{14}N_3O_3$: C=68.46%, H=4.54%, N=12.61%; found: C=68.42%, H=4.42%, N=12.62%.

EXAMPLE 88

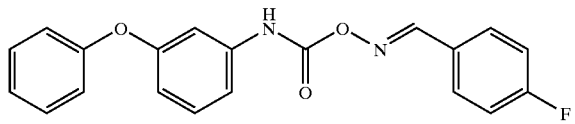

4-Fluorobenzaldehyde, O-[[(3-phenoxyphenyl)amino] carbonyl]oxime (Scheme 1B, Compound D') Prepared as described for the example above. Using work-up method C provided the title compound as white solid in 34% yield. ¹H NMR (CDCl₃, 500 MHz) δ 8.36 (s, 1H), 8.00 (br, 1H), 7.12 (m, 2H), 7.37–7.27 (m, 4H), 7.22 (t, J=2.1 Hz, 1H), 7.17–7.10 (m, 3H), 7.04 (dt, J=1.1 Hz, J=7.6 Hz, 2H), 6.78 (dt, J=2.1 Hz, J=7.1 Hz, 1H); ¹³C NMR (CDCl₃, 500 MHz) δ 165.9, 163.9, 158.0, 156.9, 152.8, 151.6, 138.3, 130.4, 130.3, 130.2, 129.8, 126.0, 125.9, 123.5, 119.1, 116.5, 116.4, 114.6, 114.4, 110.3; Mass spec.: 350.9 (MH⁺); Anal. Calcd. for $C_{20}H_{15}FN_2O_3$: C=68.57%, H=4.32%, N=8.00%; found: C=68.77%, H=4.48%, N=7.76%.

EXAMPLE 89

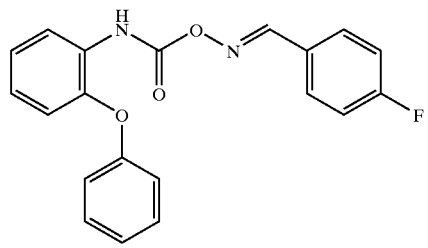

4-Fluorobenzaldehyde, O-[[(2-phenoxyphenyl)amino] carbonyl]oxime (Scheme 1B, Compound D') Prepared as described for the example above. Using work-up method C provided the title compound as white solid in 16% yield, mp 141.5–142.0° C. ¹H NMR (CDCl₃, 500 MHz) δ 8.73 (br, 1H), 8.32 (dd, J=1.3 Hz, J=8.2 Hz, 1H), 8.30 (s, 1H), 7.55–7.51 (m, 2H), 7.36 (t, J=8.7 Hz, 2H), 7.21 (t, J=7.8 Hz, 1H), 7.12 (t, J=7.4 Hz, 1H), 7.11–7.08 (m, 3H), 7.03 (d, J=8.7 Hz, 2H), 6.98 (d, J=1.4 Hz, J=8.1, 1H); ¹³C NMR (CDCl₃, 500 MHz) δ 156.8, 152.2, 145.0, 130.2, 130.1, 129.9, 129.4, 124.8, 124.1, 123.5, 119.9, 119.1, 117.4, 116.3, 116.2; Mass spec.: 351.0 (MH⁺); Anal. Calcd. for $C_{20}H_{15}FN_2O_3 \cdot 0.41H_2O$: C=67.15%, H=4.46%, N=7.83; found: C=67.13%, H=4.39%, N=7.76%.

EXAMPLE 90

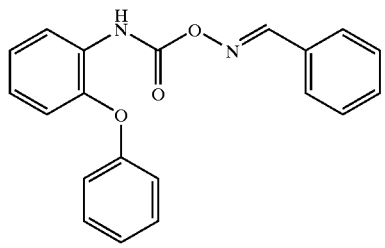

Benzaldehyde, O-[[(2-phenoxyphenyl)amino]carbonyl] oxime (Scheme 1B, Compound D') Prepared as described for the example above. Using work-up method C provided the title compound as white solid in 16% yield, mp 141.5–142.0° C. ¹H NMR (CDCl₃, 500 MHz) δ 8.73 (br, 1H), 8.32 (dd, J=1.3 Hz, J=8.2 Hz, 1H), 8.30 (s, 1H), 7.55–7.51 (m, 2H), 7.36 (t, J=8.7 Hz, 2H), 7.21 (t, J=7.8 Hz, 1H), 7.12 (t, J=7.4 Hz, 1H), 7.11–7.08 (m, 3H), 7.03 (d, J=8.7 Hz, 2H), 6.98 (d, J=1.4 Hz, J=8.1, 1H); ¹³C NMR (CDCl₃, 500 MHz) δ 156.8, 152.2, 145.0, 130.2, 130.1, 129.9, 129.4, 124.8, 124.1, 123.5, 119.9, 119.1, 117.4, 116.3, 116.2; Mass spec.: 351.0 (MH⁺); Anal. Calcd. for $C_{20}H_{15}FN_2O_3 \cdot 0.41H_2O$: C=67.15%, H=4.46%, N=7.83; found: C=67.13%, H=4.39%, N=7.76%.

EXAMPLE 91

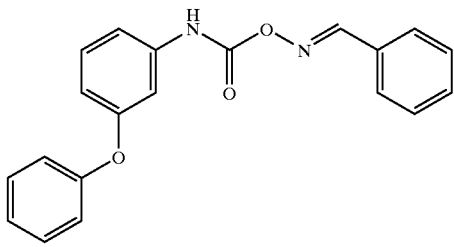

Benzaldehyde, O-[[(3-phenoxyphenyl)amino]carbonyl] oxime (Scheme 1B, Compound D') Prepared as described for the example above. Using work-up method C provided the title compound as gel-like material in 50% yield. $^1$H NMR (CDCl$_3$, 500 MHz) δ 8.39 (s, 1H), 8.11 (br, 1H), 7.70 (d, J=5.1 Hz, 2H), 7.53–7.45 (m, 3H), 7.37–7.28 (m, 4H), 7.24–7.23 (m 1H), 7.12 (t, J=7.4 Hz, 1H), 7.04 (m, J=7.7 Hz, 2H), 6.79–6.76 (m, 1H); $^{13}$C NMR (CDCl$_3$, 500 MHz) δ 158.0, 156.9, 153.9, 151.7, 138.3, 132.0, 130.2, 129.8, 129.6, 129.1, 128.9, 128.2, 123.5, 119.2, 119.1, 114.6, 114.4, 110.4; Mass spec.: 333.0 (MH$^+$); Anal. Calcd. for C$_{20}$H$_{16}$N$_2$O$_3$: C=72.28%, H=4.85%, N=8.43%; found: C=72.10%, H=4.72%, N=8.40%.

EXAMPLE 92

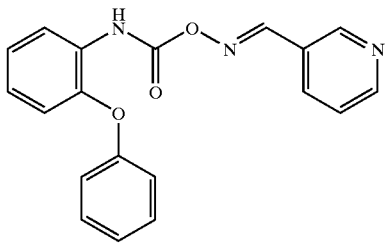

3-Pyridinecarboxaldehyde, O-[[(2-phenoxyphenyl)amino]carbonyl]oxime (Scheme 1B, Compound D') Prepared as described for the example above. Using work-up method C provided the title compound as white solid in 42% yield. $^1$H NMR (CDCl$_3$, 500 MHz) δ 13.26 (br, 1H), 8.91 (d, J=1.6 Hz, 1H), 8.81 (dd, J=1.4 Hz, J=5.2 Hz, 1H), 8.45 (s, 1H), 8.38 (br, 1H), 8.29–8.27 (m, 2H), 7.66 (dd, J=5.2 Hz, J=8.0 Hz, 1H), 7.37 (t, J=7.5 Hz, 2H), 7.20 (t, J=7.8 Hz, 1H), 7.15 (t, J=7.4 Hz, 1H), 7.08 (td, J=1.5 Hz, J=8.1 Hz, 1H), 7.04 (d, J=8.0 Hz, 1H), 6.95 (dd, J=1.3 Hz, J=8.1 Hz, 1H); $^{13}$C NMR (CDCl$_3$, 500 MHz) δ 16101, 160.7, 156.5, 150.6, 149.2, 147.9, 145.5, 145.3, 138.3, 130.1, 128.8, 128.5, 125.6, 124.7, 124.5, 123.8, 119.8, 118.7, 117.8, 116.7, 114.4; Mass spec.: 334.0 (MH$^+$); Anal. Calcd. for C$_{19}$H$_{15}$N$_3$O$_3$·0.185H$_2$O: C=67.78%, H=4.60%, N=12.48%; found: C=67.74%, H=4.46%, N=12.47%.

EXAMPLE 93

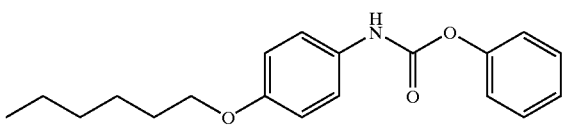

4-Hexyloxyphenylcarbamic acid, phenyl ester (Scheme 1B, Compound D") Prepared as described for the example above. Analytical HPLC 1.81 min. (99%). Mass Spec: 314 (MH+).

EXAMPLE 94

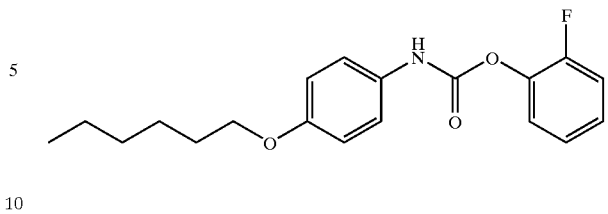

4-Hexyloxyphenylcarbamic acid, 2-fluorophenyl ester (Scheme 1B, Compound D") Prepared as described for the example above. Analytical HPLC 1.80 min. (97%). Mass Spec: 331.39 (MH+).

EXAMPLE 95

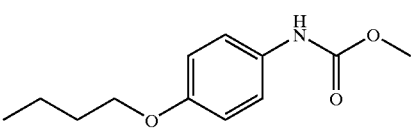

4-Butoxyphenylcarbamic acid, methyl ester (Scheme 1B, Compound D") Prepared as described for the example above. $^1$H NMR (DMSO-d$_6$) δ 9.40 (br. s, 1H), 7.32 (d, 2H, J=8.0 Hz), 6.83 (dd, 2H, J=7.5, 2.5 Hz), 3.89 (t, 2H, J=6.5 Hz), 1.65 (m, 2H), 1.40 (m, 2H), 0.92 (t, 3H, J=7.5 Hz). Analytical HPLC 1.51 min. (95%). Mass Spec: 224.15 (MH+).

EXAMPLE 96

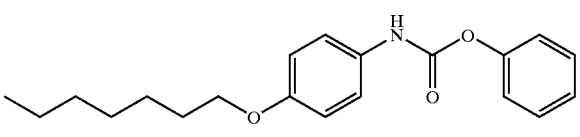

4-Heptyloxyphenylcarbamic acid, phenyl ester (Scheme 1B, Compound D") Prepared as described for the example above. Analytical HPLC 2.08 min. (91%). Mass Spec: 328.18 (MH+).

EXAMPLE 97

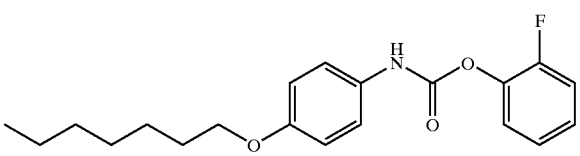

4-Heptyloxyphenylcarbamic acid, 2-fluorophenyl ester (Scheme 1B, Compound D") Prepared as described for the example above. Analytical HPLC 2.06 min. (99%). Mass Spec: 346.17 (MH+).

EXAMPLE 98

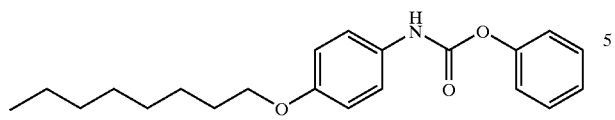

4-Octyloxyphenylcarbamic acid, phenyl ester (Scheme 1B, Compound D") Prepared as described for the example above. Analytical HPLC 1.97 min. (85%). Mass Spec: 342.29 (MH+).

EXAMPLE 99

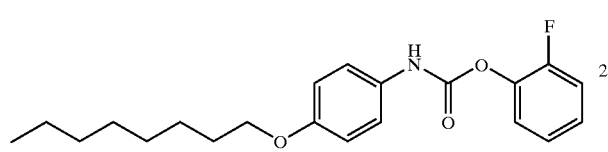

4-Octyloxyphenylcarbamic acid, 2-fluorophenyl ester (Scheme 1B, Compound D") Prepared as described for the example above. Analytical HPLC 1.64 min. (90%). Mass Spec: 360.26 (MH+).

EXAMPLE 100

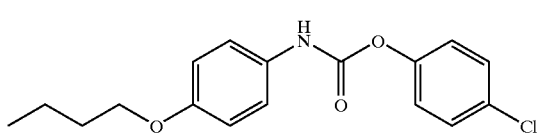

4-Butyloxyphenylcarbamic acid, 4-fluorophenyl ester (Scheme 1B, Compound D") Prepared as described for the example above. $^1$H NMR (DMSO-$d_6$) δ 7.47 (d, 2H, J=7.0 Hz), 7.38 (d, 2H, J=4.0 Hz), 7.25 (d, 2H, J=7.0 Hz), 6.90 (dd, 2H, J=6.0, 2.5 Hz), 3.92 (t, 2H, J=6.5 Hz), 1.72 (m, 2H), 1.40 (m, 2H), 0.92 (t, 3H, J=7.5 Hz); Analytical HPLC 1.90 min. (95%). Mass Spec: 320 (MH+).

EXAMPLE 101

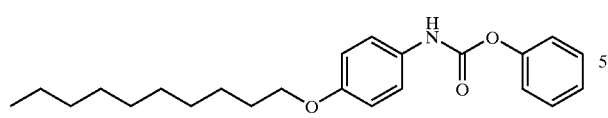

4-Decyloxyphenylcarbamic acid, phenyl ester (Scheme 1B, Compound D") Prepared as described for the example above. Analytical HPLC 2.09 min. (97%). Mass Spec: 370.38 (MH+).

EXAMPLE 102

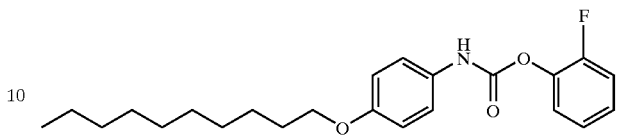

4-Decyloxyphenylcarbamic acid, 2-fluorophenyl ester (Scheme 1B, Compound D") Prepared as described for the example above. Analytical HPLC 2.07 min. (98%). Mass Spec: 388.43 (MH+).

EXAMPLE 103

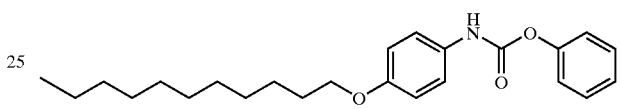

4-Undecyloxyphenylcarbamic acid, phenyl ester (Scheme 1B, Compound D") Prepared as described for the example above. Analytical HPLC 2.33 min. (93%). Mass Spec: 384.26 (MH+).

EXAMPLE 104

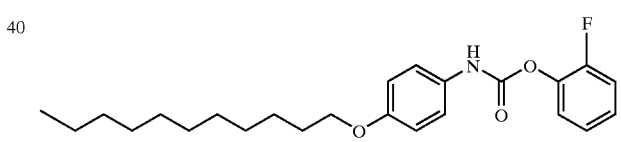

4-Undecyloxyphenylcarbamic acid, 2-fluorophenyl ester (Scheme 1B, Compound D") Prepared as described for the example above. Analytical HPLC 2.31 min. (96%). Mass Spec: 402.25 (MH+).

EXAMPLE 105

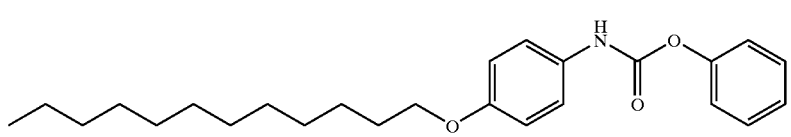

4-Dodecyloxyphenylcarbamic acid, phenyl ester (Scheme 1B, Compound D") Prepared as described for the example above. Analytical HPLC 2.18 min. (85%). Mass Spec: 398.36 (MH+).

EXAMPLE 106

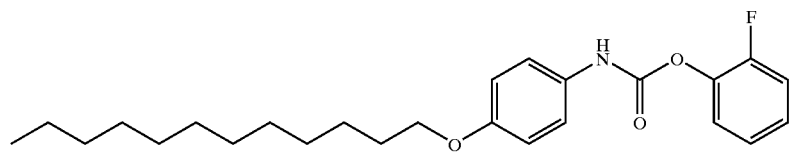

4-Dodecyloxyphenylcarbamic acid, 2-fluorophenyl ester (Scheme 1B, Compound D") Prepared as described for the example above. Analytical HPLC 2.18 min. (95%). Mass Spec: 416.38 (MH+).

EXAMPLE 107

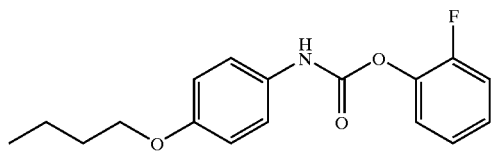

4-Butoxyphenylcarbamic acid, 2-fluorophenyl ester (Scheme 1B, Compound D") Prepared as described for the example above. Analytical HPLC 1.61 min. (97%). Mass Spec: 304.18 (MH+).

EXAMPLE 108

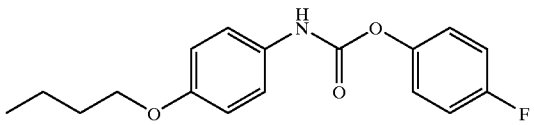

4-Butoxyphenylcarbamic acid, 4-fluorophenyl ester (Scheme 1B, Compound D") Prepared as described for the example above. $^1$H NMR (DMSO-$d_6$) δ 7.33 (d, 2H, J=8.1 Hz), 7.23 (m, 4H), 6.90 (dd, 2H, J=7.0, 2.5 Hz), 3.92 (t, 2H, J=6.5 Hz), 1.72 (m, 2H), 1.42 (m, 2H), 0.91 (t, 3H, J=7.0 Hz). Analytical HPLC 1.65 min. (95%). Mass Spec: 304.18 (MH+).

EXAMPLE 109

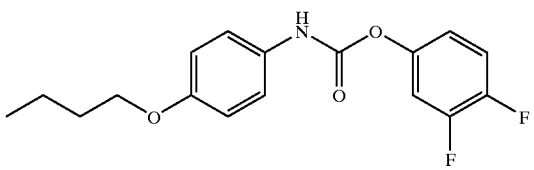

4-Butoxyphenylcarbamic acid, 3,4-difluorophenyl ester (Scheme 1B, Compound D") Prepared as described for the example above. Analytical HPLC 1.71 min. (97%). Mass Spec: 322 (MH+).

EXAMPLE 110

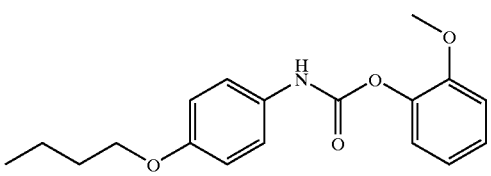

4-Butoxyphenylcarbamic acid, 2-methoxyphenyl ester (Scheme 1B, Compound D") Prepared as described for the example above. Analytical HPLC 1.57 min. (97%). Mass Spec: 316.18 (MH+).

EXAMPLE 111

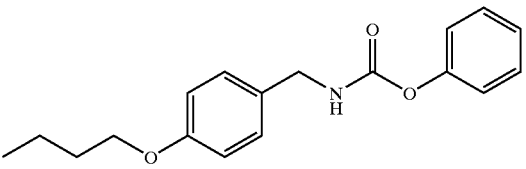

4-(Butoxyphenylmethyl)carbamic acid, phenyl ester (Scheme 1B, Compound D") Prepared as described for the example above. Analytical HPLC 1.59 min. (95%). Mass Spec: 300.0 (MH+).

EXAMPLE 112

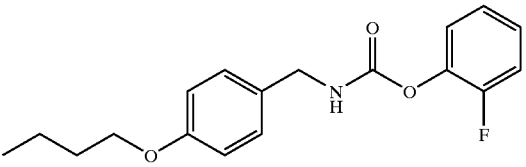

4-(Butoxyphenylmethyl)carbamic acid, 2-fluorophenyl ester (Scheme 1B, Compound D") Prepared as described for the example above. $^1$H NMR (DMSO-$d_6$) δ 9.40 (br. s, 1H), 7.26 (m, 6H), 6.90 (d, 2H, J=8.4 Hz), 4.19 (d, 2H, J=6.0 Hz), 3.92 (t, 2H, J=6.5 Hz), 1.67 (m, 2H), 1.42 (m, 2H), 0.91 (t, 3H, J=7.0 Hz). Analytical HPLC 1.59 min. (95%). Mass Spec: 318 (MH+).

EXAMPLE 113

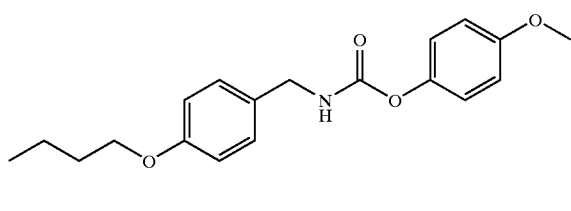

4-(Butoxyphenylmethyl)carbamic acid, 4-methoxyphenyl ester (Scheme 1B, Compound D") Prepared as described for the example above. Analytical HPLC 1.60 min. (95%). Mass Spec: 330.25 (MH+).

EXAMPLE 114

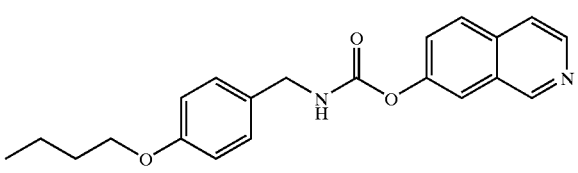

4-(Butoxyphenylmethyl)carbamic acid, 6-quinolinyl ester (Scheme 1B, Compound D") Prepared as described for the example above. Analytical HPLC 1.30 min. (95%). Mass Spec: 351.25 (MH+).

EXAMPLE 115

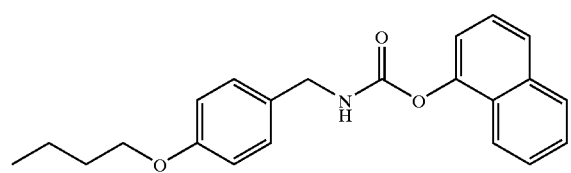

4-(Butoxyphenylmethyl)carbamic acid, 1-naphthalenyl ester (Scheme 1B, Compound D") Prepared as described for the example above. Analytical HPLC 1.77 min. (95%). Mass Spec: 350 (MH+).

EXAMPLE 116

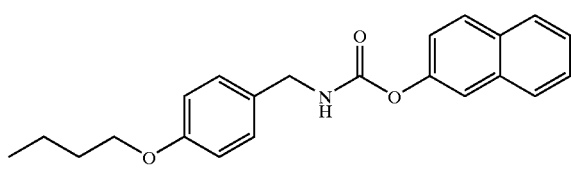

4-(Butoxyphenylmethyl)carbamic acid, 2-naphthalenyl ester (Scheme 1B, Compound D") Prepared as described for the example above. Analytical HPLC 1.80 min. (98%). Mass Spec: 350.26 (MH+).

EXAMPLE 117

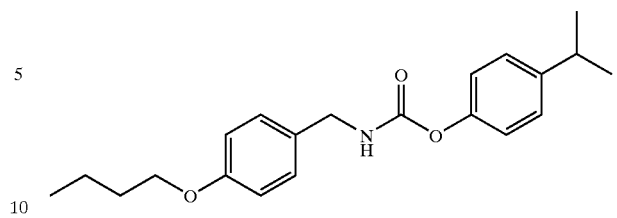

4-(Butoxyphenylmethyl)carbamic acid, 4-(1-methylethyl)phenyl ester (Scheme 1B, Compound D") Prepared as described for the example above. Analytical HPLC 1.82 min. (95%). Mass Spec: 342 (MH+).

EXAMPLE 118

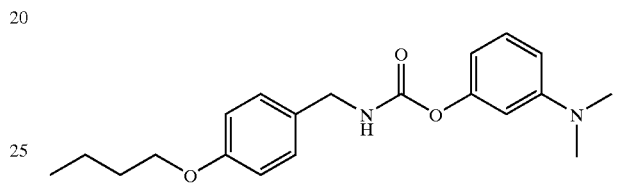

4-(Butoxyphenylmethyl)carbamic acid, 3-(dimethylamino)phenyl ester (Scheme 1B, Compound D") Prepared as described for the example above. Analytical HPLC 1.32 min. (90%). Mass Spec: 343.29 (MH+).

EXAMPLE 119

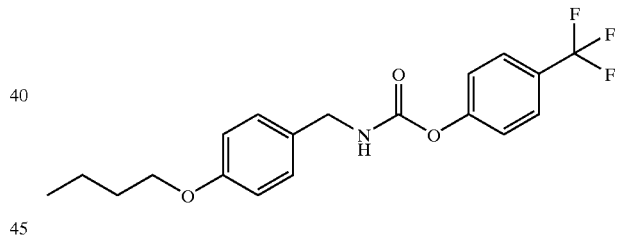

4-(Butoxyphenylmethyl)carbamic acid, 4-(trifluoromethyl)phenyl ester (Scheme 1B, Compound D") Prepared as described for the example above. Analytical HPLC 1.77 min. (99%). Mass Spec: 368.14 (MH+).

EXAMPLE 120

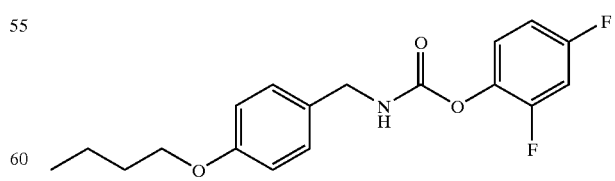

4-(Butoxyphenylmethyl)carbamic acid, 2,4-difluorophenyl ester (Scheme 1B, Compound D") Prepared as described for the example above. Analytical HPLC 1.66 min. (99%). Mass Spec: 336.14 (MH+).

EXAMPLE 121

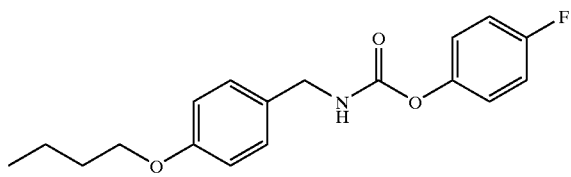

4-(Butoxyphenylmethyl)carbamic acid, 4-fluorophenyl ester (Scheme 1B, Compound D") Prepared as described for the example above. Analytical HPLC 1.61 min. (85%). Mass Spec: 318.15 (MH+).

EXAMPLE 122

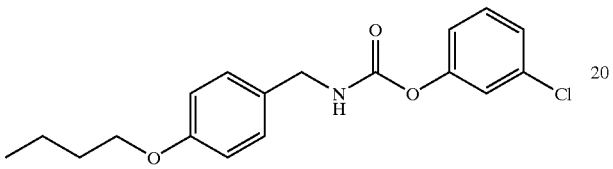

4-(Butoxyphenylmethyl)carbamic acid, 3-chlorophenyl ester (Scheme 1B, Compound D") Prepared as described for the example above. Analytical HPLC 1.72 min. (86%). Mass Spec: 334.12 (MH+).

EXAMPLE 123

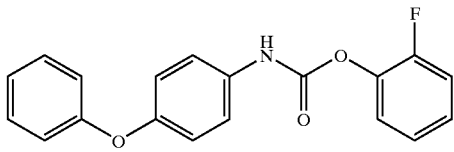

4-Phenoxyphenylcarbamic acid, 2-fluorophenyl ester (Scheme 1B, Compound D') Prepared as described for the example above. Using work-up method C provided the title compound as white solid in 11% yield. $^1$H NMR (CDCl$_3$, 400 MHz) δ 7.43 (br, 1H), 7.41 (br, 1H), 7.35–7.30 (m, 2H), 7.28–7.13 (m, 4H), 7.09 (dt, J=0.9 Hz, J=7.4 Hz, 1H), 7.03–6.97 (m, 5H); (s, 1H), 8.06 (s, 1H), 7.76–7.73 (m, 2H), 7.59 (m, 4H), 7.52–7.50 (m, 2H), 7.27 (d, J=8.2 Hz, 2H), 7.18 (t, J=8.6 Hz, 2H), 2.70 (q, J=7.6 Hz, 2H), 1.28 (t, J=7.6 Hz, 3H); $^{13}$C NMR (CDCl$_3$, 400 MHz) δ 153.6, 129.8, 129.7, 127.0, 126.9, 124.4, 124.1, 123.1, 120.5, 119.8, 119.6, 118.6, 118.5, 116.8, 116.7; Anal. Calcd. for C$_{19}$H$_{14}$FNO$_3$: C=70.58%, H=4.36%, N=4.33%; found: C=70.54%, H=4.31%, N=4.21%.

EXAMPLE 124

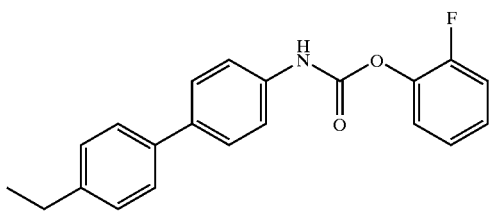

4'-Ethyl-[1,1'-biphenyl]-4-ylcarbamic acid, 2-fluorophenyl ester (Scheme 1B, Compound D') Prepared as described for the example above. Using work-up method B provided the title compound as white solid in 30% yield. $^1$H NMR (CDCl$_3$, 400 MHz) δ 7.57–7.55 (m, 2H), 7.52–7.49 (m, 4H), 7.36–7.33 (m, 1H), 7.30–7.27 (m, 2H), 7.25–7.14 (m, 3H), 7.05 (br, 1H), 2.70 (q, J=7.6 Hz, 2H), 1.28 (t, J=7.6 Hz, 3H); Anal. Calcd. for C$_{21}$H$_{18}$FNO$_2$: C=75.21%, H=5.41%, N=4.18%; found: C=75.27%, H=5.40%, N=4.25%.

Scheme 2:

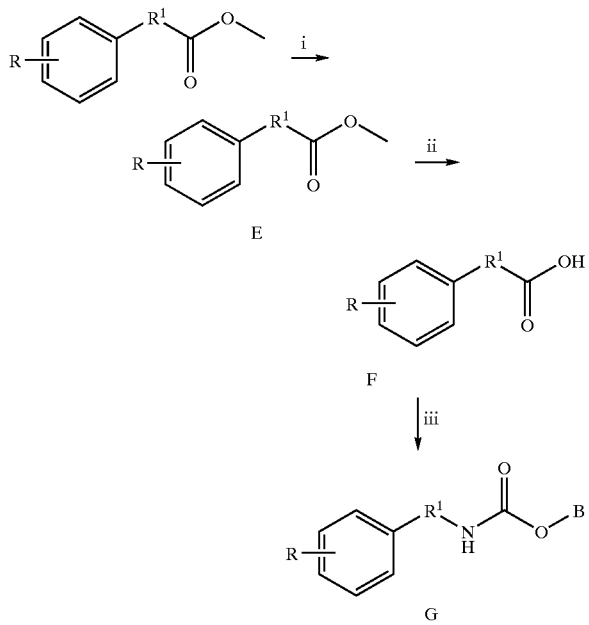

Scheme 2 Reaction conditions: (i) R$^1$-halide, NaH, DMF, 50° C.; (ii) NaOH, EtOH, room temp.; (iii) (a) N$_3$P(O)(OPh)$_2$, Et$_3$N, toluene at 105° C., (b) B—OH at 80° C.; R, R$^1$ and B are as defined above.

The following Intermediates 40 to 41 may be used to synthesize Examples 125 to 135.

INTERMEDIATE 40

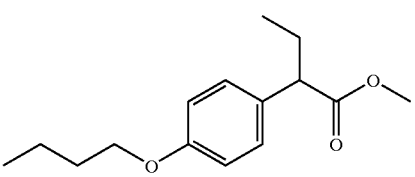

2-(4-Butoxy-phenyl)-butyric acid methyl ester: (Scheme 2, Compound E) The mixture of methyl 4-butoxyphenylacetate (1.20 g, 5.4 mmol) and NaH (60% in mineral oil, 0.50 g, 12.5 mmol) in DMF (25.0 mL) was stirred at 50° C. for 40 min. Bromoethane (2.0 g, 18.3 mmol) was added and the stirring continued at rt for one hour. The reaction mixture was diluted with EtOAc (300 mL), washed with H$_2$O, and then was dried over Na$_2$SO$_4$. After filtration and concentration in vacuo, the residue was purified by flash chromatography (SiO$_2$: EtOAc/Hexanes). This compound was obtained as a yellow oil (0.85 g, 3.4 mmol, 63% yield). $^1$H NMR (DMSO-d$_6$) δ 7.16 (d, 2H, J=7.0 Hz), 6.87 (d, 2H, J=8.5 Hz), 3.92 (t, 2H, J=6.5 Hz), 3.55 (s, 3H), 3.45 (t, 1H, J=9.0), 1.93 (m, 1H), 1.63 (m, 2H), 1.42 (m, 2H), 0.97 (t, 3H, J=7.2 Hz), 0.79 (t, 3H, J=4.0 Hz).

INTERMEDIATE 41

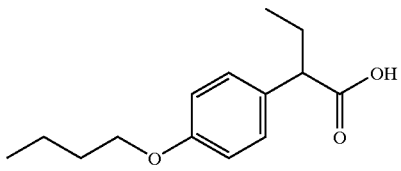

2-(4-Butoxy-phenyl)-butyric acid: (Scheme 2, Compound F) To a solution of 2-(4-butoxy-phenyl)-butyric acid methyl ester (2.0 g, 8.0 mmol) in EtOH (30 mL) was added NaOH (10 N, 6 mL, 60 mmol). The resulting mixture was stirred at rt for 3 hours, diluted with H₂O (30 mL), acidified to pH~1.0 using HCl (6N). The precipitates were filtered off by filter paper, washed by H₂O and hexanes. This compound was obtained as a white solid. (1.4 g, 5.9 mmol, 74% yield). $^1$H NMR (DMSO-$d_6$) δ 12.20 (br. s, 1H), 7.16 (d, 2H, J=7.0 Hz), 6.87 (d, 2H, J=8.5 Hz), 3.92 (t, 2H, J=6.5 Hz), 3.31 (t, 2H, J=6.9 Hz), 1.93 (m, 1H), 1.63 (m, 3H), 1.42 (m, 2H), 0.97 (t, 3H, J=7.2 Hz), 0.79 (t, 3H, J=4.0 Hz).

EXAMPLE 125

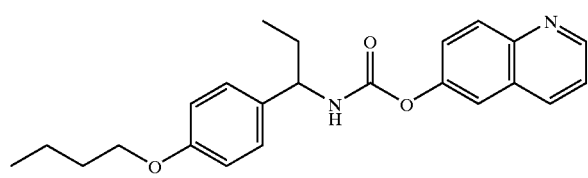

[1-(4-Butoxy-phenyl)-propyl]-carbamic acid quinolin-6-yl ester (Scheme 2, Compound G) To a solution of 2-(4-butoxy-phenyl)-butyric acid (0.050 g, 0.23 mmol) and Et₃N (0.053 g, 0.53 mmol) in toluene (2 mL) was added diphenylphosphoryl azide (0.096 g, 0.35 mmol). The resultant mixture was stirred at r.t. for 10 min. and then at 107° C. under N₂ for 60 min. After the mixture was cooled to r.t., quinolin-6-ol (0.050 g, 0.34 mmol) was added. The reaction mixture was stirred at r.t. for 10 min. and then at 80° C. for 1 h. The mixture was diluted with EtOAc, washed with H₂O. After filtration and concentration in vacuo, the residue was purified by by preparative HPLC (YMC 30×100 mm (5 uM packing), 10% MeOH/90% water/01% TFA as mobile phase A, 90% MeOH/10% water/0.1% TFA as mobile phase B). This compound was obtained as a pale yellow solid (0.040 g, 0.11 mmol, 46% yield): mp 115–118° C.; $^1$H NMR (DMSO-$d_6$) δ 8.93 (m, 1H), 8.45 (d, 1H, J=9.0 Hz), 8.40 (d, 1H, J=8.5), 8.02 (d, 1H, J=9.0 Hz), 7.77 (s, 1H), 7.62 (dd, 1H, J=8.5, 4.5 Hz), 7.55 (dd, 1H, J=9.0, 2.5 Hz), 7.25 (d, 2H, J=8.5 Hz), 6.98 (d, 2H, J=8.5 Hz), 4.43 (m, 1H), 3.95 (t, 2H, J=6.5 Hz), 1.75 (m, 1H), 1.65 (m, 3H), 1.42 (m, 2H), 0.90 (m, 6H). Mass Spec: 379.33 (MH⁺).

EXAMPLE 126

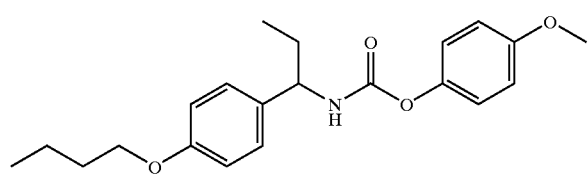

[1-(4-Butoxy-phenyl)-propyl]-carbamic acid 4-methoxy-phenyl ester (Scheme 2, Compound G) Prepared as described for the example above. Analytical HPLC 1.73 min. (88%). Mass Spec: 358.25 (MH+).

EXAMPLE 127

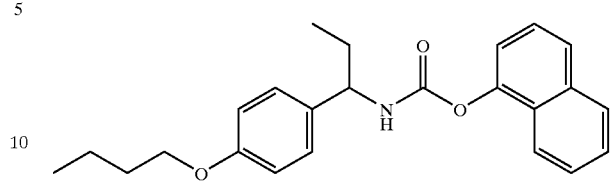

[1-(4-Butoxy-phenyl)-propyl]-carbamic acid naphthalen-1-yl ester (Scheme 2, Compound G) Prepared as described for the example above. Analytical HPLC 1.86 min. (98%). Mass Spec: 378.25 (MH+).

EXAMPLE 128

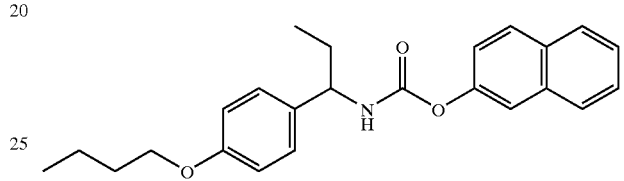

[1-(4-Butoxy-phenyl)-propyl]-carbamic acid naphthalen-2-yl ester (Scheme 2, Compound G) Prepared as described for the example above. $^1$H NMR (DMSO-$d_6$) δ 8.30 (d, 1H, J=9.0 Hz), 7.90 (m, 3H), 7.60 (s, 1H), 7.45 (m, 2H), 7.25 (m, 3H), 6.90 (d, 2H, J=8.5 Hz), 4.43 (m, 1H), 3.95 (t, 2H, J=6.5 Hz), 1.75 (m, 1H), 1.65 (m, 3H), 1.42 (m, 2H), 0.90 (m, 6H). Analytical HPLC 1.87 min. (99%). Mass Spec: 378.12 (MH+).

EXAMPLE 129

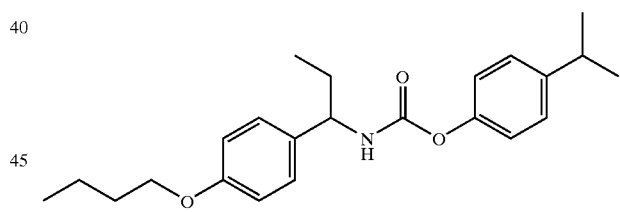

[1-(4-Butoxy-phenyl)-propyl]-carbamic acid 4-isopropyl-phenyl ester (Scheme 2, Compound G) Prepared as described for the example above. Analytical HPLC 1.91 min. (96%). Mass Spec: 370.31 (MH+).

EXAMPLE 130

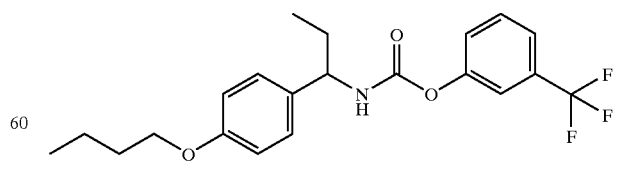

[1-(4-Butoxy-phenyl)-propyl]-carbamic acid 3-trifluoromethyl-phenyl ester (Scheme 2, Compound G) Prepared as described for the example above. Analytical HPLC 1.84 min. (96%). Mass Spec: 396.18 (MH+).

EXAMPLE 131

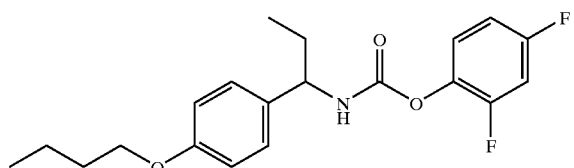

[1-(4-Butoxy-phenyl)-propyl]-carbamic acid 2,4-difluoro-phenyl ester (Scheme 2, Compound G) Prepared as described for the example above. Analytical HPLC 1.77 min. (89%). Mass Spec: 364.17 (MH+).

EXAMPLE 132

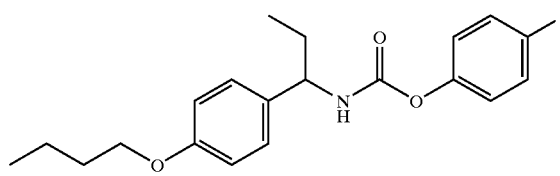

[1-(4-Butoxy-phenyl)-propyl]-carbamic acid 4-fluoro-phenyl ester (Scheme 2, Compound G) Prepared as described for the example above. Analytical HPLC 1.72 min. (89%). Mass Spec: 346.18 (MH+).

EXAMPLE 133

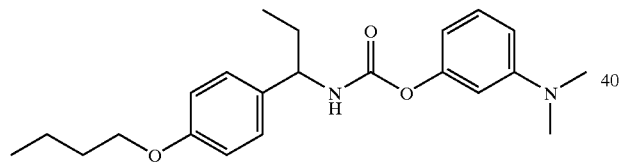

[1-(4-Butoxy-phenyl)-propyl]-carbamic acid 4-dimethylamino-phenyl ester (Scheme 2, Compound G) Prepared as described for the example above. Analytical HPLC 1.53 min. (96%). Mass Spec: 371 (MH+).

EXAMPLE 134

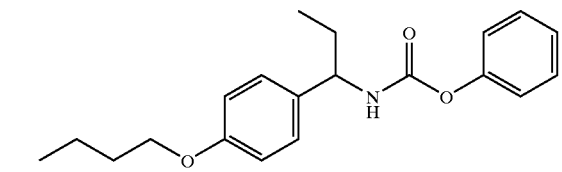

[1-(4-Butoxy-phenyl)-propyl]-carbamic acid phenyl ester (Scheme 2, Compound G) Prepared as described for the example above. Analytical HPLC 1.70 min. (88%). Mass Spec: 328.19 (MH+).

EXAMPLE 135

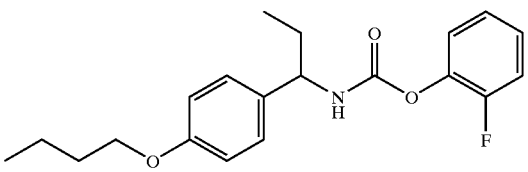

[1-(4-Butoxy-phenyl)-propyl]-carbamic acid 2-fluoro-phenyl ester (Scheme 2, Compound G) Prepared as described for the example above. Analytical HPLC 1.70 min. (89%). Mass Spec: 346.18 (MH+).

Scheme 3:

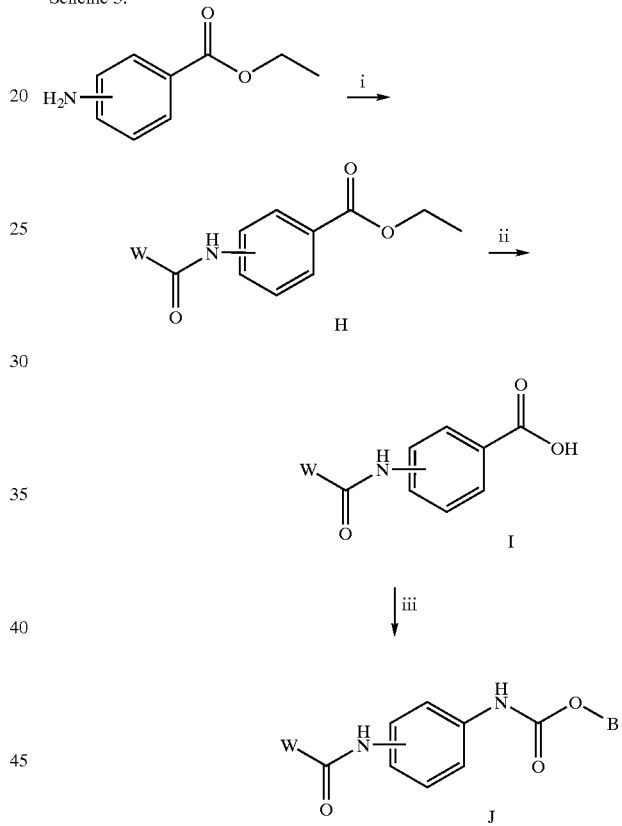

Scheme 3 Reaction conditions: (i) W-acid chloride, Et$_3$N, dichloroethane, room temp.; (ii) NaOH, EtOH, room temp.; (iii) (a) N$_3$P(O)(OPh)$_2$, Et$_3$N, toluene at 105° C., (b) B—OH at 80° C.; W is C$_{1-12}$ alkyl and B is as defined above.

The following Intermediates 42 and 43 may be used to synthesize Examples 136 to 140.

INTERMEDIATE 42

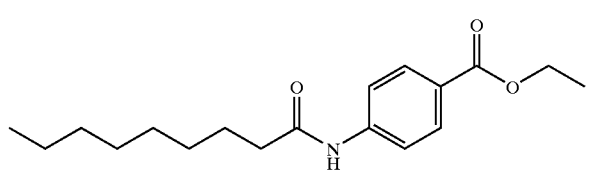

4-Decanoylamino-benzoic acid ethyl ester: (Scheme 3, Compound H) To a solution of 4-amino-benzoic acid ethyl ester (2.0 g, 12.1 mmol) and decanoyl chloride (2.35 g, 13.3 mmol) in methylene chloride (20 mL) was added Et₃N (1.34 g, 13.3 mmol). The resultant mixture was stirred at room temperature for one hour and then was diluted with EtOAc, washed by H₂O, dried over MgSO₄. After filtration and concentration in vacuo, the product was directly used in the next step.

INTERMEDIATE 43

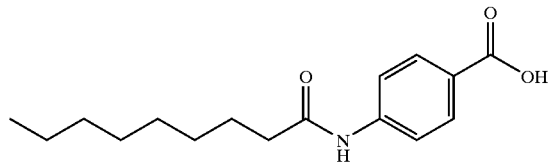

4-Decanoylamino-benzoic acid: (Scheme 3, Compound I) To a solution of 4-decanoylamino-benzoic acid ethyl ester (2.0 g, 6.6 mmol) in EtOH (30 mL) was added NaOH (10 N, 6 mL, 60 mmol). The resulting mixture was stirred at rt for 3 hours, diluted with H₂O (30 mL), acidified to pH~1.0 using HCl (6N). The precipitates were filtered off by filter paper, washed by H₂O and hexanes. This compound was obtained as a white solid. (1.8 g, 6.5 mmol, 98% yield). ¹H NMR (DMSO-d₆) δ 9.91 (br. s, 1H), 7.76 (d, 2H, J=8.7 Hz), 6.50 (d, 2H, J=8.7 Hz), 2.29 (t, 2H, J=7.5 Hz), 1.57 (m, 2H), 1.25 (m, 12H), 0.85 (t, 3H, J=6.9 Hz). Mass Spec: 278.21 (MH⁺).

EXAMPLE 136

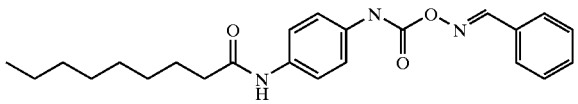

Benzaldehyde, O-[[(4-Nonanoylamino-phenyl)amino]carbonyl]oxime (Scheme 3, Compound J) To a solution of 4-decanoylamino-benzoic acid (0.050 g, 0.18 mmol) and Et₃N (0.053 g, 0.53 mmol) in toluene (2 mL) was added diphenylphosphoryl azide (0.096 g, 0.35 mmol). The resultant mixture was stirred at r.t. for 10 min. and then at 107° C. under N₂ for 60 min. After the mixture was cooled to r.t., benzaldehyde oxime (0.050 g, 0.41 mmol) was added. The reaction mixture was stirred at r.t. for 10 min. and then at 80° C. for 30 min. The mixture was diluted with EtOAc, washed with H₂O. After filtration and concentration in vacuo, the residue was purified by preparative HPLC (YMC 30×100 mm (5 uM packing), 10% MeOH/90% water/01% TFA as mobile phase A, 90% MeOH/10% water/0.1% TFA as mobile phase B). This compound was obtained as a pale yellow solid (0.038 g, 0.10 mmol, 53% yield): ¹H NMR (DMSO-d₆) δ 9.78 (d, 2H, J=9.0 Hz), 8.63 (s, 1H), 7.82 (dd, 2H, J=7.7, 2.4 Hz), 7.52 (m, 5H), 7.44 (d, 2H, J=9.0 Hz), 2.27 (t, 2H, J=9.0 Hz), 1.55 (m, 2H), 1.26 (m, 10H), 0.85 (t, 3H, J=6.6 Hz). Mass Spec: 396.22 (MH⁺).

EXAMPLE 137

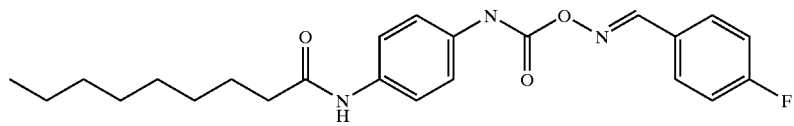

4-Fluorobenzaldehyde, O-[[(4-Nonanoylamino-phenyl)amino]carbonyl]oxime (Scheme 3, (Compound J) Prepared as described for the example above. ¹H NMR (DMSO-d₆) δ 9.78 (d, 2H, J=9.0 Hz), 8.63 (s, 1H), 7.82 (dd, 2H, J=8.7, 5.4 Hz), 7.52 (d, 2H, J=9.0 Hz), 7.32 (m, 4H), 2.27 (t, 2H, J=9.0 Hz), 1.55 (m, 2H), 1.26 (m, 10H), 0.85 (t, 3H, J=6.6 Hz). Anal. Calcd for C₂₃H₂₈FN₃O₃: C, 66.81; H, 6.82; N, 10.16. Found: C, 67.07, H, 6.82; N, 10.09. Mass Spec: 414.21 (MH+).

EXAMPLE 138

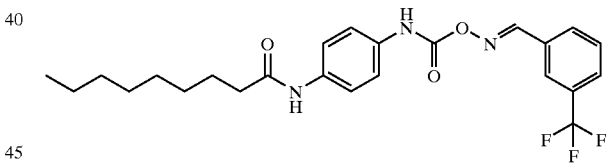

3-Trifluoromethylbenzaldehyde, O-[[(4-Nonanoylaminophenyl)amino]carbonyl]oxime (Scheme 3, Compound J) Prepared as described for the example above. ¹H NMR (DMSO-d₆) δ 9.78 (d, 2H, J=9.0 Hz), 8.63 (s, 1H), 8.15 (m, 2H), 7.92 (d, 1H, J=9.0 Hz), 7.80 (t, 1H, J=7.5 Hz), 7.52 (d, 2H, J=9.0 Hz), 7.32 (d, 2H, J=9.0 Hz) 2.27 (t, 2H, J=9.0 Hz), 1.55 (m, 2H), 1.26 (m, 10H), 0.85 (t, 3H, J=6.6 Hz). Anal. Calcd for C₂₄H₂₈F₃N₃O₃: C, 62.19; H, 6.08; N, 9.06. Found: C, 62.45, H, 6.12; N, 8.99. Mass Spec: 464.21 (MH+).

EXAMPLE 139

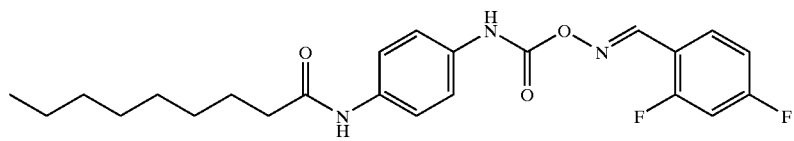

2,4-Difluorobenzaldehyde, O-[[(4-Nonanoylamino-phenyl)amino]carbonyl]oxime (Scheme 3, Compound J) Prepared as described for the example above. ¹H NMR (DMSO-d₆) δ 9.78 (s, 2H), 8.63 (s, 1H), 8.05 (m, 1H), 7.52 (m, 4H), 7.22 (m, 1H), 2.27 (t, 2H, J=9.0 Hz), 1.55 (m, 2H), 1.26 (m, 10H), 0.85 (t, 3H, J=6.6 Hz). Mass Spec: 432.20 (MH+).

EXAMPLE 140

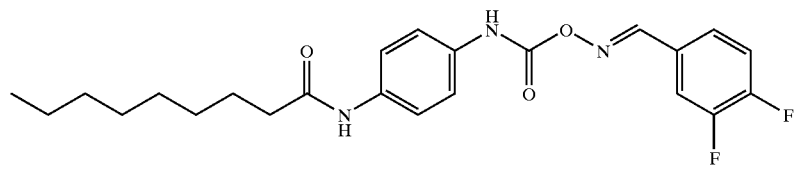

3,4-Difluorobenzaldehyde, O-[[(4-Nonanoylamino-phenyl)amino]carbonyl]oxime (Scheme 3, Compound J) Prepared as described for the example above. ¹H NMR (DMSO-d₆) δ 9.78 (d, 2H, J=8.1 Hz), 8.63 (s, 1H), 8.00 (m, 1H), 7.72–7.42 (m, 6H), 2.27 (t, 2H, J=9.0 Hz), 1.55 (m, 2H), 1.26 (m, 10H), 0.85 (t, 3H, J=6.6 Hz). Mass Spec: 432.20 (MH+).

Scheme 4:

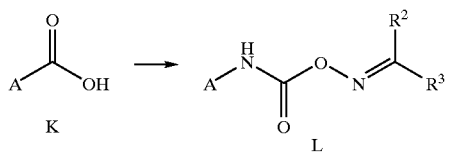

Scheme 4 Reaction conditions: (i) (a) Et₃N, DPPA/toluene, room temp. to 120° C., (b) oxime, room temp. to 85° C.; A is indolyl wherein K is the corresponding indole carboxylic acid, pyridyl wherein K is the corresponding pyridyl carboxylic acid, or benzofuranyl wherein K is the dibenzofurancarboxylic acid.

Examples 141 to 145 were made accordingly.

EXAMPLE 141

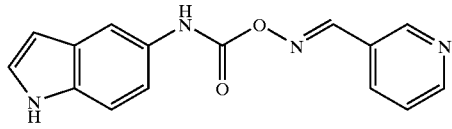

3-Pyridinecarboxaldehyde, O-[[(1H-indol-5-yl)amino] carbonyl]oxime (Scheme 4, Compound L) To a suspension of indole-5-carboxylic acid (commercially available) (1 mmol) in toluene was added triethylamine (4.0 mmol) and diphenylphosphoryl azide (DPPA) (1.2 mmol) subsequently at room temperature under nitrogen atmosphere. The resultant was stirred for 15 minutes at room temperature followed by 90 minutes at reflux. The reaction mixture was cooled down to room temperature followed by the addition of the corresponding oxime, 3-pyridinealdoxime, (1 mmol). The resultant was stirred for 1 hour at room temperature or followed by heating up to 85° C. Using work-up method A: filtration of the reaction mixture, and the solid was recrystallized from EtOAc/hexanes, provided the title compound as a white solid in 57% yield. ¹H NMR (DMSO, 500 MHz) δ 10.99 (s, 1H), 9.68 (s, 1H), 8.94 (d, J=1.7 Hz, 1H), 8.68–8.66 (m, 2H), 8.25 (dt, J=7.9 Hz, J=1.8 Hz, 1H), 7.66 (br, 1H), 7.53 (dd, J=4.8 Hz, J=8.0 Hz, 1H), 7.35 (d, J=8.6 Hz, 1H), 7.31 (t, J=2.8 Hz, 1H), 7.16 (dd, J=1.8 Hz, J=8.6 Hz, 1H), 6.40 (s, 1H); Mass spec.: 281.1 (MH⁺); Anal. Calcd. for C₁₅H₁₂N₄O₂: C=64.28%, H=4.32%, N=19.99%; found: C=64.09%, H=4.45%, N=19.759%.

EXAMPLE 142

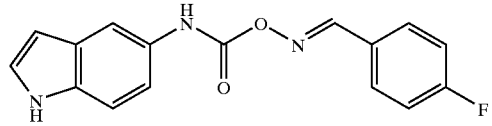

4-Fluorobenzaldehyde, O-[[(1H-indol-5-yl)amino] carbonyl]oxime (Scheme 4, Compound L) Prepared as described above. Using work-up method C: after removal of solvent, the residue was dissolved in methanol and filtrated, the filtrate was purified by preparative HPLC with methanol:H₂O (30:70 to about 100:0 v/v, containing 1% TFA) as a mobile phase to provide the title compound as white solid in 19% yield. ¹H NMR (DMSO, 500 MHz) δ 11.03 (s, 1H), 9.59 (s, 1H), 8.64 (s, 1H), 7.93 (dd, J=5.6 Hz, J=8.8 Hz, 2H), 7.69 (br, 1H), 7.38–7.32 (m, 3H), 7.20 (dd, J=1.8 Hz, J=8.7 Hz, 1H), 6.39 (t, J=2.0 Hz, 1H); Mass spec.: 298.0 (MH⁺); Anal. Calcd. for C₁₆H₁₂N₃O₂F.0.51H₂O: C=62.713%, H=4.28%, N=13.71%; found: C=62.73%, H=4.13%, N=14.02%.

EXAMPLE 143

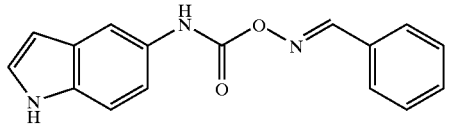

Benzaldehyde, O-[[(1H-indol-5-yl)amino]carbonyl] oxime (Scheme 4, Compound L) Prepared as described above. Using work-up method C provided the title compound as white solid in 20% yield. ¹H NMR (CDCl₃, 500 MHz) δ 8.43 (s, 1H), 8.19 (br, 1H), 8.15 (br, 1H), 7.82 (br, 1H), 7.74 (d, J=6.8 Hz, 2H), 7.54–7.46 (m, 3H), 7.38 (d, J=8.6 Hz, 1H), 7.29 (dd, J=1.8 Hz, J=8.7 Hz, 1H), 7.24 (t, J=2.7 Hz, 1H), 6.55 (t, J=2.2 Hz, 1H); Mass spec.: 280.0 (MH⁺); Anal. Calcd. for C₁₆H₁₃N₃O₂.0.16H₂O: C=68.11%, H=4.76%, N=14.89%; found: C=68.15%, H=4.77%, N=14.75%.

EXAMPLE 144

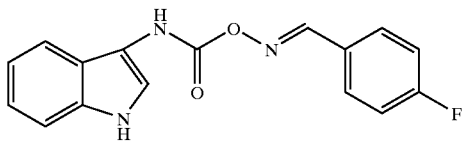

4-Fluorobenzaldehyde, O-[[(1H-indol-3-yl)amino]carbonyl]oxime (Scheme 4, Compound L) Prepared as described above. Using workup method C and then B provided the title compound as light blue solid in 20% yield. $^1$H NMR (DMSO, 500 MHz) δ 10.91 (s, 1H), 9.59 (s, 1H), 8.66 (s, 1H), 7.93 (t, J=5.7 Hz, 1H), 7.66 (d, J=7.9 Hz, 1H), 7.44 (m, 1H), 7.36 (t, J=8.1 Hz, 2H), 7.25 (m, 1H), 7.10 (t, J=8.1 Hz, 1H), 7.0 (t, J=7.7 Hz, 1H).

EXAMPLE 145

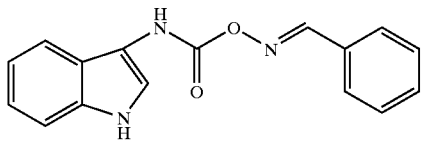

Benzaldehyde, O-[[(1H-indol-3-yl)amino]carbonyl]oxime (Scheme 4, Compound L) Prepared as described above. Using work-up method C and then B (after removal of the solvent, the residue was chromatographed by silica gel column packed with EtOAc/hexanes or EtOAc/dichloromethane) provided the title compound as a light blue solid in 11% yield. $^1$H NMR (CDCl$_3$, 500 MHz) δ 8.45 (s, 1H), 8.15 (br, 1H), 8.05 (br, 1H), 7.75 (d, J=6.9 Hz, 2H), 7.62 (d, J=1.5 Hz, 1H), 7.57 (d, J=8.0 Hz, 1H), 7.55–7.48 (m, 3H), 7.39 (d, J=8.2 Hz, 1H), 7.25 (t, J=8.0 Hz, 1H), 7.18 (t, J=7.9 Hz, 1H); Mass spec.: 280.0 (MH$^+$). Anal. Calcd. for C$_{16}$H$_{13}$N$_3$O$_2$.0.21H$_2$O: C=67.89%, H=4.78%, N=14.84%; found: C=67.91%, H=4.94%, N=14.17%.

EXAMPLE 146

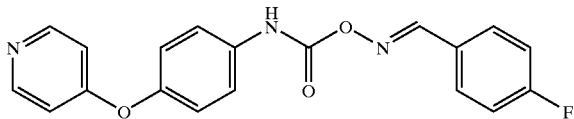

4-Fluorobenzaldehyde, O-[[[4-[(4-pyridinyl)oxy]phenyl]amino]carbonyl]oxime (Scheme 4, Compound L) Prepared as described above. Using work-up method B provided the title compound as light blue solid in 29% yield. $^1$H NMR (CDCl$_3$, 500 MHz) δ 8.47 (d, J=6.0 Hz, 2H), 8.40 (s, 1H), 8.15 (br, 1H), 7.74 (dd, J=8.05 Hz, J=11.55 Hz, 2H) 7.6 (d, J=8.9 Hz, 2H), 7.17 (t, J=8.55 Hz, 2H), 7.11 (d, J=8.9 Hz, 2H), 6.86 (dd, J=1.5 Hz, J=4.8 Hz, 2H); Mass spec.: 352.34 (MH$^+$).

EXAMPLE 147

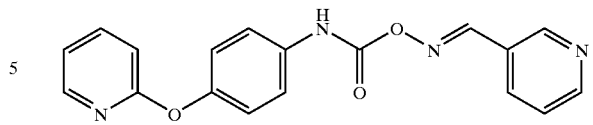

3-Pyridinecarboxaldehyde, O-[[[4-[(2-pyridinyl)oxy]phenyl]amino]carbonyl]oxime (Scheme 4, Compound L) Prepared as described above. Using work-up method B provided the title compound as white solid in 30% yield. $^1$H NMR (DMSO, 300 MHz) δ 9.96 (s, 1H), 8.97 (d, J=1.8 Hz, 1H), 8.73 (s, 1H), 8.72 (dd, J=1.8 Hz, J=4.9 Hz, 1H), 8.25 (dt, J=8.0 Hz, J=2.0 Hz, 1H), 8.14 (dd, J=2.1 Hz, J=5.2 Hz, 1H), 7.84 (td, J=1.9 Hz, J=7.1 Hz, 1H), 7.57–7.53 (m, 3H), 7.13–7.09 (m, 3H), 7.01 (d, J=8.4 Hz, 1H); Mass spec.: 335.11 (MH$^+$). Anal. Calcd. for C$_{18}$H$_{14}$N$_4$O$_3$: C=64.67%, H=4.22%, N=16.76%; found: C=64.41%, H=4.16%, N=16.50%.

EXAMPLE 148

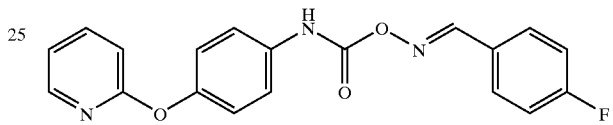

4-Fluorobenzaldehyde, O-[[[4-[(2-pyridinyl)oxy]phenyl]amino]carbonyl]oxime (Scheme 4, Compound L) Prepared as described above. Using workup method B provided the title compound as white solid in 22% yield. $^1$H NMR (CDCl$_3$, 500 MHz) δ 8.39 (s, 1H), 8.20 (dd, J=4.9 Hz, J=1.4 Hz, 1H), 8.05 (br, 1H), 7.75–7.68 (m, 3H), 7.55 (d, J=8.85 Hz, 2H), 7.19–7.14 (m, 4H), 7.00 (dd, J=5.1 Hz, J=7.2 Hz, 1H), 6.91 (d, J=8.30 Hz, 1H); $^{13}$C NMR (CDCl$_3$, 500 MHz) δ 165.9, 163.9, 163.7, 152.7, 151.9, 150.5, 147.5, 139.7, 133.5, 130.4, 130.3, 126.03, 126.00, 121.9, 121.2, 118.5, 116.5, 116.4, 111.4; Mass spec.: 352.25 (MH$^+$). Anal. Calcd. for C$_{19}$H$_{14}$N$_3$O$_3$F.0.36H$_2$O: C=63.78%, H=4.15%, N=11.74% found: C=63.74%, H=3.79%, N=11.77%.

EXAMPLE 149

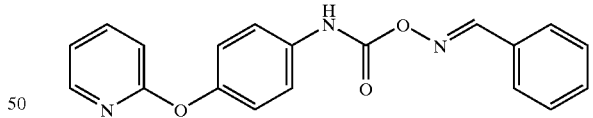

Benzaldehyde, O-[[[4-[(2-pyridinyl)oxy]phenyl]amino]carbonyl]oxime (Scheme 4, Compound L) Prepared as described above. Using workup method C provided the title compound as white solid in 76% yield. $^1$H NMR (CDCl$_3$, 500 MHz) δ 8.42 (s, 1H), 8.27 (dd, J=5.05 Hz, J=1.55 Hz, 1H), 8.17 (br, 1H), 7.76 (td, J=8.65 Hz, J=1.95 Hz, 1H,), 7.72 (d, J=7.05 Hz, 2H), 7.58 (d, J=8.85 Hz, 2H), 7.53 (tt, J=7.25 Hz, J=1.35 Hz, 1H), 7.48 (t, J=6.25 Hz, 2H), 7.15 (dt, J=8.85 Hz, J=3.2 Hz, 2H), 7.07 (dd, J=5.6 Hz, J=6.5 Hz, 1H), 6.89 (d, J=8.35 Hz, 1H); $^{13}$C NMR (CDCl$_3$, 500 MHz) δ 163.5, 153.9, 152.0, 150.2, 146.7, 140.7, 134.0, 132.0, 129.7, 129.1, 128.2, 121.9, 121.4, 118.7, 111.3; Mass spec.: 334.27 (MH$^+$). Anal. Calcd. for C$_{19}$H$_{15}$N$_3$O$_3$.0.185H$_2$O: C=67.78%, H=4.60%, N=12.48%; found: C=67.79%, H=4.29%, N=12.55%.

EXAMPLE 150

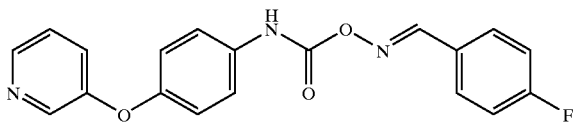

4-Fluorobenzaldehyde, O-[[[4-[(3-pyridinyl)oxy]phenyl]amino]carbonyl]oxime (Scheme 4, Compound L) Prepared as described above. Using workup method B provided the title compound as white solid in 93.5% yield. $^1$H NMR (CDCl$_3$, 500 MHz) δ 8.39 (s, 1H), 8.38 (d, J=12.5 Hz, 2H), 8.08 (br, 1H), 7.75–7.72 (m, 2H), 7.54 (d, J=8.8 Hz, 2H), 7.34–7.29 (m, 2H), 7.19–7.15 (t, J=8.45 Hz, 2H), 7.05 (d, J=8.8 Hz, 2H); Mass spec.: 352.09 (MH$^+$). Anal. Calcd. for C$_{19}$H$_{14}$FN$_3$O$_3$·1.38H$_2$O: C=60.66%, H=4.49%, N=11.17%; found: C=60.62%, H=4.24%, N=11.30%.

EXAMPLE 151

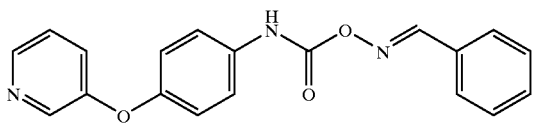

Benzaldehyde, O-[[[4-[(3-pyridinyl)oxy]phenyl]amino]carbonyl]oxime (Scheme 4, Compound L) This material was prepared by the general method where R=4-(3-pyridoxy)benzoic acid, R'=benzaldehyde oxime. Using workup method C and then B provided the title compound as white solid in 7% yield. $^1$H NMR (CDCl$_3$, 500 MHz) δ 8.43 (s, 1H), 8.38 (d, J=20.0 Hz, 2H), 8.17 (br, 1H), 7.12 (d, J=7.0 Hz, 2H), 7.56–7.46 (m, 5H), 7.32 (m, 2H), 7.05 (d, J=6.9 Hz, 2H); Mass spec.: 334.12 (MH$^+$). Anal. Calcd. for C$_{19}$H$_{15}$N$_3$O$_3$·0.21H$_2$O: C=67.69%, H=4.61%, N=12.46%; found: C=67.75%, H=4.81%, N=12.22%.

EXAMPLE 152

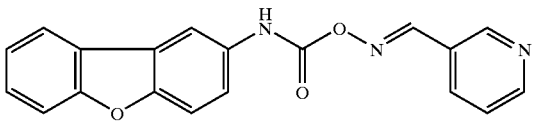

3-Pyridinecarboxaldehyde, O-[[(2-dibenzofuranyl)amino]carbonyl]oxime (Scheme 4, Compound L) Prepared as described above. Using work-up method A provided the title compound as white solid in 25% yield. $^1$H NMR (CDCl$_3$, 500 MHz) δ 8.94 (br, 1H), 8.77 (d, J=3.0 Hz, 1H), 8.49 (s, 1H), 8.25 (s, 1H), 8.14 (d, J=6.75 Hz, 1H), 8.09 (br, 1H), 7.97 (d, J=7.6 Hz, 1H), 7.57 (t, J=7.3 Hz, 2H), 7.50–7.46 (m, 3H), 7.36 (t, J=7.8 Hz, 1H); Mass spec.: 332.24 (MH$^+$). Anal. Calcd. for C$_{19}$H$_{13}$N$_3$O$_3$·0.19H$_2$O: C=68.19%, H=4.03%, N=12.56%; found: C=68.18%, H=3.99%, N=12.49.

EXAMPLE 153

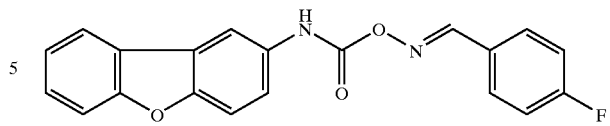

4-Fluorobenzaldehyde, O-[[(2-dibenzofuranyl)amino]carbonyl]oxime (Scheme 4, Compound L) Prepared as described above. Using workup method C provided the title compound as white solid in 8% yield. $^1$H NMR (CDCl$_3$, 500 MHz) δ 8.43 (s, 1H), 8.25 (s, 1H), 8.20 (br, 1H), 7.97 (dd, J=7.7 Hz, J=0.45 Hz, 1H), 7.76 (m, 2H), 7.56 (t, J=9.75 Hz, 2H), 7.48 (t, J=7.3 Hz, 2H), 7.35 (t, J=7.5 Hz, 1H), 7.19 (t, J=8.65 Hz, 2H); $^{13}$C NMR (CDCl$_3$, 500 MHz) δ 156.9, 152.7, 152.3, 130.4, 130.3, 127,5, 122.8, 120.9, 116.5, 116.4, 111.9, 111.7; Mass spec.: 349.10 (MH$^+$). Anal. Calcd. for C$_{20}$H$_{13}$FN$_2$O$_3$: C=68.96%, H=3.76%, N=8.04%; found: C=68.82%, H=3.77%, N=7.77%.

EXAMPLE 154

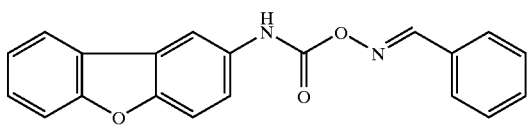

Benzaldehyde, O-[[(2-dibenzofuranyl)amino]carbonyl]oxime (Scheme 4, Compound L) Prepared as described above. Using work-up method C provided the title compound as white solid in 21% yield. $^1$H NMR (CDCl$_3$, 500 MHz) δ 8.46 (s, 1H), (8.29 (br, 1H), 8.26 (d, J=1.95 Hz, 1H), 7.97 (d, J=7.5 Hz, 1H), 7.75 (dd, J=8.5 Hz, J=1.5 Hz, 2H), 7.58–7.46 (m, 7H), 7.36 (t, J=7.7 Hz, J=1H); $^{13}$C NMR (CDCl$_3$, 500 MHz) δ 156.9, 153.8, 153.2, 152.4, 132.1, 132.0, 129.7, 129.1, 128.3, 127.5, 124.9, 124.1, 122.8, 121.0, 120.0, 112.6, 111.9, 111.8; Mass spec.: 331.12 (MH$^+$). Anal. Calcd. for C$_{20}$H$_{14}$N$_2$O$_3$·0.135H$_2$O: C=72.19%, H=4.07%, N=8.42%; found: C=72.20%, H=4.07%, N=8.33.

EXAMPLE 155

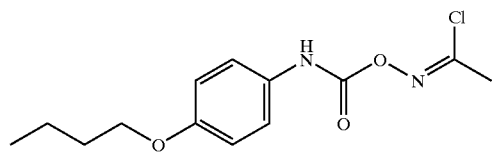

(1Z)-N-[[[(4-butoxyphenyl)amino]carbonyl]oxy]ethanimidoyl chloride This compound was synthesized in accordance with the following literature references: Ivanov, Y. et al., Anticholinesterase activity of O-carbamoylated acylhydroxymoyl chlorides, *Khim-Farm Zh.*, 26:5, 62–63, 1992; and Sakamoto, T. et al., A new synthesis of nitriles from N-alkoxyimidoyl halides with zinc, *Synthesis*, 9: 750–752, 1991.

Biological Data:

Homogenates of crude membranes were prepared from H4 cells that express transfected human FAAH (H4-FAAH cells). Briefly, cells were grown in DMEM supplemented with 10% FBS and Geneticin at a final concentration of 500

µg/ml (Gibco BRL, Rockville, Md.). Confluent cultures of H4-FAAH cells were rinsed twice with phosphate-buffered saline [138 mM NaCl, 4.1 mM KCl, 5.1 mM $Na_2PO_4$, 1.5 mM $KH_2PO_4$ (pH 7.5), 37° C.] and incubated for 5 to 10 minutes at 4° C. in lysis buffer [1 mM sodium bicarbonate]. Cells were transferred from plates to polypropylene tubes (16×100 mm), homogenized and centrifuged at 32,000×g for 30 minutes. Pellets were resuspended by homogenization in lysis buffer and centrifuged at 32,000×g for 30 minutes. Pellets were resuspended in lysis buffer (15–20 µg protein/ml) then stored at −80° C. until needed. On the day of an experiment, membranes were diluted to 2.67 µg protein/ml in 125 mM Tris-Cl, pH 9.0.

Activity of FAAH was measured using a modification of the method described by Omeir et al., 1995 (Life Sci 56:1999, 1995). Membrane homogenates (240 ng protein) were incubated at room temperature for one hour with 1.67 nM anandamide [ethanolamine 1-$^3$H] (available from American Radiolabeled Chemical Inc., St Louis, Mo.) and 10 µM anandamide (available from Sigma/RBI, St. Louis, Mo.) in the absence and presence of inhibitors. The reaction was stopped by the addition of 1 volume of a solution of 1:1 methanol and dichloroethane. The mixture was shaken and then centrifuged at 1000×g for 15 minutes to separate the aqueous and organic phases. An aliquot of the aqueous phase, containing [$^3$H]-ethanolamine was withdrawn and counted by scintillation spectroscopy. Data were expressed as the percentage of [$^3$H]-ethanolamine formed versus vehicle, after subtraction of the background radioactivity determined in the presence of 10 µM arachidonyl trifluoromethyl ketone (ATFMK), an inhibitor of FAAH. $IC_{50}$ values were determined using a four-parameter logistic equation for dose-response curves. Compounds for which $IC_{50}$ values are not provided herein showed no FAAH inhibition or marginal FAAH inhibition in preliminary tests.

TABLE I

| Ex. No. | $IC_{50}$ (nM) |
|---|---|
| 1 | ++++ |
| 2 | ++++ |
| 3 | ++++ |
| 4 | ++++ |
| 5 | ++++ |
| 6 | ++ |
| 7 | ++ |
| 8 | +++ |
| 9 | +++ |
| 10 | ++++ |
| 11 | ++++ |
| 12 | +++ |
| 13 | +++ |
| 14 | ++++ |
| 15 | ++ |
| 16 | +++ |
| 17 | ++++ |
| 18 | + |
| 19 | ++ |
| 20 | ++ |
| 21 | + |
| 22 | +++ |
| 23 | ++++ |
| 24 | ++++ |
| 25 | ++++ |
| 26 | ++++ |
| 27 | ++++ |
| 28 | ++++ |
| 29 | ++++ |
| 30 | ++++ |
| 31 | ++++ |
| 32 | ++++ |
| 33 | ++++ |

TABLE I-continued

| Ex. No. | $IC_{50}$ (nM) |
|---|---|
| 34 | ++++ |
| 35 | ++++ |
| 36 | ++++ |
| 37 | ++++ |
| 38 | ++++ |
| 39 | ++++ |
| 40 | ++++ |
| 41 | ++++ |
| 42 | ++++ |
| 43 | ++++ |
| 44 | +++ |
| 45 | ++++ |
| 46 | ++++ |
| 47 | ++++ |
| 48 | ++++ |
| 49 | ++++ |
| 50 | ++++ |
| 51 | ++++ |
| 52 | ++++ |
| 53 | ++++ |
| 54 | ++++ |
| 55 | ++++ |
| 56 | ++++ |
| 57 | ++++ |
| 58 | + |
| 59 | ++++ |
| 60 | +++ |
| 61 | + |
| 62 | +++ |
| 63 | +++ |
| 64 | +++ |
| 65 | +++ |
| 66 | + |
| 67 | +++ |
| 68 | +++ |
| 69 | +++ |
| 70 | +++ |
| 71 | ++++ |
| 72 | +++ |
| 73 | +++ |
| 74 | ++++ |
| 75 | ++++ |
| 76 | ++++ |
| 77 | ++++ |
| 78 | ++++ |
| 79 | ++++ |
| 80 | ++++ |
| 81 | ++++ |
| 82 | ++++ |
| 83 | ++++ |
| 84 | ++++ |
| 85 | ++++ |
| 86 | ++++ |
| 87 | ++++ |
| 88 | ++++ |
| 89 | + |
| 90 | +++ |
| 91 | ++++ |
| 92 | + |
| 93 | +++ |
| 94 | + |
| 95 | + |
| 96 | ++++ |
| 97 | +++ |
| 98 | ++++ |
| 99 | +++ |
| 100 | +++ |
| 101 | ++++ |
| 102 | ++++ |
| 103 | ++++ |
| 104 | +++ |
| 105 | ++++ |
| 106 | +++ |
| 107 | ++ |
| 108 | ++ |
| 109 | + |
| 110 | + |

TABLE I-continued

| Ex. No. | IC$_{50}$ (nM) |
|---|---|
| 111 | ++++ |
| 112 | ++++ |
| 113 | ++++ |
| 114 | ++++ |
| 115 | +++ |
| 116 | +++ |
| 117 | +++ |
| 118 | +++ |
| 119 | +++ |
| 120 | ++++ |
| 121 | ++++ |
| 122 | +++ |
| 123 | + |
| 124 | + |
| 125 | +++ |
| 126 | +++ |
| 127 | ++ |
| 128 | +++ |
| 129 | ++ |
| 130 | +++ |
| 131 | +++ |
| 132 | +++ |
| 133 | +++ |
| 134 | +++ |
| 135 | ++++ |
| 136 | +++ |
| 137 | +++ |
| 138 | +++ |
| 139 | ++++ |
| 140 | +++ |
| 141 | + |
| 142 | + |
| 143 | + |
| 144 | + |
| 145 | + |
| 146 | ++ |
| 147 | ++ |
| 148 | +++ |
| 149 | +++ |
| 150 | ++++ |
| 151 | ++++ |
| 152 | ++ |
| 153 | +++ |
| 154 | +++ |
| 155 | ++++ |

++++ = <10 nM;
+++ = ≧10–100 nM;
++ = ≧101–500 nM;
+ = >500 nM

The following in vivo pain models below utilized Example 5. CARRAGEENAN-INDUCED THERMAL HYPERALGESIA (Chronic Inflammatory Pain): Example 5 (40 mg/kg, i.p.) suppressed the development of thermal hyperalgesia induced by paw carrageenan. Paw carrageenan injection (◇, 0:45 hr, Carr) produced strong thermal hyperalgesia as evidenced by the short escape latencies seen in vehicle treated rats (◇, 2:15 hr, Carr) as compared to the long baseline latencies (0:00 hr). Animals pretreated with Example 5 (#1, 0:15 hr) failed to exhibit hyperalgesic responses (compare ◇ to ■ at 2:15 hr) and instead the latencies for drug treated animals were comparable to baseline. By 120 min post-carrageenan (2:45 hr), partial development of hyperalgesia was observed, that was reversed by a second injection of Example 5 (#2, 3:00 hr) which maintained thermal escape responses at basal levels for another hour (3:00–4:00 hr). No side effects were observed at 40 mg/kg, i.p. in drug (■) or vehicle (◇) treated controls (CEW=Cremophor:Ethanol:Water 10:10:80, 2 ml/kg). Data are mean+/−s.e.m. (n=8 per group). *p<0.05, **p<0.01 Tukey's HSD, compared to vehicle. The results are shown in FIG. 1.

Figure 2:
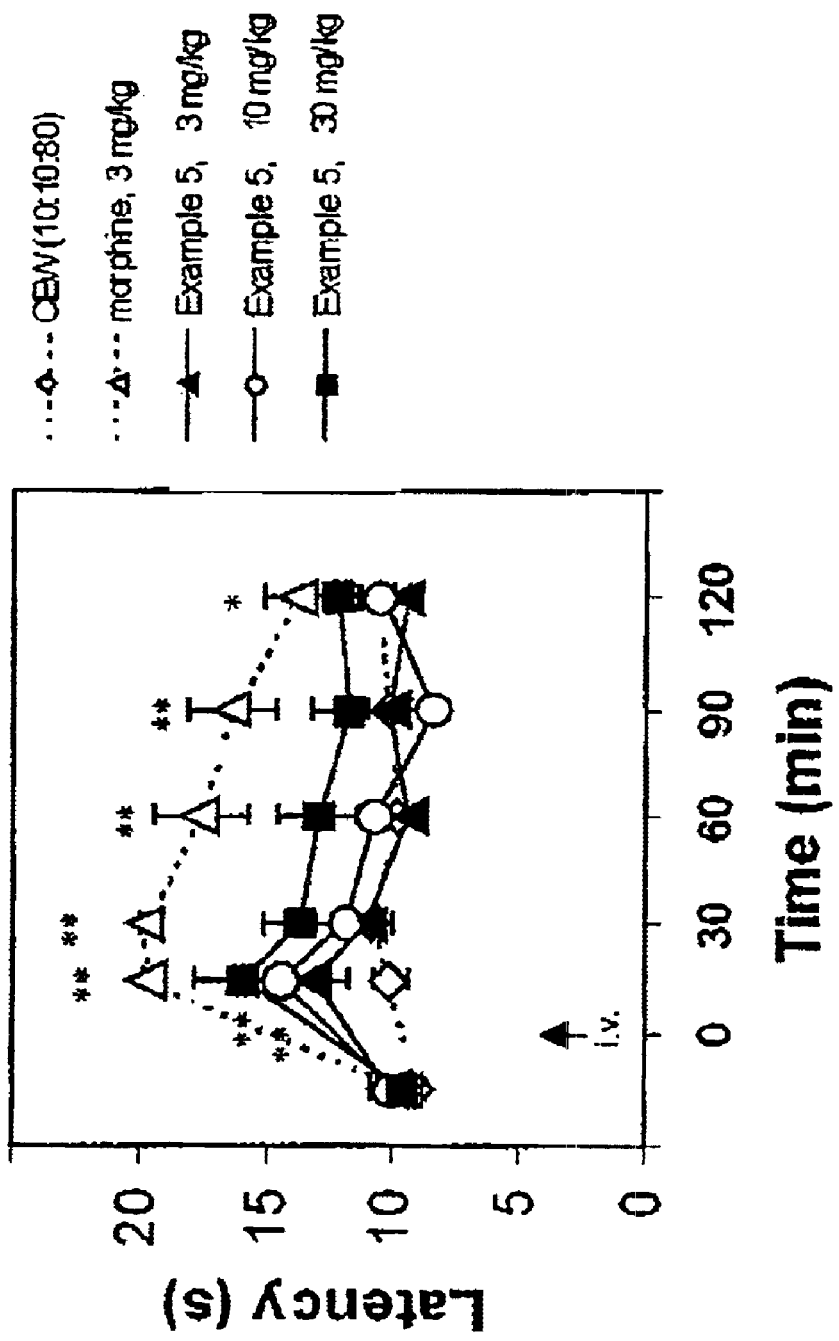
FIG. 2 illustrates results from a rat Hargreaves test used for measuring acute thermal pain.

HARGREAVES TEST (Acute Thermal Pain) Example 5 (10 & 30 mg/kg; 2 ml/kg; i.v. hand infusion) produced a significant reversal of acute thermal pain behavior at 15 min post injection, which did not persist beyond this time. No significant side effects were observed at 10 mg/kg. However, at 30 mg/kg side effects included strong sedation, reduced activity and splayed hindlimbs. Data are mean+/−s.e.m. (n=8 per group). **p<0.01 Dunnett's Test, compared to vehicle control. The results are shown in FIG. 2.

Figure 3:
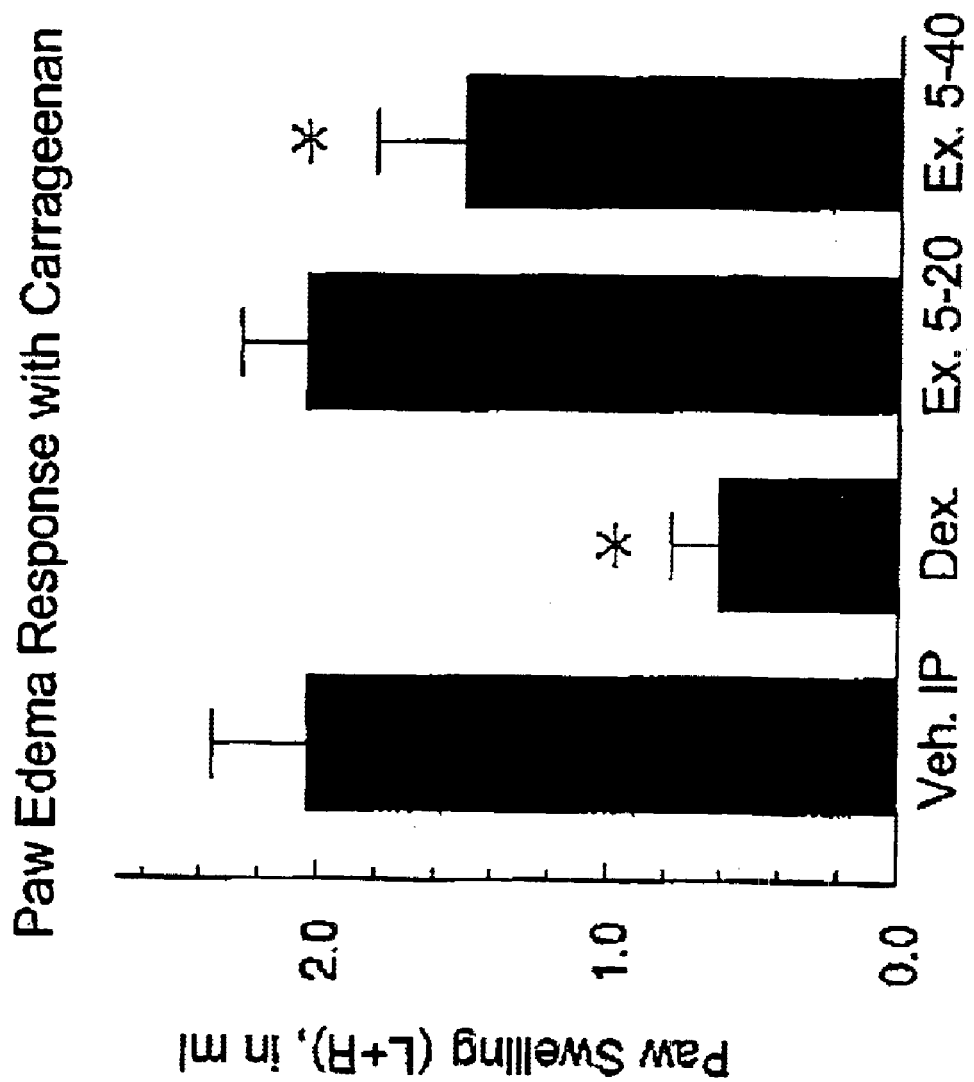
FIG. 3 illustrates results from a rat paw edema model used for measuring inflammation-induced edema.

PAW EDEMA MODEL (Inflammation-induced Edema) The effects of Example 5 on carrageenan-induced edema were examined in a quantitative manner (plethysmometry). Injections of carrageenan (2% lambda) into the plantar aspect of both hind paws, resulted in an increase in combined total paw volume (swelling) measured 3 hours post-injection. Example 5 inhibited swelling by 26% at 40 mg/kg (Ex. 5–40, ip administered at −30 min and +2 hr relative to carrageenan) but showed no efficacy at 20 mg/kg (Ex. 5–20, ip). The reference agent dexamethasone (Dex, 1 mg/kg, ip) inhibited swelling by 70%. FIG. 3 summarizes the data.

What is claimed is:

1. A compound of Formula I:

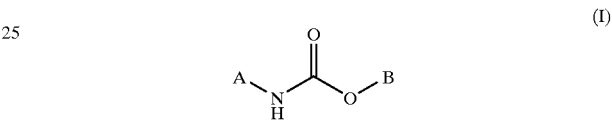

(I)

or a pharmaceutically acceptable salt or solvate thereof, wherein

A is dibenzofuranyl, dibenzothienyl, naphthyl, indolyl, fluorenyl, carbazolyl, or represented by Formula II:

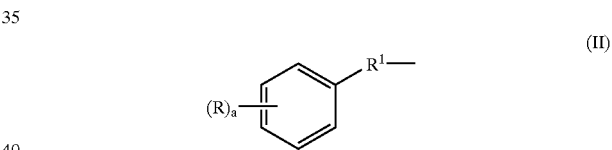

(II)

wherein a is 1 or 2;

R is $C_4$–$C_{12}$ alkoxy, or $R^1$ is a bond or a $C_{1-3}$ branched or linear aliphatic hydrocarbon; and B is represented by Formula III:

(III)

wherein $R^2$ is hydrogen, halo or $C_{1-4}$ alkyl;

$R^3$ is $C_{1-4}$ alkyl, pyridyl, halo, or phenyl optionally substituted with one or more of the same or different substituents selected from the group consisting of halo, $C_{1-4}$haloalkyl and nitro;

provided that if $R^2$ is halo, then $R^3$ is not halo; and if $R^3$ is halo, then $R^2$ is not halo.

2. The compound of claim 1 wherein A is dibenzofuranyl.

3. The compound of claim 1 wherein A is indolyl.

4. The compound of claim 1 wherein B is represented by Formula III:

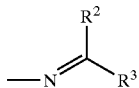
(III)

wherein
R² is hydrogen or methyl; and
R³ is methyl, or phenyl optionally substituted with one or more halo, haloalkyl or nitro.

5. The compound of claim 1 wherein B is represented by Formula III:

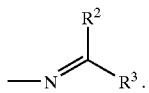
(III)

wherein
R² is hydrogen, or methyl, and
R³ is $C_{1-4}$ alkyl, pyridyl, or phenyl optionally substituted with one or more halo, haloalkyl or nitro.

6. A compound of Formula VI:

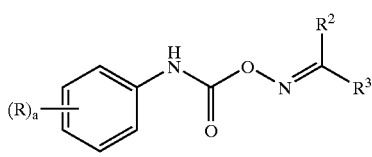
(VI)

or a pharmaceutically acceptable salt or solvate thereof, wherein
a is 1;
R is $C_{12}$ alkoxy;
R² is hydrogen or methyl; and
R³ is methyl, pyridyl, phenyl optionally substituted with one or more halo, haloalkyl or nitro.

7. The compound of claim 6 wherein R² is hydrogen and R³ is phenyl optionally substituted with one or more halo, haloalkyl or nitro.

8. The compound of claim 6 wherein R² is methyl and R³ is methyl.

9. The compound of claim 6 selected from the group consisting of:
pyridine-3-carbaldehyde, O-[[(4-undecyloxy-phenyl)amino]carbonyl]oxime;
pyridine-3-carbaldehyde, O-[[(4-nonyloxy-phenyl)amino]carbonyl]oxime;
4-fluorobenzaldehyde, O-[[(4-decyloxy-phenyl)amino]carbonyl]oxime;
4-fluorobenzaldehyde, O-[[(4-octyloxy-phenyl)amino]carbonyl]oxime;
benzaldehyde, O-[[(4-nonyloxy-phenyl)amino]carbonyl]oxime;
4-fluorobenzaldehyde, O-[[(4-nonyloxy-phenyl)amino]carbonyl]oxime;
3,4-difluorobenzaldehyde, O-[[(4-nonyloxy-phenyl)amino]carbonyl]oxime;
2,6-difluorobenzaldehyde, O-[[(4-nonyloxy-phenyl)amino]carbonyl]oxime;
2,4-difluorobenzaldehyde, O-[[(4-nonyloxy-phenyl)amino]carbonyl]oxime;
3-fluorobenzaldehyde, O-[[(4-nonyloxy-phenyl)amino]carbonyl]oxime;
pyridine-3-carbaldehyde, O-[[(4-nonyloxy-phenyl)amino]carbonyl]oxime;
benzaldehyde, O-[[(4-decyloxy-phenyl)amino]carbonyl]oxime;
pyridine-3-carbaldehyde, O-[[(4-decyloxy-phenyl)amino]carbonyl]oxime;
pyridine-3-carbaldehyde, O-[[(4-dodecyloxy-phenyl)amino]carbonyl]oxime;
benzaldehyde, O-[[(4-octyloxy-phenyl)amino]carbonyl]oxime;
2,3-difluorobenzaldehyde, O-[[(4-nonyloxy-phenyl)amino]carbonyl]oxime;
benzaldehyde, O-[[(4-undecyloxy-phenyl)amino]carbonyl]oxime;
2,4,5-trifluorobenzaldehyde, O-[[(4-nonyloxy-phenyl)amino]carbonyl]oxime;
benzaldehyde, O-[[(4-undecyloxy-phenyl)amino]carbonyl]oxime;
4-trifluoromethyl-benzaldehyde, O-[[(4-nonyloxy-phenyl)amino]carbonyl]oxime;
pyridine-3-carbaldehyde, O-[[(4-heptyloxy-phenyl)amino]carbonyl]oxime;
2-fluoro-3-trifluoromethyl-benzaldehyde, O-[[(4-nonyloxy-phenyl)amino]carbonyl]oxime;
(4-undecyloxy-phenyl)-carbamic acid phenyl ester;
propan-2-one, O-[[(4-heptyloxy-phenyl)amino]carbonyl]oxime;
propan-2-one, O-[[(4-nonyloxy-phenyl)amino]carbonyl]oxime;
2-fluoro-5-trifluoromethyl-benzaldehyde, O-[[(4-nonyloxy-phenyl)amino]carbonyl]oxime;
4-fluorobenzaldehyde, O-[[(4-pentyloxy-phenyl)amino]carbonyl]oxime;
4-fluorobenzaldehyde, O-[[(4-butoxy-phenyl)amino]carbonyl]oxime;
pyridine-3-carbaldehyde, O-[[(4-heptyloxy phenyl)amino]carbonyl]oxime;
4-fluorobenzaldehyde, O-[[(4-pentyloxy-phenyl)amino]carbonyl]oxime;
4-fluorobenzaldehyde, O-[[(4-dodecyloxy-phenyl)amino]carbonyl]oxime;
propan-2-one, O-[[(4-decyloxy-phenyl)amino]carbonyl]oxime;
benzaldehyde, O-[[(4-dodecyloxy-phenyl)amino]carbonyl]oxime;
benzaldehyde, O-[[(4-pentyloxy-phenyl)amino]carbonyl]oxime;
4-fluorobenzaldehyde, O-[[(4-heptyloxy-phenyl)amino]carbonyl]oxime;
benzaldehyde, O-[[(4-pentyloxy-phenyl)amino]carbonyl]oxime;
propan-2-one, O-[[(4-undecyloxy-phenyl)amino]carbonyl]oxime;
propan-2-one, O-[[(4-dodecyloxy-phenyl)amino]carbonyl]oxime;
pyridine-3-carbaldehyde, O-[[( 4-pentyloxy-phenyl)amino]carbonyl]oxime;

benzaldehyde, O-[[(4-heptyloxy-phenyl)amino]carbonyl] oxime;
benzaldehyde, O-[[(4-butoxy-phenyl)amino]carbonyl] oxime;
benzaldehyde, O-[[(4-hexyloxy-phenyl)amino]carbonyl] oxime;
propan-2-one, O-[[(4-heptyloxy-phenyl)amino]carbonyl] oxime;
pyridine-3-carbaldehyde, O-[[(4-hexyloxy-phenyl) amino]carbonyl]oxime; and
pyridine-3-carbaldehyde, O-[[(4-butoxy-phenyl)amino] carbonyl]oxime.

10. A method of treating neuropathic pain, acute pain, chronic pain, emesis, anxiety, feeding behaviors, movement disorders, glaucoma, brain injury, or cardiovascular disease in a mammal comprising administering to the mammal a therapeutically effective amount of a represented by the formula:

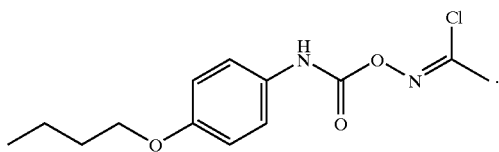

11. A method of treating neuropathic pain in a mammal comprising administering to the mammal a therapeutically effective amount of a compound as defined in claim 1.

12. A method of treating acute pain in a mammal comprising administering to the mammal a therapeutically effective amount of a compound as defined in claim 1.

13. A method of treating chronic pain in a mammal comprising administering to the mammal a therapeutically effective amount of a compound as defined in claim 1.

14. A method of treating emesis in a mammal comprising administering to the mammal a therapeutically effective amount of a compound as defined in claim 1.

15. A method of treating anxiety in a mammal comprising administering to the mammal a therapeutically effective amount of a compound as defined in claim 1.

16. A method of altering feeding behaviors in a mammal comprising administering to the mammal a therapeutically effective amount of a compound as defined in claim 1.

17. A method of treating movement disorders in a mammal comprising administering to the mammal a therapeutically effective amount of a compound as defined in claim 1.

18. A method treating glaucoma in a mammal comprising administering to the mammal a therapeutically effective amount of a compound as defined in claim 1.

19. A method of treating brain injury in a mammal comprising administering to the mammal a therapeutically effective amount of a compound as defined in claim 1.

20. A method of treating cardiovascular disease in a mammal comprising administering to the mammal a therapeutically effective amount of a compound as defined in claim 1.

21. A pharmaceutical composition comprising a compound as defined in claim 1 and a pharmaceutically acceptable carrier, adjuvant or diluent.

* * * * *